United States Patent
Jayanth et al.

(10) Patent No.: US 12,102,637 B2
(45) Date of Patent: *Oct. 1, 2024

(54) PHARMACEUTICAL FORMULATIONS FOR TREATING ENDOMETRIOSIS, UTERINE FIBROIDS, POLYCYSTIC OVARY SYNDROME OR ADENOMYOSIS

(71) Applicants: AbbVie Inc., North Chicago, IL (US); Neurocrine Biosciences, Inc., San Diego, CA (US)

(72) Inventors: Jayanthy Jayanth, Buffalo Grove, IL (US); Kevin C. Spence, Vernon Hills, IL (US); Gregory A. McClelland, San Diego, CA (US); Anna V. Stepanenko, Del Mar, CA (US); Tzuchi R. Ju, North Chicago, IL (US); Xi Shao, Lake Bluff, IL (US)

(73) Assignees: AbbVie Inc., North Chicago, IL (US); Neurocrine Biosciences, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/168,221

(22) Filed: Feb. 13, 2023

(65) Prior Publication Data
US 2023/0255968 A1  Aug. 17, 2023

Related U.S. Application Data

(63) Continuation of application No. 16/105,396, filed on Aug. 20, 2018.
(Continued)

(30) Foreign Application Priority Data

Jul. 23, 2018 (WO) ................ PCT/US2018/043321

(51) Int. Cl.
A61K 31/513 (2006.01)
A61K 9/20 (2006.01)
(Continued)

(52) U.S. Cl.
CPC .......... *A61K 31/513* (2013.01); *A61K 9/2009* (2013.01); *A61K 9/2018* (2013.01);
(Continued)

(58) Field of Classification Search
CPC .. A61K 31/513; A61K 9/2018; A61K 9/2009; A61K 9/2027; A61K 9/2059;
(Continued)

(56) References Cited

U.S. PATENT DOCUMENTS 4,311,606 A   1/1982   Kaeser
4,800,035 A   1/1989   Broze et al.
(Continued)

FOREIGN PATENT DOCUMENTS

CN    1794978 A    6/2006
CN    101056658 A    10/2007
(Continued)

OTHER PUBLICATIONS

Melis, G. B. et al., "Overview of elagolix for the treatment of endometriosis", Expert Opinion on Drug Metabolism & Toxicology, 2016, vol. 12 (5), 581-588.
(Continued)

*Primary Examiner* — Rayna Rodriguez
(74) *Attorney, Agent, or Firm* — Neal, Gerber & Eisenberg LLP

(57) ABSTRACT

The present disclosure relates to pharmaceutical compositions comprising a gonadotropin-releasing hormone (GnRH) antagonist and methods of preparing and using such compositions. The disclosure also relates to methods of facili-
(Continued)

tating release of a GnRH antagonist from a pharmaceutical composition.

16 Claims, 17 Drawing Sheets

Related U.S. Application Data

(60) Provisional application No. 62/660,102, filed on Apr. 19, 2018, provisional application No. 62/547,402, filed on Aug. 18, 2017.

(51) Int. Cl.
  *A61P 5/30* (2006.01)
  *A61P 15/00* (2006.01)

(52) U.S. Cl.
  CPC .......... *A61K 9/2027* (2013.01); *A61K 9/2059* (2013.01); *A61P 5/30* (2018.01); *A61P 15/00* (2018.01)

(58) Field of Classification Search
  CPC .. A61K 9/1611; A61K 9/1623; A61K 9/1652; A61K 9/2846; A61K 9/2866; A61K 9/5015; A61K 9/0053; A61K 9/2054; A61P 5/30; A61P 15/00; A61P 15/02; A61P 15/08
  See application file for complete search history.

(56) References Cited

U.S. PATENT DOCUMENTS

| | | | |
|---|---|---|---|
| 6,054,482 | A | 4/2000 | Augart et al. |
| 6,323,193 | B1 | 11/2001 | Somani et al. |
| 6,521,256 | B2 | 2/2003 | Makino et al. |
| 7,056,927 | B2 | 6/2006 | Guo et al. |
| 7,176,211 | B2 | 2/2007 | Guo et al. |
| 7,419,983 | B2 | 6/2008 | Guo et al. |
| 8,765,948 | B2 | 7/2014 | Gallagher et al. |
| 8,969,379 | B2 | 3/2015 | Furitsu et al. |
| 9,382,214 | B2 | 7/2016 | Gallagher et al. |
| 9,687,453 | B2 | 6/2017 | Uchida et al. |
| 9,868,706 | B2 | 1/2018 | Gallagher et al. |
| 9,949,974 | B2 | 4/2018 | Goss et al. |
| 10,350,170 | B2 | 7/2019 | Yamane et al. |
| 11,459,305 | B2 | 10/2022 | Gallagher et al. |
| 2003/0143276 | A1 | 7/2003 | Hsia et al. |
| 2005/0271717 | A1 | 12/2005 | Berchielli et al. |
| 2006/0057207 | A1 | 3/2006 | Ziegler et al. |
| 2009/0280169 | A1 | 11/2009 | Leonard |
| 2009/0280170 | A1 | 11/2009 | Lee et al. |
| 2011/0281929 | A1 | 11/2011 | Cuypers et al. |
| 2012/0165386 | A1 | 6/2012 | Agarwal et al. |
| 2013/0224296 | A1 | 8/2013 | Narang et al. |
| 2014/0271872 | A1 | 9/2014 | Pham et al. |
| 2015/0164917 | A1 | 6/2015 | Valducci et al. |
| 2016/0008777 | A1 | 1/2016 | Patel et al. |
| 2016/0354315 | A1 | 12/2016 | Li et al. |
| 2017/0007600 | A1 | 1/2017 | Gao et al. |
| 2017/0056403 | A1 | 3/2017 | Goss et al. |
| 2018/0235963 | A1 | 8/2018 | Goss et al. |
| 2018/0346428 | A1 | 12/2018 | Gallagher et al. |
| 2019/0054027 | A1 | 2/2019 | Qiu |
| 2019/0218191 | A1 | 7/2019 | Gallagher et al. |
| 2020/0255387 | A1 | 8/2020 | Gallagher et al. |

FOREIGN PATENT DOCUMENTS

| | | | | |
|---|---|---|---|---|
| CN | 100572491 | C | 12/2009 | |
| CN | 101001629 | B | 5/2010 | |
| CN | 105338981 | A | 2/2016 | |
| CN | 106236715 | A | 12/2016 | |
| CN | 106619547 | A | 5/2017 | |
| CN | 10812940 | A | 6/2018 | |
| CN | 108586359 | A | 9/2018 | |
| EP | 1066040 | A1 | 1/2001 | |
| JP | 2002326960 | A | 11/2002 | |
| TW | 201912157 | A | 4/2019 | |
| WO | 9944614 | A1 | 9/1999 | |
| WO | 0121194 | A2 | 3/2001 | |
| WO | 0155119 | A2 | 8/2001 | |
| WO | 0211732 | A1 | 2/2002 | |
| WO | 02061931 | A1 | 8/2002 | |
| WO | WO-03101431 | A1 * | 12/2003 | .......... A61K 31/496 |
| WO | 2004014356 | A1 | 2/2004 | |
| WO | 2004032905 | A1 | 4/2004 | |
| WO | 2005007165 | A1 | 1/2005 | |
| WO | 2005020978 | A1 | 3/2005 | |
| WO | 2005077332 | A2 | 8/2005 | |
| WO | 2006057507 | A1 | 1/2006 | |
| WO | 2007107835 | A2 | 9/2007 | |
| WO | 2007128495 | A2 | 11/2007 | |
| WO | 2009137078 | A1 | 11/2009 | |
| WO | 2011131601 | A1 | 10/2011 | |
| WO | 2014143669 | A1 | 9/2014 | |
| WO | 2016136849 | A1 | 9/2016 | |
| WO | 2017007895 | A1 | 1/2017 | |
| WO | 2017022144 | A1 | 2/2017 | |
| WO | 2017221144 | A1 | 12/2017 | |
| WO | 2018189212 | A1 | 10/2018 | |
| WO | 2018189213 | A1 | 10/2018 | |
| WO | 2018198086 | A1 | 11/2018 | |
| WO | 2018224063 | A2 | 12/2018 | |
| WO | 2020020999 | A1 | 1/2020 | |
| WO | 2020043763 | A1 | 3/2020 | |

OTHER PUBLICATIONS

Schwartz, M. et al., "Strategies for the management of hepatocellular carcinoma", Nat Clin Pract Oncol, 2007, vol. 4, pp. 424-432.
Archer, D. F. et al., "Elagolix for the management of heavy menstrual bleeding associated with uterine fibroids: results from a phase 2a proof-of-concept study", Fertility and Sterility, 2017, vol. 108 (1), pp. 152-160.
Bass, N.M & Williams, R.L., "Guide to drug dosage in hepatic disease", Clinical Pharmacokinetics, 1998, vol. 15, pp. 396-420.
Verbeeck, R.K., "Pharmacokinetics and dosage adjustment in patients with hepatic dysfunction", Eur J Clin Pharmacol, 2008, vol. 64, pp. 1147-1161.
Taylor H.S. et al.: "Treatment of Endometriosis-Associated Pain with Elagolix, an Oral GnRH Antagonist", The New England Journal of Medicine, vol. 377, No. 1, Jul. 6, 2017 (Jul. 6, 2017), pp. 28-40.
Hughey, et al., European Journal of Pharmaceutical Sciences, 48(4-5), 758-766 (2016). Abstract only.
Struthers, et al., The Journal of Clinical Endocrinology & Metabolism, 94(2), 545-551 (2009).
Carr, et al., Reproductive Sciences, 21(11), 1341-1351 (2014).
Rajabi-Siahboomi, Ali R., et al. "Excipient selection in oral solid dosage formulations containing moisture sensitive drugs." Excipient Applications in Formulation Design and Drug Delivery. Springer, Cham, 2015. 385-421.
Badawy, Sherif I. Farag, and Munir A. Hussain. "Microenvironmental pH modulation in solid dosage forms." Journal of pharmaceutical sciences 96.5 (2007): 948-959.
Mohr, Standards of Practice for the Pharmacy Technician, Lippincott Williams & Wilkins, Chapter 8, 2010.
Rowe, Handbook of Pharmaceutical Excipients, Pharmaceutical Press, 2009.
Co-pending U.S. Appl. No. 15/174,774, filed Jun. 6, 2016.
International Search Report and Written Opinion for Application No. PCT/US2018/47072, mailed Nov. 19, 2018, 11 pages.
International Search Report and Written Opinion for Application No. PCT/US2018/47073, mailed on Nov. 1, 2018, 16 pages.
The Menorrhagia Research Group, "Quantification of Menstrual Blood Loss," The Obstetrician & Gynaecologist., 2004, vol. 6, pp. 88-92.

(56) References Cited

OTHER PUBLICATIONS

Bai Xue-qian et al., "Application of microenvironmental pH modified technology in solid dispersions," Chinese Journal of New Drugs, 2011, vol. 20(20), pp. 1957-1965, abstract only.
Repka Michael A.: et al. "Applications of hot-melt extrusion for drug delivery", Expert opinion on drug delivery, vol. 5, No. 12, p. 1357-1376, Dec. 31, 2008.
Desai Ujwala et al.: "Melt granulation: an alternative to traditional granulation techniques" Indian Drugs, vol. 50, No. 3, p. 5-13, Mar. 31, 2013.
Co-pending U.S. Appl. No. 16/105,396, filed Aug. 20, 2018.
Co-pending U.S. Appl. No. 16/105,440, filed Aug. 20, 2018.
Anticancer Drugs that Inhibit Hormone Action, Medicinal Chemistry of Anticancer Drugs, 2008, Elsevier B. V., p. 53-91, dated 2008.
Mohamed Sabry et al., Innovative Oral Treatments of Uterine Leiomyoma, Obstetrics and Gynecology International, vol. 2012, Article ID 943635, dated Aug. 17, 2011.
Federal Register, Jan. 5, 2001, vol. 66(4), pp. 1099-1111.
Extended European Search Report for Application No. EP19845569, mailed on May 6, 2022, 4 pages.

* cited by examiner

PHARMACEUTICAL FORMULATIONS FOR TREATING ENDOMETRIOSIS, UTERINE FIBROIDS, POLYCYSTIC OVARY SYNDROME OR ADENOMYOSIS

CROSS-REFERENCE TO RELATED APPLICATIONS

The present application is a continuation of U.S. patent application Ser. No. 16/105,396, filed on Aug. 20, 2018, which seeks priority from provisional application 62/547,402 filed on Aug. 18, 2017, provisional application 62/660,102 filed on Apr. 19, 2018, and non-provisional application PCT/US2018/043321, filed on Jul. 23, 2018, all of which are incorporated herein by reference in its entirety for all purposes.

JOINT RESEARCH AGREEMENT

Subject matter disclosed in this application was made by or on behalf of AbbVie Inc. and/or Neurocrine Biosciences, Inc., whom are parties to a joint research agreement that was in effect on or before the effective filing date of this application, and such subject matter was made as a result of activities undertaken within the scope of the joint research agreement.

TECHNICAL FIELD

The present invention relates to pharmaceutical compositions of compound A, and pharmaceutically acceptable salts, and methods of use of such compositions.

BACKGROUND

Endometriosis is a disease in which tissue normally found in the uterine cavity (i.e., endometrium) is found outside the uterus, usually implanted on the peritoneal lining of the pelvis. Endometriosis affects an estimated 1 in 10 women of reproductive age and can cause pain, infertility, and sexual dysfunction. Growth of endometrial tissue outside of the uterine cavity is believed to be estrogen-dependent.

Uterine fibroids (leiomyomas) are benign tumors and are highly prevalent in women of reproductive age. Symptoms associated with uterine fibroids most commonly include heavy or prolonged menstrual bleeding, pelvic pressure and pelvic organ compression, back pain, and adverse reproductive outcomes. Heavy menstrual bleeding (HMB; menorrhagia, defined as greater than 80 mL per menstrual cycle) (The Menorrhagia Research Group. Quantification of menstrual blood loss. The Obstetrician & Gynaecologist. 2004; 6:88-92) is inconvenient and may lead to iron-deficiency anemia, which is the leading cause of surgical interventions that may include hysterectomy. Other symptoms, in particular pressure symptoms, are largely dependent on the size, number, and location of the tumors.

Although the pathogenesis has yet to be fully elucidated, the growth of uterine fibroids is known to be highly dependent on both estrogen and progestogen. Fibroids tend to shrink after menopause due to a decrease in hormone production.

Adenomyosis is a condition in which the inner lining of the uterus (the endometrium) breaks through the muscle wall of the uterus (the myometrium). Adenomyosis can cause menstrual cramps, lower abdominal pressure, and bloating before menstrual periods and can result in heavy periods. The condition can be located throughout the entire uterus or localized in one spot. Adenomyosis is a common condition. It is most often diagnosed in middle-aged women and women who have had children. Some studies also suggest that women who have had prior uterine surgery may be at risk for adenomyosis. Menorrhagia and intermenstrual bleeding are the most common complains, followed by pain, especially menstrual pain, and bladder and rectal pressure. Only surgery (myomectomy or hysterectomy) is regarded as curative.

Polycystic ovary syndrome (PCOS) is a hormonal disorder common among women of reproductive age. Women with PCOS may have infrequent or prolonged menstrual periods or excess male hormone (androgen) levels. The ovaries may develop numerous small collections of fluid (follicles) and fail to regularly release eggs.

Thus, there is a need in the art for new orally administered treatments for endometriosis, uterine fibroids, PCOS and adenomyosis and, in particular, management of pain associated with endometriosis, uterine fibroids, PCOS or adenomyosis and heavy menstrual bleeding associated with endometriosis, uterine fibroids, PCOS or adenomyosis. Moreover, there remains a need in the art to develop orally bioavailable dosage forms comprising such treatments and, in particular, a nonpeptide GnRH antagonist.

SUMMARY OF THE INVENTION

The disclosure is directed to pharmaceutical compositions comprising 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)-butyric acid (Compound A) or a pharmaceutically acceptable salt thereof; methods of using such compositions; and methods of facilitating the release of Compound A from such compositions.

The present application identifies at least two challenges to developing pharmaceutical formulations comprising Compound A or a pharmaceutically acceptable salt thereof. One challenge was that Compound A and, in particular, the monosodium salt of Compound A has a tendency to form a gel, particularly when present at an amount greater than about 10% by weight in the absence of an appropriate anti-gelling agent when administered orally in a solid dosage form. Such gel formation limits the dissolution of API and, ultimately, can lead to highly variable inter- and intra patient bioavailability. Another challenge was that Compound A can degrade to form a compound having a lactam moiety (referred to herein as Compound B). Reducing conversion of the drug substance into its lactam-containing degradation product is desirable, for example, to maintain safety and efficacy over the life of the product. Thus, it has been determined in the present application that a pharmaceutical composition reduces gelling of the API and/or reduces generation of the lactam degradation product (i.e., Compound B). Mutagenic impurities such as compound B are undesirable and should be reduced to maintain safety and efficacy of the product to very low level, and alternatively to the lowest levels possible.

In one aspect, the disclosed pharmaceutical compositions comprise Compound A or a pharmaceutically acceptable salt thereof, and at least one anti-gelling agent.

In certain embodiments, the salt of Compound A is the monosodium salt (sodium 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)butanoate).

In certain embodiments, the anti-gelling agent facilitates release of Compound A or a pharmaceutically acceptable salt thereof from a solid dosage form, such as a tablet.

In certain embodiments, the anti-gelling agent also acts as a stabilizer to, for example, reduce formation of (R)-5-(2-fluoro-3-methoxyphenyl)-1-(2-fluoro-6-(trifluoromethyl)benzyl)-6-methyl-3-(2-(2-oxopyrrolidin-1-yl)-2-phenyl-ethyl)pyrimidine-2,4(1H,3H)-dione (Compound B) in the composition relative to an otherwise identical composition without the anti-gelling agent.

In certain embodiments, the anti-gelling agent acts as a pH modifying agent, such as a buffer.

In certain embodiments, the anti-gelling agent is an alkali metal salt, such as sodium carbonate. Sodium carbonate may be either sodium carbonate monohydrate or sodium carbonate anhydrous. Other anti-gelling agents may be bases. Examples of bases include calcium hydroxide, guanidine, magnesium hydroxide, meglumine, piperidine, glucosamine, piperazine or TRIS (tris hydroxymethyl amino methane). In certain embodiments, the anti-gelling agents may be basic amino acids. Examples of basic amino acids include L-ornithine, L-lysine or L-arginine. In certain other embodiments the anti-gelling agent may be basic salts. Examples of basic salts include, sodium carbonate, potassium carbonate, trisodium phosphate, disodium hydrogen phosphate, disodium hydrogen phosphate, trisodium citrate dihydrate, guanidine carbonate. In certain embodiments, the anti-gelling agent may be Eudragit EPO.

In certain embodiments, the weight ratio of Compound A or a pharmaceutically acceptable salt thereof to the anti-gelling agent is from about 1:1 to about 20:1. The weight ratios may be selected in varying ranges, selected from a group consisting of 1:1, 2:1, 4:1, 6:1, 10:1 or 20:1. Thus, the ratio for example may range from 1:1 to 2:1 or 1:1 to 4:1 or 1:1 to 6:1 or 1:1 to 10:1 or 1:1 to 20:1.

In certain embodiments, the weight ratio of Compound A or a pharmaceutically acceptable salt thereof to the anti-gelling agent is about 2:1.

In certain embodiments, the anti-gelling agent is present in the pharmaceutical composition in an amount from about 5% to about 35% by weight of the pharmaceutical composition.

In certain embodiments, the anti-gelling agent is present in the pharmaceutical composition in an amount from about 15% to about 25% by weight of the pharmaceutical composition.

In certain embodiments, the pharmaceutical composition further comprises at least one additional excipient selected from the group consisting of a binder, a filler, a lubricant, a glidant, and a combination thereof.

In certain embodiments, the binder is polyvinylpyrrolidone.

In certain embodiments, the filler is a starch and/or mannitol. In certain embodiments, the filler is a water soluble filler, such as mannitol or pregelitanized starch or a combination thereof. In certain embodiments, the filler is a water insoluble filler, such as microcrystalline cellulose. In some such embodiments, the pharmaceutical composition further comprises a surfactant, such as sodium lauryl sulfate.

In certain embodiments, the lubricant is magnesium stearate.

In certain embodiments, the glidant is colloidal silicon dioxide.

In certain embodiments, the pharmaceutical composition is an oral dosage form. In some such embodiments, the oral dosage form is a tablet.

In certain embodiments, the pharmaceutical composition comprises Compound A or a pharmaceutically acceptable salt thereof in an amount of about 100 mg to about 600 mg; and at least about 10% by weight of the anti-gelling agent. In certain embodiments, the pharmaceutical composition comprises Compound A or a pharmaceutically acceptable salt thereof in an amount of about 100 mg to about 350 mg; and at least about 10% by weight of the anti-gelling agent.

In one aspect, the disclosed pharmaceutical compositions comprise about 150 mg of Compound A or a pharmaceutically acceptable salt thereof, at least one anti-gelling agent, and, optionally, at least one binder. In certain embodiments, the anti-gelling agent is sodium carbonate, such as sodium carbonate monohydrate. In some such embodiments, the weight ratio of Compound A or a pharmaceutically acceptable salt thereof to sodium carbonate is about 2:1. In certain embodiments, the binder is polyvinylpyrrolidone. In certain embodiments, the salt of Compound A is the monosodium salt (sodium 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)butanoate). In some such embodiments, the weight ratio of sodium 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)butanoate to sodium carbonate monohydrate is about 2:1.

In another aspect, the disclosed pharmaceutical compositions comprise about 200 mg of Compound A or a pharmaceutically acceptable salt thereof, at least one anti-gelling agent, and, optionally, at least one binder. In certain embodiments, the anti-gelling agent is sodium carbonate, such as sodium carbonate monohydrate. In some such embodiments, the weight ratio of Compound A or a pharmaceutically acceptable salt thereof to sodium carbonate is about 2:1. In certain embodiments, the binder is polyvinylpyrrolidone. In certain embodiments, the salt of Compound A is the monosodium salt (sodium 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)butanoate). In some such embodiments, the weight ratio of sodium 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)butanoate to sodium carbonate monohydrate is about 2:1.

In still another aspect, the disclosed pharmaceutical compositions comprise about 300 mg of Compound A or a pharmaceutically acceptable salt thereof, at least one anti-gelling agent, and, optionally, at least one binder. In certain embodiments, the anti-gelling agent is sodium carbonate, such as sodium carbonate monohydrate. In some such embodiments, the weight ratio of Compound A or a pharmaceutically acceptable salt thereof to sodium carbonate is about 2:1. In certain embodiments, the binder is polyvinylpyrrolidone. In certain embodiments, the salt of Compound A is the monosodium salt (sodium 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)butanoate). In some such embodiments, the weight ratio of sodium 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)butanoate to sodium carbonate monohydrate is about 2:1.

In certain embodiments, the pharmaceutical composition is a tablet comprising sodium 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)butanoate in an amount equivalent to about 125 mg to about 175 mg, such as about 150 mg of Compound A; and at least about 10%, such as between about 15% and about 20%, by weight of the anti-gelling agent; wherein the tablet when administered as a single dose to a population of human subjects provides an average Tmax value that is less than about 3 hours, such as, less than about 2 hours, for the population of human subjects. In certain embodiments, the pharmaceutical composition is a tablet sodium 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)butanoate in an amount equivalent to about 175 mg to about 225 mg, such as about 200 mg of Compound A; and at least about 10%, such as between about 15% and about 20%, by weight of the anti-gelling agent; wherein the tablet when administered as a single dose to a population of human subjects provides an average Tmax value that is less than about 3 hours, such as, less than about 2 hours, for the population of human subjects. In certain embodiments, the pharmaceutical composition is a tablet comprising sodium 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)butanoate in an amount equivalent to about 275 mg to about 325 mg, such as about 300 mg of Compound A; and at least about 10%, such as between about 15% and about 20%, by weight of the anti-gelling agent; wherein the tablet when administered as a single dose to a population of human subjects provides an average Tmax value that is less than about 3 hours, such as less than about 2 hours, for the population of human subjects.

In certain embodiments, the pharmaceutical composition is a tablet comprising sodium 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)butanoate in an amount equivalent to about 125 mg to about 175 mg, such as about 150 mg of Compound A; and at least about 10%, such as between about 15% and about 20%, by weight of the anti-gelling agent; wherein the tablet when administered as a single dose to a population of human subjects provides an average Cmax value that is at least about 380 ng/mL (~75% of 510) for the population of human subjects. In certain embodiments, the pharmaceutical composition is a tablet comprising sodium 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)butanoate in an amount equivalent to about 175 mg to about 225 mg, such as about 200 mg of Compound A; and at least about 10%, such as between about 15% and about 20%, by weight of the anti-gelling agent; wherein the tablet when administered as a single dose to a population of human subjects provides an average Cmax value that is at least about 550 ng/mL (~75% of 738) for the population of human subjects. In certain embodiments, the pharmaceutical composition is a tablet comprising sodium 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)butanoate in an amount equivalent to about 275 mg to about 325 mg, such as about 300 mg of Compound A; and at least about 10%, such as between about 15% and about 20%, by weight of the anti-gelling agent; wherein the tablet when administered as a single dose to a population of human subjects provides an average Cmax value that is at least about 1030 ng/mL (~75% of 1378) for the population of human subjects.

In certain embodiments, the pharmaceutical composition is a tablet comprising sodium 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)butanoate in an amount equivalent to about 125 mg to about 175 mg, such as about 150 mg of Compound A; and at least about 10%, such as between about 15% and about 20%, by weight of the anti-gelling agent; wherein the tablet when administered as a single dose to a population of human subjects provides an average AUCt value that is at least about 940 ng h/mL (~75% of 1263) for the population of human subjects. In certain embodiments, the pharmaceutical composition is a tablet comprising sodium 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)butanoate in an amount equivalent to about 175 mg to about 225 mg, such as about 200 mg of Compound A; and at least about 10%, such as between about 15% and about 20%, by weight of the anti-gelling agent; wherein the tablet when administered as a single dose to a population of human subjects provides an average AUCt value that is at least about 1410 ng h/mL (~75% of 1890) for the population of human subjects. In certain embodiments, the pharmaceutical composition is a tablet comprising sodium 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)butanoate in an amount equivalent to about 275 mg to about 325 mg, such as about 300 mg of Compound A; and at least about 10%, such as between about 15% and about 20%, by weight of the anti-gelling agent; wherein the tablet when administered as a single dose to a population of human subjects provides an average AUCt value that is at least about 2800 ng h/mL (~75% of 3732) for the population of human subjects.

In certain embodiments, the pharmaceutical composition is a tablet comprising sodium 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)butanoate in an amount equivalent to about 125 mg to about 175 mg, such as about 150 mg of Compound A; and at least about 10%, such as between about 15% and about 20%, by weight of the anti-gelling agent; wherein the tablet when administered as a single dose to a population of human subjects provides an average AUC∞ value that is at least about 950 ng h/mL (~75% of 1271) for the population of human subjects. In certain embodiments, the pharmaceutical composition is a tablet comprising sodium 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)butanoate in an amount equivalent to about 175 mg to about 225 mg, such as about 200 mg of Compound A; and at least about 10%, such as between about 15% and about 20%, by weight of the anti-gelling agent; wherein the tablet when administered as a single dose to a population of human subjects provides an average AUC∞ value that is at least about 1430 ng h/mL (~75% of 1900) for the population of human subjects. In certain embodiments, the pharmaceutical composition is a tablet comprising sodium 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)butanoate in an amount equivalent to about 275 mg to about 325 mg, such as about 300 mg of Compound A; and at least about 10%, such as between about 15% and about 20%, by weight of the anti-gelling agent; wherein the tablet when administered as a single dose to a population of human subjects provides an average AUC∞ value that is at least about 2820 ng h/mL (~75% of 3772) for the population of human subjects.

The disclosure is also directed to a pharmaceutical composition that is a single unit dosage form for oral administration in the form of a tablet comprising one or more pharmaceutically acceptable carriers and an amount of 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)-butyric acid (Compound A) or a pharmaceutically acceptable salt thereof, wherein the amount of Compound A is 150, 200, or 300 mg.

Also provided is a pharmaceutical composition comprising:
  a) about 20 to about 60% by weight of 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)-butyric acid (Compound A) or a pharmaceutically acceptable salt thereof;
  b) a binder;
  c) an anti-gelling agent, where the anti-gelling agent acts as a stabilizer to reduce formation of (R)-5-(2-fluoro-3-methoxyphenyl)-1-(2-fluoro-6-(trifluoromethyl)benzyl)-6-methyl-3-(2-(2-oxopyrrolidin-1-yl)-2-phenylethyl)pyrimidine-2,4(1H,3H)-dione (Compound B) in the composition; and
  d) a water soluble filler.

Also provided is a pharmaceutical composition comprising:
  a) about 33% by weight of sodium 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)butanoate;
  b) about 3% by weight of a binder;
  c) about 17% by weight of an alkali metal salt;
  d) about 41% by weight of a water soluble filler;
  e) about 2% by weight of a lubricant; and
  f) about 4% by weight of a film-coating.

Also provided is a pharmaceutical composition comprising one or more pharmaceutically acceptable carriers and an amount of 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)-butyric acid (Compound A) or a pharmaceutically acceptable salt thereof, wherein the pharmaceutical composition is bioequivalent to an immediate release formulation of Compound A, or a pharmaceutically acceptable salt thereof, having about the same amount of Compound A, or a pharmaceutically acceptable salt thereof.

The disclosure is also directed to pharmaceutical compositions comprising Compound A or a pharmaceutically acceptable salt thereof and an amount of an alkali metal salt sufficient to facilitate release of Compound A or the pharmaceutically acceptable salt thereof from the composition.

In certain embodiments, the release is measured using USP apparatus II in 900 mL of sodium phosphate, pH 6.8, at 37° C. and paddle speed of 50 rpm.

In certain embodiments, the release is measured using USP apparatus II in 900 mL of 0.1N hydrochloric acid, pH 1.2, at 37° C. and paddle speed of 50 rpm.

In certain embodiments, the release is measured using USP apparatus I in 900 mL of 0.1N hydrochloric acid, pH 1.2, at 37° C. and the speed of 100 rpm.

In certain embodiments, the alkali metal salt also acts as a stabilizer.

In certain embodiments, the alkali metal salt acts as a pH modifying agent, such as a buffer.

In certain embodiments, the weight ratio of Compound A or a pharmaceutically acceptable salt thereof to the alkali metal salt is from about 1:1 to about 4:1.

In certain embodiments, the weight ratio of Compound A or a pharmaceutically acceptable salt thereof to the alkali metal salt is about 2:1.

In certain embodiments, the alkali metal salt is present in the pharmaceutical composition in an amount from about 10% to about 30% by weight of the pharmaceutical composition.

In certain embodiments, the alkali metal salt is present in the pharmaceutical composition in an amount from about 15% to about 25% by weight of the pharmaceutical composition.

In certain embodiments, the pharmaceutical composition is an oral dosage form.

In certain embodiments, the oral dosage form is a tablet.

The disclosure is also directed to a solid oral dosage form, such as a tablet, comprising Compound A or a pharmaceutically acceptable salt thereof and sodium carbonate.

In certain embodiments, the salt of Compound A is a sodium salt.

In certain embodiments, the weight ratio of Compound A or a pharmaceutically acceptable salt thereof to sodium carbonate is from about 1:1 to about 4:1.

In certain embodiments, the weight ratio of Compound A or a pharmaceutically acceptable salt thereof to sodium carbonate is about 2:1.

In certain embodiments, sodium carbonate is present in the pharmaceutical composition in an amount from about 10% to about 30% by weight of the pharmaceutical composition.

In certain embodiments, sodium carbonate is present in the pharmaceutical composition in an amount from about 15% to about 25% by weight of the pharmaceutical composition.

The disclosure is also directed to methods of facilitating release of Compound A or a pharmaceutically acceptable salt thereof from an oral dosage form.

In certain embodiments, the methods comprise preparing a pharmaceutical composition comprising at least one anti-gelling agent and Compound A or a pharmaceutically acceptable salt thereof.

Compound A has a tendency to form a gel in the presence of water, further complicating the development process. Thus, in one aspect this disclosure provides methods of manufacturing a pharmaceutical composition comprising Compound A or a pharmaceutically acceptable salt thereof in the substantial absence of water. In certain embodiments, the pharmaceutical composition is manufactured using a roller compaction process.

The disclosure is also directed to methods for treating endometriosis in a subject in need of such treatment, wherein the method comprises administering to the subject a pharmaceutical composition of the present disclosure. In some such embodiments, the pharmaceutical composition is administered to the subject once daily (QD). In some such embodiments, the pharmaceutical composition is administered to the subject twice daily (BID).

The disclosure is also directed to pharmaceutical compositions for use in treating endometriosis.

The disclosure is also directed to methods for treating uterine fibroids in a subject in need of such treatment, wherein the method comprises administering to the subject a pharmaceutical composition of the present disclosure. In some such embodiments, the pharmaceutical composition is administered to the subject once daily (QD). In some such embodiments, the pharmaceutical composition is administered to the subject twice daily (BID).

The disclosure is also directed to pharmaceutical compositions for use in treating uterine fibroids.

The disclosure is also directed to methods for treating adenomyosis or adenomyoma in a subject in need of such treatment, wherein the method comprises administering to the subject a pharmaceutical composition of the present disclosure. In some such embodiments, the pharmaceutical composition is administered to the subject once daily (QD). In some such embodiments, the pharmaceutical composition is administered to the subject twice daily (BID).

The disclosure is also directed to pharmaceutical compositions for use in treating adenomyosis or adenomyoma.

The disclosure is also directed to methods for treating PCOS in a subject in need of such treatment, wherein the method comprises administering to the subject a pharmaceutical composition of the present disclosure. In some such embodiments, the pharmaceutical composition is administered to the subject once daily (QD). In some such embodiments, the pharmaceutical composition is administered to the subject twice daily (BID).

The disclosure is also directed to pharmaceutical compositions for use in treating PCOS.

The disclosure is also directed to methods for providing rapid suppression of luteinizing hormone (LH) and/or follicle-stimulating hormone (FSH) in a female patient with endometriosis, uterine fibroids, polycystic ovary syndrome (PCOS) or adenomyosis, wherein the method comprises administering to the female patient a pharmaceutical composition of the present disclosure. In some such embodiments, the pharmaceutical composition is administered to the subject once daily (QD). In some such embodiments, the pharmaceutical composition is administered to the female patient twice daily (BID).

The disclosure is also directed to methods for providing rapid suppression of luteinizing hormone (LH) and/or follicle-stimulating hormone (FSH) in a female patient with endometriosis, wherein the method comprises administering to the female patient a pharmaceutical composition of the present disclosure. In some such embodiments, the pharmaceutical composition is administered to the subject once daily (QD). In some such embodiments, the pharmaceutical composition is administered to the female patient twice daily (BID).

The disclosure is also directed to methods for providing rapid suppression of luteinizing hormone (LH) and/or follicle-stimulating hormone (FSH) in a female patient with uterine fibroids, wherein the method comprises administering to the female patient a pharmaceutical composition of the present disclosure. In some such embodiments, the pharmaceutical composition is administered to the subject once daily (QD). In some such embodiments, the pharmaceutical composition is administered to the female patient twice daily (BID).

The disclosure is also directed to methods for providing rapid suppression of luteinizing hormone (LH) and/or follicle-stimulating hormone (FSH) in a female patient with polycystic ovary syndrome (PCOS), wherein the method comprises administering to the female patient a pharmaceutical composition of the present disclosure. In some such embodiments, the pharmaceutical composition is administered to the subject once daily (QD). In some such embodiments, the pharmaceutical composition is administered to the female patient twice daily (BID).

The disclosure is also directed to methods for providing rapid suppression of luteinizing hormone (LH) and/or follicle-stimulating hormone (FSH) in a female patient with adenomyosis, wherein the method comprises administering to the female patient a pharmaceutical composition of the present disclosure. In some such embodiments, the pharmaceutical composition is administered to the subject once daily (QD). In some such embodiments, the pharmaceutical composition is administered to the female patient twice daily (BID).

The disclosure is also directed to pharmaceutical compositions for use in providing rapid suppression of LH and/or FSH in a female patient with endometriosis, uterine fibroids, polycystic ovary syndrome (PCOS) or adenomyosis.

In one embodiment, the disclosure is also directed to pharmaceutical compositions for use in providing rapid suppression of LH and/or FSH in a female patient with endometriosis.

In one embodiment, the disclosure is also directed to pharmaceutical compositions for use in providing rapid suppression of LH and/or FSH in a female patient with uterine fibroids.

In one embodiment, the disclosure is also directed to pharmaceutical compositions for use in providing rapid suppression of LH and/or FSH in a female patient with polycystic ovary syndrome.

In one embodiment, the disclosure is also directed to pharmaceutical compositions for use in providing rapid suppression of LH and/or FSH in a female patient with adenomyosis.

The disclosure is also directed to methods for providing partial to substantially full suppression of estradiol in a female patient with endometriosis, uterine fibroids, polycystic ovary syndrome (PCOS) or adenomyosis, wherein the method comprises administering to the subject a pharmaceutical composition of the present disclosure. In some such embodiments, the pharmaceutical composition is administered to the female patient once daily (QD). In some such embodiments, the pharmaceutical composition is administered to the female patient twice daily (BID).

In one embodiment, the disclosure is also directed to methods for providing partial to substantially full suppression of estradiol in a female patient with endometriosis, wherein the method comprises administering to the subject a pharmaceutical composition of the present disclosure. In some such embodiments, the pharmaceutical composition is administered to the female patient once daily (QD). In some such embodiments, the pharmaceutical composition is administered to the female patient twice daily (BID).

In one embodiment, the disclosure is also directed to methods for providing partial to substantially full suppression of estradiol in a female patient with uterine fibroids, wherein the method comprises administering to the subject a pharmaceutical composition of the present disclosure. In some such embodiments, the pharmaceutical composition is administered to the female patient once daily (QD). In some such embodiments, the pharmaceutical composition is administered to the female patient twice daily (BID).

In one embodiment, the disclosure is also directed to methods for providing partial to substantially full suppression of estradiol in a female patient with polycystic ovary syndrome, wherein the method comprises administering to the subject a pharmaceutical composition of the present disclosure. In some such embodiments, the pharmaceutical composition is administered to the female patient once daily (QD). In some such embodiments, the pharmaceutical composition is administered to the female patient twice daily (BID).

In one embodiment, the disclosure is also directed to methods for providing partial to substantially full suppression of estradiol in a female patient with adenomyosis, wherein the method comprises administering to the subject a pharmaceutical composition of the present disclosure. In some such embodiments, the pharmaceutical composition is administered to the female patient once daily (QD). In some such embodiments, the pharmaceutical composition is administered to the female patient twice daily (BID).

The disclosure is also directed to pharmaceutical compositions for use in providing partial to substantially full suppression of estradiol in a female patient with endometriosis, uterine fibroids, polycystic ovary syndrome (PCOS) or adenomyosis.

In one embodiment, the disclosure is also directed to pharmaceutical compositions for use in providing partial to substantially full suppression of estradiol in a female patient with endometriosis.

In one embodiment, the disclosure is also directed to pharmaceutical compositions for use in providing partial to substantially full suppression of estradiol in a female patient with uterine fibroids.

In one embodiment, the disclosure is also directed to pharmaceutical compositions for use in providing partial to substantially full suppression of estradiol in a female patient with polycystic ovary syndrome.

In one embodiment, the disclosure is also directed to pharmaceutical compositions for use in providing partial to substantially full suppression of estradiol in a female patient with adenomyosis.

The disclosure is also directed to methods of preparing such pharmaceutical compositions.

These and other objects of the invention are described in the following paragraphs. These objects should not be deemed to narrow the scope of the invention.

DETAILED DESCRIPTION OF THE INVENTION

Figure 1:
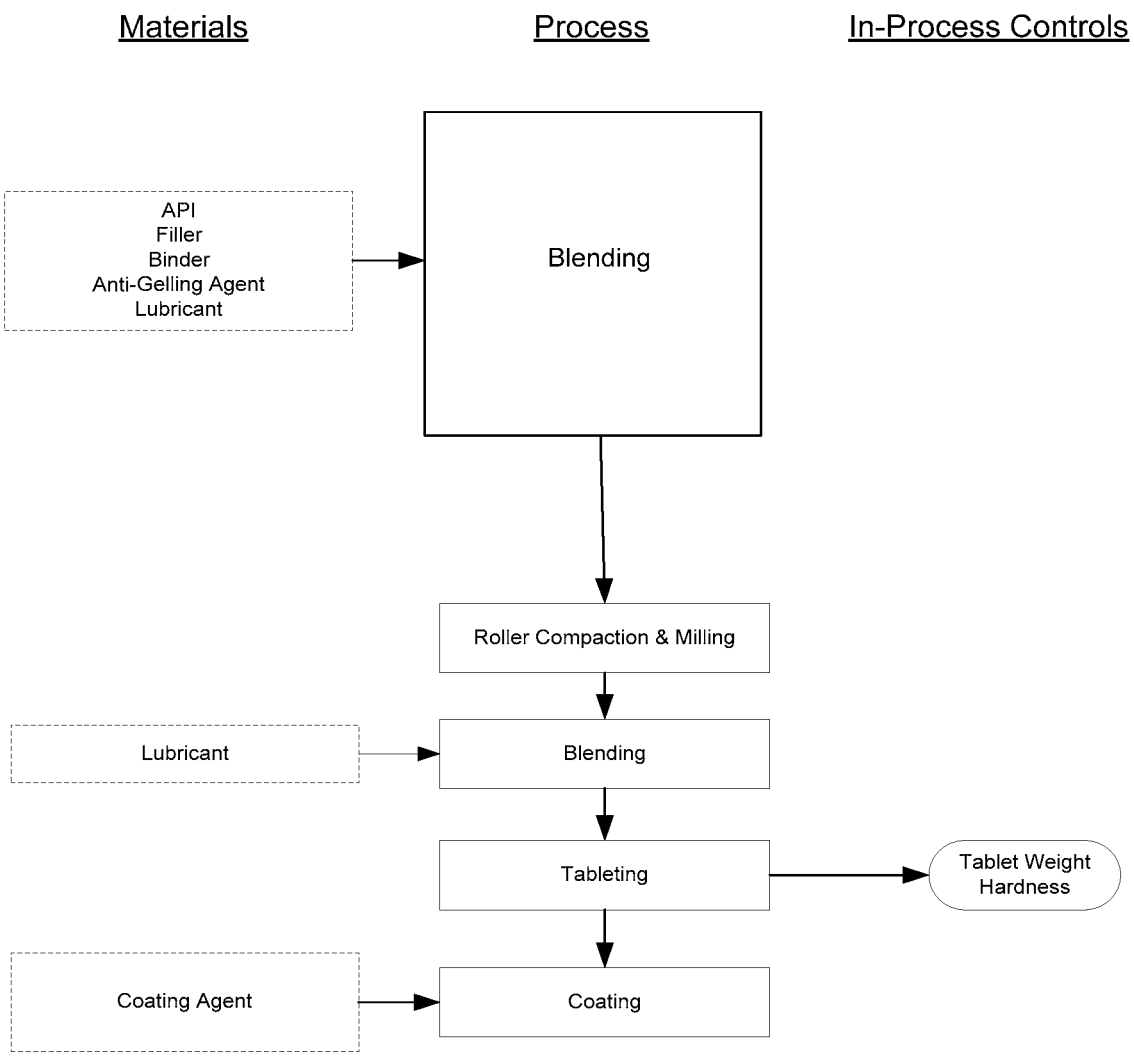
FIG. 1 is a roller compaction process flow diagram.

This detailed description is intended only to acquaint others skilled in the art with the present invention, its principles, and its practical application so that others skilled in the art may adapt and apply the invention in its numerous forms, as they may be best suited to the requirements of a particular use. This description and its specific examples are intended for purposes of illustration only. This invention, therefore, is not limited to the embodiments described in this patent application and may be variously modified.

A. DEFINITIONS

As used in the specification and the appended claims, unless specified to the contrary, the following terms have the meaning indicated:

The term "API" as used herein stands for "active pharmaceutical ingredient." The preferred API as disclosed herein is 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)-butyric acid (Compound A) or a pharmaceutically acceptable salt thereof and, such as is sodium 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)butanoate.

As used herein, the term "pharmaceutical composition" means a composition comprising Compound A or a pharmaceutically acceptable salt thereof and, optionally, one or more pharmaceutically acceptable excipients.

The term "pharmaceutically acceptable" is used adjectivally to mean that the modified noun is appropriate for use as a pharmaceutical product for human use or as a part of a pharmaceutical product for human use.

The term "subject" includes humans and other primates as well as other mammals. The term subject includes, for example, a healthy premenopausal female as well as a female patient having, for example, endometriosis, uterine fibroids, polycystic ovary syndrome (PCOS) or adenomyosis. In certain embodiments, the subject is a human. In certain embodiments, the subject is an adult human female. In certain embodiments, the subject is a woman, typically a premenopausal woman, having endometriosis. In certain embodiments, the subject is a woman, typically a premenopausal woman, having uterine fibroids. In certain embodiments, the subject is a woman, typically a premenopausal woman, having adenomyosis. In certain embodiments, the subject is a woman, typically a premenopausal woman, having PCOS.

The term "therapeutically effective amount" means a sufficient amount of the API or pharmaceutical composition to treat a condition, disorder, or disease, at a reasonable benefit/risk ratio applicable to any medical treatment.

The terms "treat", "treating" and "treatment" refer to a method of alleviating or abrogating a condition, disorder, or disease and/or the attendant signs and symptoms thereof.

B. DRUG SUBSTANCE

Pharmaceutical compositions disclosed herein comprise at least one active pharmaceutical ingredient: 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)-butyric acid (Compound A) or a pharmaceutically acceptable salt thereof.

Compound A has the following formula:

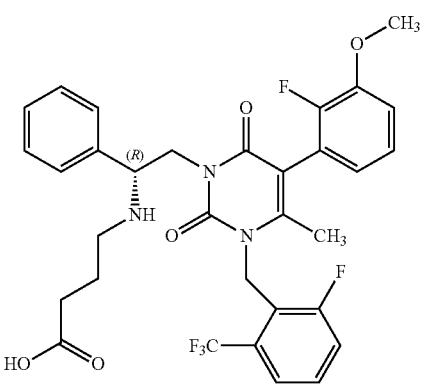

Compound A is an orally active, non-peptide GnRH antagonist and is unlike other GnRH agonists and injectable (peptide) GnRH antagonists. Compound A produces a dose dependent suppression of pituitary and ovarian hormones in women. Methods of making Compound A and a pharmaceutically acceptable salt thereof, as well as similar compounds, are described in WO2001/055119, WO 2005/007165, and WO2017/221144, the contents of which are herein incorporated by reference. Deuterated version of the drug substance is also contemplated to be within the scope of this invention. Deuterated versions of the drug substance are described in patent application CN108129400 A, the contents of which are incorporated herein by reference. Elagolix and elagolix sodium are used interchangeably to refer to the drug substance. Unless specifically directed, elagolix contemplates elagolix sodium within its scope.

In certain embodiments, 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)-butyric acid exists in zwitterionic form. For example, both the carboxylic acid and the tertiary amine are ionized and, thus, the molecule has no overall charge but does have charge separation. Such zwitterionic forms are included within the scope of the term "Compound A or a pharmaceutically acceptable salt thereof."

Compound A may be present in a pharmaceutical composition in the form of acid or base addition salts. Acid addition salts of the free amino compounds of the present invention may be prepared by methods well known in the art, and may be formed from organic and inorganic acids. Suitable organic acids include maleic, fumaric, benzoic, ascorbic, succinic, methanesulfonic, acetic, trifluoroacetic, oxalic, propionic, tartaric, salicylic, citric, gluconic, lactic, mandelic, cinnamic, aspartic, stearic, palmitic, glycolic, glutamic, and benzenesulfonic acids. Suitable inorganic acids include hydrochloric, hydrobromic, sulfuric, phosphoric, and nitric acids. Suitable base addition salts include those salts that form with the carboxylate anion and include salts formed with organic and inorganic cations such as those chosen from the alkali and alkaline earth metals (for example, lithium, sodium, potassium, magnesium, barium and calcium), as well as the ammonium ion and substituted derivatives thereof (for example, dibenzylammonium, benzylammonium, 2-hydroxyethylammonium, and the like). Thus, the term "pharmaceutically acceptable salt" of Compound A is intended to encompass any and all acceptable salt forms.

In certain embodiments, Compound A is present in a pharmaceutical composition in the form of a pharmaceutically acceptable salt. In certain embodiments, a pharmaceutically acceptable salt of Compound A is the sodium salt of Compound A. The monosodium salt of Compound A has a molecular formula of $C_{32}H_{29}F_5N_3O_5Na$, which corresponds to a molecular weight of about 653.6 (salt) and about 631.6 (free form). The monosodium salt of Compound A has the following formula:

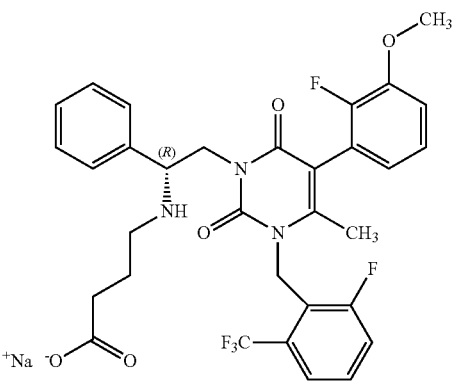

Elagolix has a pKa of about 8 and about 4, such as about 7.89 and about 4.15.

In certain embodiments, the monosodium salt is in the form of an amorphous solid. In certain embodiments, the monosodium salt is in crystalline form, such as a partially crystalline form. In some embodiments, amorphous Compound the monosodium form has an X-Ray Powder Diffraction (XRPD) pattern showing a lack of crystallinity. Elagolix and elagolix sodium are used interchangeably to refer to the active substance. Unless specifically, directed, elagolix contemplates elagolix sodium within its scope.

As used herein, and in the absence of a specific reference to a particular pharmaceutically acceptable salt of Compound A, any dosages, whether expressed in milligrams or as a percentage by weight or as a ratio with another ingredient, should be taken as referring to the amount of Compound A free form.

In certain embodiments, Compound A or a pharmaceutically acceptable salt thereof is present in a pharmaceutical composition in an amount from about 25 mg to about 650 mg of Compound A. In certain embodiments, Compound A or a pharmaceutically acceptable salt thereof is present in a pharmaceutical composition in an amount from about 45 mg to about 650 mg of Compound A. In certain embodiments, the amount of Compound A, or pharmaceutically acceptable salt thereof, is from about 50 mg to about 400 mg. In certain embodiments, the amount of Compound A, or pharmaceutically acceptable salt thereof, is from about 100 mg to about 350 mg. In some such embodiments, the amount of Compound A, or pharmaceutically acceptable salt thereof, is from about 140 mg to about 160 mg, such as about 150 mg. In other such embodiments, the amount of Compound A, or pharmaceutically acceptable salt thereof, is from about 190 mg to about 210 mg, such as about 200 mg. In still other embodiments, the amount of Compound A, or pharmaceutically acceptable salt thereof, is from about 290 mg to about 310 mg, such as about 300 mg.

C. PHARMACEUTICAL COMPOSITIONS

Pharmaceutical compositions comprising Compound A or a pharmaceutically acceptable salt thereof may be used to treat endometriosis, uterine fibroids, polycystic ovary syndrome (PCOS) or adenomyosis. In one embodiment, the pharmaceutical compositions comprising Compound A or a pharmaceutically acceptable salt thereof may be used to treat endometriosis. In one embodiment, the pharmaceutical compositions comprising Compound A or a pharmaceutically acceptable salt thereof may be used to treat uterine fibroids. In one embodiment, the pharmaceutical compositions comprising Compound A or a pharmaceutically acceptable salt thereof may be used to treat polycystic ovary syndrome (PCOS). In one embodiment, the pharmaceutical compositions comprising Compound A or a pharmaceutically acceptable salt thereof may be used to treat adenomyosis. Pharmaceutical compositions or dosage forms as described herein may be oral dosage forms, and, in particular, solid oral dosage forms, which can be administered to humans. An oral dosage form may be in the form of tablets.

The present disclosure provides pharmaceutical formulations and functional excipients to, inter alia, facilitate drug dissolution and/or enhance stability of the drug product and/or drug substance (e.g., by controlling the formation of degradation products).

The oral route of drug administration is the most convenient for patients, with tablets emerging as the most popular solid oral dosage form used today. However, the development of an immediate release tablet for Compound A was not straightforward. Initial tablets prepared by granulating Compound A with typical pharmaceutical excipients showed incomplete dissolution of Compound A into 900 mL of pH 1.2 0.1N HCL buffer. If the percent of drug in the tablet exceeded 10%, only 30-40% of the drug load was dissolved. The remaining amount of Compound A was present as an insoluble precipitate at the top of the dissolution vessels.

In certain embodiments, the pharmaceutical composition is an immediate release pharmaceutical composition. In at least one aspect, the pharmaceutical compositions comprising Compound A or a pharmaceutically acceptable salt thereof include an anti-gelling agent.

As referred to herein, an "anti-gelling agent" is an agent that reduces or prevents gel formation. In certain embodiments, the anti-gelling agent reduces or prevents gel formation relative to an otherwise identical composition without the anti-gelling agent. In certain embodiments, the anti-gelling agent reduces or prevents gel formation such that release of Compound A or a pharmaceutically acceptable salt thereof from a composition is facilitated. In certain embodiments, the anti-gelling agent improves release of Compound A or a pharmaceutically acceptable salt thereof from a pharmaceutical composition relative to that same pharmaceutical composition without the anti-gelling agent.

In certain embodiments, the anti-gelling agent acts as a pH modifying agent, such as a buffer.

In certain embodiments, the anti-gelling agent is an alkali metal salt, such as sodium carbonate. Sodium carbonate may be either sodium carbonate monohydrate or sodium carbonate anhydrous. Other anti-gelling agents may be bases. Examples of bases include calcium hydroxide, guanidine, magnesium hydroxide, meglumine, piperidine, glucosamine, piperazine or TRIS (tris hydroxymethyl amino methane). In certain embodiments, the anti-gelling agents may be basic amino acids. Examples of basic amino acids include L-ornithine, L-lysine or L-arginine. In certain other embodiments the anti-gelling agent may be basic salts. Examples of basic salts include, sodium carbonate, potassium carbonate, trisodium phosphate, disodium hydrogen phosphate, disodium hydrogen phosphate, trisodium citrate dihydrate, guanidine carbonate. In certain embodiments, the anti-gelling agent may be Eudragit EPO.

In certain embodiments, the weight ratio of Compound A or a pharmaceutically acceptable salt thereof to the anti-gelling agent is from about 1:1 to about 20:1. The weight ratios may be selected in varying ranges, selected from a group consisting of 1:1, 2:1, 4:1, 6:1, 10:1 or 20:1. Thus, the ratio for example may range from 1:1 to 2:1 or 1:1 to 4:1 or 1:1 to 6:1 or 1:1 to 10:1 or 1:1 to 20:1.

In certain embodiments, the anti-gelling agent is present in the pharmaceutical composition in an amount from about 3% to about 60% by weight (w/w) of the pharmaceutical composition. In certain embodiments, the anti-gelling agent is present in the pharmaceutical composition in an amount from about 3% to about 50% by weight (w/w) of the pharmaceutical composition. In certain embodiments, the anti-gelling agent is present in the pharmaceutical composition in an amount from about 5% to about 35% by weight (w/w) of the pharmaceutical composition. In certain embodiments, the anti-gelling agent is present in the pharmaceutical composition in an amount from about 10% to about 25% by weight (w/w) of the pharmaceutical composition. In certain embodiments, the anti-gelling agent is present in the pharmaceutical composition in an amount from about 15% to about 20% by weight (w/w) of the pharmaceutical composition.

In certain embodiments, the pharmaceutical composition is a film-coated tablet. In some such embodiments, the anti-gelling agent is present in an amount from about 3% to about 60%, alternatively, from about 3% to about 50%, alternatively from about 5% to about 35%, alternatively from about 10% to about 25%, alternatively from about 15% to about 20%, by weight of the uncoated tablet. In some such embodiments, the anti-gelling agent is present in an amount from about 3% to about 60%, alternatively, from about 3% to about 50%, alternatively from about 5% to about 35%, alternatively from about 10% to about 25%, alternatively from about 15% to about 20%, by weight of the coated tablet.

In certain embodiments, the weight ratio of Compound A or a pharmaceutically acceptable salt thereof to the anti-gelling agent is from about 0.5:1 to about 20:1. In certain embodiments, the weight ratio of Compound A or a pharmaceutically acceptable salt thereof to the anti-gelling agent is from about 0.5:1 to about 10:1. In certain embodiments, the weight ratio of Compound A or a pharmaceutically acceptable salt thereof to the anti-gelling agent is from about 0.5:1 to about 6:1. In certain embodiments, the weight ratio of Compound A or a pharmaceutically acceptable salt thereof to the anti-gelling agent is from about 0.5:1 to about 4:1. In certain embodiments, the weight ratio of Compound A or a pharmaceutically acceptable salt thereof to the anti-gelling agent is from about 1:1 to about 3:1. In certain embodiments, the weight ratio of Compound A or a pharmaceutically acceptable salt thereof to the anti-gelling agent is about 2:1.

In some embodiments, the pharmaceutical composition further comprises an anti-gelling agent in an amount effective to prevent formation of a gel mass which could decrease the rate of API release and bioavailability when the pharmaceutical composition is administered to the patient.

In some embodiments, the anti-gelling agent reduces or prevents gel formation such that release of Compound A or a pharmaceutically acceptable salt thereof from a pharmaceutical composition is facilitated. In some embodiments, the pharmaceutical composition further comprises an anti-gelling agent in an amount effective to alter the microenvironment of Compound A, or a pharmaceutically acceptable salt thereof, to facilitate its release from the pharmaceutical composition when administered to a patient. In some embodiments, the anti-gelling agent is present in an amount sufficient to provide a microenvironment to facilitate release of Compound A or the pharmaceutically acceptable salt thereof from the tablet in an aqueous medium. In some embodiments, facilitating release of Compound A, or a pharmaceutically acceptable salt thereof, results in more predictable release and absorption rates as compared to a pharmaceutical composition lacking the anti-gelling agent. In some embodiments, the anti-gelling agent improves release of Compound A or a pharmaceutically acceptable salt thereof from a pharmaceutical composition relative to that same pharmaceutical composition without the anti-gelling agent. In some embodiments, the pharmaceutical composition further comprises an anti-gelling agent in an amount effective to increase release of Compound A or the pharmaceutically acceptable salt thereof from the composition, wherein the release is measured using USP apparatus II in 900 mL of sodium phosphate, pH 6.8, at 37° C. and paddle speed of 50 rpm.

In some embodiments, the pharmaceutical composition further comprises an anti-gelling agent in an amount effective to reduce or prevent the formation of the zwitterionic form of Compound A or a pharmaceutically acceptable salt thereof. In some embodiments, the anti-gelling agent acts as a diluent.

In some embodiments, the pharmaceutical composition further comprises an anti-gelling agent in an amount effective to adjust the disintegration time of the pharmaceutical composition and/or the dissolution time of Compound A, or a pharmaceutically acceptable salt thereof, such as to provide a favorable microenvironment in the gastrointestinal tract for the dissolution of Compound A, or a pharmaceutically acceptable salt thereof.

In some embodiments, the pharmaceutical composition further comprises an anti-gelling agent in an amount effective to alter the microenvironment of Compound A, or a pharmaceutically acceptable salt thereof, by increasing the level of desiccation of the the microenvironment of Compound A, or a pharmaceutically acceptable salt thereof, when administered to a patient.

In some embodiments, the anti-gelling agent is selected from amines, amides, ammonium compounds and amino acids. In some embodiments, the anti-gelling agent is selected from ammonia, ammonium lactate, ammonium bicarbonate, ammonium hydroxide, ammonium phosphate dibasic, methylamine, dimethylamine, ethylamine, propylamine, trimethylamine, mono ethanolamine, di ethanolamine, tri ethanolamine, tri hydroxymethylaminomethane, ethylenediamine, allantoin, N,N-dimethylglycine, N-methyl glucamide, 6N-methyl glucamine, trometamol, meglucamine, L-ornithine, L-lysine and L-arginine, or a combination thereof.

In some embodiments, the anti-gelling agent is a water soluble salt of an acid selected from a group consisting of acetic acid, aceturic acid (N-acetylglycine), adipic acid, L-ascorbic acid, L-aspartic acid, butyric acid, decanoic acid, carbonic acid, citric acid, fumaric acid, galactaric acid, D-glucaric acid, D-glucoheptonic acid, D-gluconic acid, D-glucuronic acid, L-glutamic acid, glutaric acid, glycerophosphoric acid, glycolic acid, hippuric acid, hydrochloric acid, DL-lactic acid, lactobionic acid, lauric acid, maleic acid, L-malic acid, palmitic acid, phosphoric acid, pyruvic acid, sebacic acid, stearic acid, succinic acid, sulfuric acid, L-tartaric acid, and thiocyanic acid, or a combination thereof. In some embodiments, the anti-gelling agent is a water soluble salt of an acid selected from a group consisting of acetic acid, adipic acid, L-ascorbic acid, carbonic acid, citric acid, L-glutamic acid, hydrochloric acid, DL-lactic acid, lactobionic acid, lauric acid, maleic acid, L-malic acid, phosphoric acid, stearic acid, succinic acid, sulfuric acid, and L-tartaric acid, or a combination thereof.

In some embodiments, the anti-gelling agent is a water soluble salt of an acid selected from a group consisting of alginic acid, benzenesulfonic acid, benzoic acid, 2-(4-hydroxylbenzoyl)-benzoic acid, (+)-camphoric acid, octaonoic acid, cyclamic acid, di(tert-butyl)naphthalenedisulfonic acid, di(tert-butyl)naphthalenesulfonic acid, dodecylsulfuric acid, ethane-1,2-disulfonic acid, ethanesulfonic acid, 2-hydroxy-ethanesulfonic acid, gentisic acid, α-oxo-glutaric acid, isobutyric acid, malonic acid, methanesulfonic acid, naphthalene-1,5-disulfonic acid, naphthalene-2-sulfonic acid, 1-hydroxy-2-naphthoic acid, nicotinic acid, oleic acid, orotic acid, oxalic acid, embonic acid, propanoic acid, L-pyroglutamic acid, and para-toluenesulfonic acid, or a combination thereof. In some embodiments, the anti-gelling agent is a water soluble salt of an acid chosen from alginic acid, benzoic acid, octaonoic acid, nicotinic acid, and propanoic acid, or a combination thereof.

In some embodiments, the anti-gelling agent is a salt of carbonic or bicarbonic acid such as an alkali metal salt or an alkaline earth metal salt with a calcium-, magnesium-, sodium-, or potassium-base, or a combination thereof, for example, sodium carbonate. Sodium carbonate may be either sodium carbonate monohydrate or sodium carbonate anhydrous. In some embodiments, the anti-gelling agent is selected from a salt of citric acid with a calcium-, magnesium-, sodium-, and potassium-base, or a combination thereof. In some embodiments, the anti-gelling agent is selected from group consisting of a salt of phosphoric acid with a calcium-, magnesium-, sodium-, and potassium-base, or a combination thereof. In some embodiments, the anti-gelling agent is a selected from a group consisting of a salt of acetic acid with a calcium-, magnesium-, sodium-, and potassium-base, or a salt thereof. In some embodiments, the anti-gelling agent is selected from a group consisting of a salt of sulfuric acid with a calcium-, magnesium-, sodium-, and potassium-base, or a combination thereof. In some embodiments, the anti-gelling agent is selected from a group consisting of a salt of L-ascorbic acid a calcium-, magnesium-, sodium-, and potassium-base, or a combination thereof. In some embodiments, the anti-gelling agent is selected from a group consisting of a salt of L-aspartic acid with a calcium-, magnesium-, sodium-, and potassium-base, or a combination thereof. In some embodiments, the calcium-base is calcium hydroxide. In some embodiments, the magnesium-base is magnesium hydroxide. In some embodiments, the sodium-base is sodium hydroxide. In some embodiments, the potassium-base is potassium hydroxide. Other anti-gelling agents may be bases. Examples of bases include calcium hydroxide, guanidine, magnesium hydroxide, meglumine, piperidine, glucosamine, piperazine or TRIS (tris hydroxymethyl amino methane), or a combination thereof. In certain other embodiments the anti-gelling agent may be basic salts. Examples of basic salts include, sodium carbonate, potassium carbonate, trisodium phosphate, disodium hydrogen phosphate, disodium hydrogen phosphate, trisodium citrate dihydrate or guanidine carbonate, or a combination thereof.

In certain embodiments, the anti-gelling agent comprises a water soluble salt of a weak acid, such as a carbonate (e.g., sodium carbonate, sodium hydrogen carbonate, potassium carbonate, potassium hydrogen carbonate), an acetate (e.g., sodium acetate, potassium acetate, ammonium acetate), or a phosphate (e.g., mono-, di-, or tri-sodium phosphate), or a combination thereof.

In certain embodiments, the anti-gelling agent comprises a basic amino acid, such as arginine, lysine, histidine, or combinations thereof. In certain embodiments, the anti-gelling agent comprises basic polymers such as poly(meth)acrylate polymers, such as Eudragit E 100, Eudragit E 12, Eudragit E 5, Eudragit E PO, or combinations thereof.

In certain embodiments, the anti-gelling agent comprises an alkali metal salt or a combination thereof. Exemplary alkali metal salts include sodium carbonate, sodium hydrogen carbonate, or sodium phosphate.

In certain embodiments, the alkali metal salt is present in an amount sufficient to provide a microenvironment to reduce or prevent gel formation. In certain embodiments, the alkali metal salt is present in an amount sufficient to provide a microenvironment to facilitate release of Compound A or the pharmaceutically acceptable salt thereof from the tablet in an aqueous medium. In some embodiments, the pharmaceutical composition has a release profile such the release of Compound A, or a pharmaceutically acceptable salt thereof, or disintegration of the pharmaceutical composition occurs in the small intestine. In some embodiments, the pharmaceutical composition has a release profile such the release of Compound A, or a pharmaceutically acceptable salt thereof, or disintegration of the pharmaceutical composition occurs distal to the pyloric sphynctor. In some embodiments, the pharmaceutical composition has a release profile such the release of Compound A, or a pharmaceutically acceptable salt thereof, or disintegration of the pharmaceutical composition occurs distal to the duodenal bulb. In some embodiments, the pharmaceutical composition has a release profile such the release of Compound A, or a pharmaceutically acceptable salt thereof, or disintegration of the pharmaceutical composition occurs distal to the midduodenum. In some embodiments, the pharmaceutical composition has a release profile such the release of Compound A, or a pharmaceutically acceptable salt thereof, or disintegration of the pharmaceutical composition occurs distal to the duodenojejunal junction. In some embodiments, the pharmaceutical composition has a release profile such the release of Compound A, or a pharmaceutically acceptable salt thereof, or disintegration of the pharmaceutical composition occurs distal to the proximal jejunum.

In some embodiments, the pharmaceutical composition has a release profile such the release of Compound A, or a pharmaceutically acceptable salt thereof, or disintegration of the pharmaceutical composition occurs at a location where the pH is sufficiently high enough to avoid substantial gelling of Compound A.

In some embodiments, the pharmaceutical composition releases at least about 80% such as Compound A or the pharmaceutically acceptable salt thereof in about 45 minutes, such as at least about 80% of Compound A or the pharmaceutically acceptable salt thereof in about 30 minutes, measured using USP apparatus II in 900 mL of sodium phosphate, pH 6.8, at 37° C. and paddle speed of 50 rpm. In some embodiments, the pharmaceutical composition releases at least about 80% of Compound A or the pharmaceutically acceptable salt thereof in about 45 minutes, such as at least about 80% of Compound A or the pharmaceutically acceptable salt thereof in about 30 minutes, using USP apparatus II in 900 mL of hydrochloric acid, pH 1.2, at 37° C. and paddle speed of 50 rpm. In some embodiments, the pharmaceutical composition releases at least about 80% such as Compound A or the pharmaceutically acceptable salt thereof in about 45 minutes, such as at least about 80% of Compound A or the pharmaceutically acceptable salt thereof in about 30 minutes, measured using USP apparatus II in 900 mL of sodium phosphate, pH 6.8, at 37° C. and paddle speed of 50 rpm and at least about 80% of Compound A or the pharmaceutically acceptable salt thereof in about 45 minutes, such as at least about 80% of Compound A or the pharmaceutically acceptable salt thereof in about 30 minutes, using USP apparatus II in 900 mL of hydrochloric acid, pH 1.2, at 37° C. and paddle speed of 50 rpm. In some embodiments, the pharmaceutical composition provides a microenvironment for the release of Compound A or a pharmaceutically acceptable salt thereof wherein the release is pH independent. The analytical finish may be by a high performance liquid chromatography (HPLC) system with ultraviolet (UV) detection.

In some embodiments, the pharmaceutical composition further comprises an anti-gelling agent in an amount effective to modulate the pH of the microenvironment of Compound A, or a pharmaceutically acceptable salt thereof, in the gastrointestinal tract. In some embodiments, the microenvironment to facilitate release of Compound A or the pharmaceutically acceptable salt thereof from the tablet comprises a pH between the lower pKa of Compound A or a pharmaceutically acceptable salt thereof and the upper pKa of Compound A or a pharmaceutically acceptable salt thereof. Those values can be deteremined empirically by one of skill in the art using methods known in the art. In certain embodiments, the microenvironment to facilitate release of Compound A or the pharmaceutically acceptable salt thereof from the tablet comprises a pH of about 3.5 to about 8.0, such as about 4.0 to about 8.0.

In certain embodiments, the anti-gelling agent is sodium carbonate, such as sodium carbonate monohydrate or sodium carbonate anhydrous.

In certain embodiments, sodium carbonate is present in the pharmaceutical composition in an amount from about 3% to about 60% by weight (w/w) of the pharmaceutical composition. In certain embodiments, sodium carbonate is present in the pharmaceutical composition in an amount from about 3% to about 50% by weight (w/w) of the pharmaceutical composition. In certain embodiments, sodium carbonate is present in the pharmaceutical composition in an amount from about 5% to about 35% by weight (w/w) of the pharmaceutical composition. In certain embodiments, sodium carbonate is present in the pharmaceutical composition in an amount from about 10% to about 25% by weight (w/w) of the pharmaceutical composition. In certain embodiments, sodium carbonate is present in the pharmaceutical composition in an amount from about 15% to about 20% by weight (w/w) of the pharmaceutical composition.

In certain embodiments, the pharmaceutical composition is a film-coated tablet. In some such embodiments, sodium carbonate is present in an amount from about 3% to about 60%, alternatively from about 3% to about 50%, alternatively from about 5% to about 35%, alternatively from about 10% to about 25%, alternatively from about 15% to about 20%, by weight of the uncoated tablet. In some such embodiments, sodium carbonate is present in an amount from about 3% to about 60%, alternatively from about 3% to about 50%, alternatively from about 5% to about 35%, alternatively from about 10% to about 25%, alternatively from about 15% to about 20%, by weight of the coated tablet.

In certain embodiments, the weight ratio of Compound A or a pharmaceutically acceptable salt thereof to the anti-gelling agent is from about 0.5:1 to about 20:1. In certain embodiments, the weight ratio of Compound A or a pharmaceutically acceptable salt thereof to the anti-gelling agent is from about 0.5:1 to about 10:1. In certain embodiments, the weight ratio of Compound A or a pharmaceutically acceptable salt thereof to the anti-gelling agent is from about 0.5:1 to about 6:1. In certain embodiments, the weight ratio of Compound A or a pharmaceutically acceptable salt thereof to the anti-gelling agent is from about 0.5:1 to about 4:1. In certain embodiments, the weight ratio of Compound A or a pharmaceutically acceptable salt thereof to the anti-gelling agent is from about 1:1 to about 3:1. In certain embodiments, the weight ratio of Compound A or a pharmaceutically acceptable salt thereof to the anti-gelling agent is about 2:1.

In certain embodiments, the weight ratio of sodium 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)butanoate to sodium carbonate monohydrate is from about 0.5:1 to about 4:1. In certain embodiments, the weight ratio of sodium 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)butanoate to sodium carbonate monohydrate is from about 1:1 to about 3:1. In certain embodiments, the weight ratio of sodium 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)butanoate to sodium carbonate monohydrate is about 2:1.

As used herein, and in the absence of a specific reference to a particular hydrate (or anhydrous) form of sodium carbonate, any amounts, whether expressed in milligrams or as a percentage by weight or as a ratio with another ingredient, should be taken as referring to the amount of sodium carbonate monohydrate.

Release Profile Drugs administered via oral solid dosage forms should dissolve in vivo before systemic absorption can take place. There are number of factors which affect drug dissolution, including physicochemical properties of the drug substance. Poorly water soluble drugs, such as BCS class II (low solubility and high permeability), often exhibit poor dissolution and bioavailability. Even highly soluble drugs, such as BCS class III (high solubility and low permeability), may exhibit poor dissolution and bioavailability. Incomplete dissolution may result in highly variable inter- and intra patient bioavailability. It has been determined in the present application that Compound A is a BCS class III drug. It also has been determined in the present application that the monosodium salt of Compound A has a tendency to form a gel, particularly when present at an amount greater than about 10% by weight in the absence of an appropriate anti-gelling agent, when administered orally in a solid dosage form. Thus, it is desirable to provide oral solid dosage forms that facilitate drug dissolution.

In certain embodiments, dissolution is assessed utilizing USP apparatus II in 900 mL of sodium phosphate, pH 6.8, at 37° C. and paddle speed of 50 rpm. In certain embodiments, dissolution is assessed utilizing USP apparatus II in 900 mL of hydrochloric acid, pH 1.2, at 37° C. and paddle speed of 50 rpm. The analytical finish may be by a high performance liquid chromatography (HPLC) system with ultraviolet (UV) detection The solid oral dosage forms described herein will typically be in the form of a tablet and, in particular, an immediate release tablet. In certain embodiments, the immediate release tablet releases at least 80% of Compound A or a pharmaceutically acceptable salt thereof in 30 minutes, measured using USP apparatus II, in 900 mL of sodium phosphate, pH 6.8, at 37° C. and paddle speed of 50 rpm (AbbVie internal spec). In certain embodiments, the immediate release tablet releases at least 80% of Compound A or a pharmaceutically acceptable salt thereof in 45 minutes, measured using USP apparatus II, in 900 mL of sodium phosphate, pH 6.8, at 37° C. and paddle speed of 50 rpm (FDA).

(3) Stability In at least one aspect, the pharmaceutical compositions disclosed herein are stable during, for example, storage, distribution, and the duration of the product's shelf-life (e.g., up to two years at room temperature/ambient conditions). A stable pharmaceutical composition may, for example, exhibit less degradation of the API and/or lower amounts of degradation products. Degradation products that arise during storage of the drug substance and/or drug product are undesirable and, in extreme cases, might even be harmful to a patient being treated with such drug product. Thus, it is desirable to control the formation of degradation products, particularly potentially harmful impurities in the drug product.

Assay and degradation product determination of pharmaceutical compositions, particularly solid oral dosage forms, and more particularly tablets, may be performed using HPLC with UV detection.

Pharmaceutical compositions may be assessed for degradation products following storage for at least at least one week at least two weeks, at least one month, at least two months, at least three months, at least six months, at least twelve months, at least eighteen months, or at least twenty four months. In particular, degradation products may be assessed at time intervals of one, three, six, nine, twelve, eighteen, twenty four, thirty six, and/or forty eight months. Storage conditions may be long term, intermediate, or accelerated conditions. In particular, storage conditions may be, for example, 25° C.±2° C./40% relative humidity (RH)+5% RH, 25° C.±2° C./60% RH±5% RH, 30° C.±2° C./35%

RH±5% RH, 30° C.±2° C./65% RH±5% RH, 40° C.±2° C./25% RH±5% RH, 40° C.±2° C./75% RH±5% RH, 50° C.±2° C./75% RH±5% RH, 60° C.±2° C./5% RH±5% RH, 60° C.±2° C./40% RH±5% RH, 70° C.±2° C./5% RH±5% RH, 70° C. 2° C./75% RH±5% RH, and/or 80° C.±2° C./40% RH±5% RH.

One exemplary degradation product of Compound A is (R)-5-(2-fluoro-3-methoxyphenyl)-1-(2-fluoro-6-(trifluoromethyl)benzyl)-6-methyl-3-(2-(2-oxopyrrolidin-1-yl)-2-phenylethyl)pyrimidine-2,4(1H,3H)-dione (Compound B), which has the following structure:

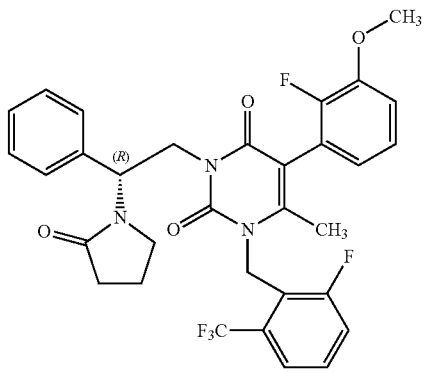

It has been identified in the present application that formation of Compound B was not adequately controlled in certain formulations. For example, in formulations without sodium carbonate monohydrate stored for one week at 65° C./75% RH, Compound B was present at greater than 1%. Thus, in certain embodiments, sodium carbonate is included in the pharmaceutical composition as a stabilizing agent to decrease degradation and/or to reduce or prevent gel formation.

In certain embodiments, sodium carbonate is present in amount from about 10% to about 25%, such as, from about 15% to about 20%, by weight of the pharmaceutical composition. In certain embodiments, the weight ratio of Compound A or a pharmaceutically acceptable salt thereof to sodium carbonate is from about 1:1 to about 4:1, such as, about 2:1 (drug substance:sodium carbonate).

In certain embodiments, Compound B is present in a pharmaceutical composition in an amount less than about 1.0% by weight after storage for at least one week, at least one month, at least two months, at least six months, at least twelve months, at least eighteen months, or at least twenty-four months at 25° C. and 60% relative humidity. In certain embodiments, Compound B is present in a pharmaceutical composition in an amount less than about 0.7% by weight after storage for at least one week, at least one month, at least two months, at least six months, at least twelve months, at least eighteen months, or at least twenty-four months at 25° C. and 60% relative humidity. In certain embodiments, Compound B is present in a pharmaceutical composition in an amount less than about 0.5% by weight after storage for at least one week, at least one month, at least two months, at least six months, at least twelve months, at least eighteen months, or at least twenty-four months at 25° C. and 60% relative humidity. In certain embodiments, Compound B is present in a pharmaceutical composition in an amount less than about 0.03% by weight after storage for at least one week, at least one month, at least two months, at least six months, at least twelve months, at least eighteen months, or at least twenty-four months at 25° C. and 60% relative humidity.

In one aspect, this disclosure provides a stable pharmaceutical composition comprising Compound A or pharmaceutically acceptable salt thereof. A stable pharmaceutical composition may, for example, contain less than 1% Compound B following storage for at least one week, and/or for at least one, at least three, at least six, at least nine, at least twelve, at least eighteen, or at least twenty-four months.

In certain embodiments, Compound B is present in a pharmaceutical composition in an amount less than about 1.0% by weight after storage for at least one week, for at least one month, at least two months, at least six months, at least twelve months, at least eighteen months, or at least twenty-four months at 40° C. and 75% relative humidity. In certain embodiments, Compound B is present in a pharmaceutical composition in an amount less than about 0.7% by weight after storage for at least one week, at least one month, at least two months, at least six months, at least twelve months, at least eighteen months, or at least twenty-four months at 40° C. and 75% relative humidity. In certain embodiments, Compound B is present in a pharmaceutical composition in an amount less than about 0.5% by weight after storage for at least one week, at least one month, at least two months, at least six months, at least twelve months, at least eighteen months, or at least twenty-four months at 40° C. and 75% relative humidity. In certain embodiments, Compound B is present in a pharmaceutical composition in an amount less than about 0.03% by weight after storage for at least one week, at least one month, at least two months, at least six months, at least twelve months, at least eighteen months, or at least twenty-four months at 40° C. and 75% relative humidity.

Pharmacokinetics: The solid oral dosage forms described herein will typically be in the form of a tablet. The provision of a tablet with particular pharmacokinetic parameters is a particular advantage afforded by the present invention. Pharmacokinetic parameters refer to any suitable pharmacokinetic parameters, such as Tmax, Cmax, and AUC. Parameters should be measured in accordance with standards and practices which would be acceptable to a pharmaceutical regulatory agency such as FDA, EMA, MHLW, or WHO. The values may be based on measurements taken at appropriate intervals following the time of tablet ingestion, such as every hour, or at increasingly sparse sampling intervals, such as 2, 4, 6, 8, 10, 12, 16, and 24 hours after ingestion. The pharmacokinetic parameters can be assessed either following a single-dose of drug or at steady state, such as following a single-dose. In certain embodiments, pharmacokinetic parameters are determined following a single dose of the pharmaceutical composition. In certain embodiments, pharmacokinetic parameters are determined in a multiple dosing regimen. For example, pharmacokinetic parameters may be determined after several dosing intervals, e.g., at steady state. The pharmacokinetic parameters can be assessed under fasting or fed conditions, such as under fasting conditions.

Cmax refers to the peak concentration and, in particular, the maximum observed plasma/serum concentration of drug. Tmax refers to the time to reach the peak concentration. AUCt refers to the area under the plasma concentration-time curve, where t is the time of the last measurable plasma concentration in the study. AUC∞ refers to the area under the plasma concentration-time curve from time zero to infinity following a single dose.

In certain embodiments, a solid oral dosage form (in particular a tablet) is provided as described herein, wherein the dosage form when administered as a single dose to a population of human subjects provides an average Tmax less than about 3 hours for the population of human subjects. In certain embodiments, a solid oral dosage form (in particular a tablet) is provided as described herein, wherein the dosage form when administered as a single dose to a population of human subjects provides an average Tmax from about 0.5 hours to about 2.0 hours for the population of human subjects. In some such embodiments, the solid oral dosage form is administered under fasting conditions.

In certain embodiments, a solid oral dosage form (in particular, a tablet) is provided as described herein, wherein the dosage comprises sodium 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)butanoate in an amount equivalent to about 150 mg of Compound A and wherein the dosage form when administered as a single dose to a population of human subjects provides an average Cmax from about 400 (~80% of 510) ng/mL to about 660 (~125% of 523) ng/mL, an average AUCt from about 1000 (~80% of 1263) ng hr/mL to about 1600 (~125% of 1273) ng hr/mL, and/or an average AUC∞ from about 1010 (~80% of 1271) ng hr/mL to about 1610 (~125% of 1281) ng hr/mL for the population of human subjects. In some such embodiments, the solid oral dosage form is administered under fasting conditions.

In certain embodiments, a solid oral dosage form (in particular a tablet) is provided as described herein, wherein the dosage comprises sodium 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)butanoate in an amount equivalent to about 200 mg of Compound A and wherein the dosage form when administered as a single dose to a population of human subjects provides an average Cmax from about 590 (~80% of 738) ng/mL to about 1100 (~125% of 879) ng/mL, such as from about 590 (~80% of 738) ng/mL to about 930 (~125% of 738) ng/mL, an average AUCt from about 1510 (~80% of 1890) ng hr/mL to about 2980 (~125% of 2384) ng hr/mL, such as from about 1520 (~80% of 1910) ng hr/mL to about 2390 (~125% of 1910) ng hr/mL, and/or an average AUC∞ from about 1520 (~80% of 1900) ng hr/mL to about 2990 (~125% of 2391) ng hr/mL, such as from about 1530 (~80% of 1920) ng hr/mL to about 2400 (~125% of 1920) ng hr/mL, for the population of human subjects. In some such embodiments, the solid oral dosage form is administered under fasting conditions.

In certain embodiments, a solid oral dosage form (in particular a tablet) is provided as described herein, wherein the dosage comprises sodium 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)butanoate in an amount equivalent to about 300 mg of Compound A and wherein the dosage form when administered as a single dose to a population of human subjects provides an average Cmax from about 1100 (~80% of 1378) ng/mL to about 1730 (~125% of 1378) ng/mL, an average AUCt from about 2990 (~80% of 3732) ng hr/mL to about 4670 (~125% of 3732) ng hr/mL, and/or an average AUC∞ from about 3020 (~80% of 3772) ng hr/mL to about 4720 (~125% of 3772) ng hr/mL for the population of human subjects. In some such embodiments, the solid oral dosage form is administered under fasting conditions.

In some embodiments, a solid oral dosage form (in particular a tablet) as described herein is provided, for which the 90% confidence interval of log-transformed Cmax, log-transformed AUCt, and/or log-transformed AUC∞ for Compound A or a pharmaceutically acceptable salt thereof in a population of human subjects falls completely within the range 80-125% of the log-transformed Cmax, log-transformed AUCt, and/or log-transformed AUC∞, respectively, of a reference tablet, wherein the reference tablet comprises sodium 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)butanoate in an amount equivalent to about 150 mg of Compound A; about 150 mg mannitol; about 44 mg pregelatinized starch; about 14 mg povidone; about 78 mg sodium carbonate monohydrate; about 8 mg magnesium stearate; and a film coating consisting of polyvinyl alcohol; titanium dioxide; polyethylene glycol; talc; and high tint carmine (such as Opadry® II Pink).

In some embodiments, a solid oral dosage form (in particular a tablet) as described herein is provided, for which the 90% confidence interval of log-transformed Cmax, log-transformed AUCt, and/or log-transformed AUC∞ for Compound A or a pharmaceutically acceptable salt thereof in a population of human subjects falls completely within the range 80-125% of the log-transformed Cmax, log-transformed AUCt, and/or log-transformed AUC∞, respectively, of a reference tablet, wherein the reference tablet comprises sodium 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)butanoate in an amount equivalent to about 200 mg of Compound A; about 200 mg mannitol; about 59 mg pregelatinized starch; about 18 mg povidone; about 104 mg sodium carbonate monohydrate; about 11 mg magnesium stearate; and a film coating consisting of polyvinyl alcohol; titanium dioxide; polyethylene glycol; talc; and iron oxide red (such as Opadry® II Salmon).

In some embodiments, a solid oral dosage form (in particular a tablet) as described herein is provided, for which the 90% confidence interval of log-transformed Cmax, log-transformed AUCt, and/or log-transformed AUC∞ for Compound A or a pharmaceutically acceptable salt thereof in a population of human subjects falls completely within the range 80-125% of the log-transformed Cmax, log-transformed AUCt, and/or log-transformed AUC∞, respectively, of a reference tablet, wherein the reference tablet comprises sodium 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)butanoate in an amount equivalent to about 300 mg of Compound A; mannitol; pregelatinized starch; povidone; sodium carbonate monohydrate; magnesium stearate; and a film coating.

(5) Hormone Suppression In some embodiments, the pharmaceutical composition is a tablet comprising Compound A or a pharmaceutically acceptable salt thereof wherein the tablet has bioavailability or exposure at levels equal to or greater than an oral solution formulation having the same amount of Compound A or a pharmaceutically acceptable salt thereof.

In certain embodiments, administration of a pharmaceutical composition comprising Compound A or a pharmaceutically acceptable salt thereof results in rapid suppression of luteinizing hormone (LH) and/or follicle-stimulating hormone (FSH) levels in a female patient with endometriosis, uterine fibroids, polycystic ovary syndrome (PCOS) or adenomyosis. In certain embodiments, administration of a pharmaceutical composition comprising Compound A or a pharmaceutically acceptable salt thereof results in partial to substantially full suppression of estradiol levels in a female patient with endometriosis, uterine fibroids, polycystic ovary syndrome (PCOS) or adenomyosis. In some such embodiments, estradiol levels are less than about 50 pg/mL. In some such embodiments, estradiol levels are between about 20 pg/mL and about 50 pg/mL. In some such embodiments, estradiol levels are less than about 20 pg/mL. In some such embodiments, estradiol levels are less than about 12 pg/mL (e.g., below the lowest limit of quantitation).

(6) Additional Excipients The pharmaceutical compositions may comprise other excipients such as excipients that function as fillers, binders, disintegrants, glidants and lubricants. Thus, a pharmaceutical composition comprising Compound A or a pharmaceutically acceptable salt thereof, further optionally comprises one or more conventional pharmaceutically acceptable excipients.

(6a) Fillers In certain embodiments, the disclosed pharmaceutical compositions comprise at least one excipient that functions as a filler. Fillers may include polyols, such as dextrose, isomalt, mannitol, sorbitol, lactose, and sucrose; natural or pre-gelatinized potato or corn starch; microcrystalline cellulose (e.g., Avicel®); or a combination thereof. Examples of suitable fillers include mannitol, such as spray dried mannitol (e.g., Pearlitol® 100SD, Pearlitol® 200SD); pregelatinized starch, such as Starch 1500@; microcrystalline cellulose, such as Avicel®; lactose monohydrate, such as Foremost® 316 Fast Flo®; mixtures of isomaltulose derivatives such as galenIQ™ 720; and other suitable fillers and combinations thereof.

In certain embodiments, the disclosed pharmaceutical compositions comprise at least one water soluble filler. In some such embodiments, the water soluble filler is a polyol, such as mannitol, sorbitol, lactose, or sucrose; a pregelatinized starch; or a combination thereof. In some such embodiments, the water soluble filler is mannitol. In some such embodiments, the water soluble filler is mannitol and pregelitanized starch. In certain embodiments, the disclosed pharmaceutical compositions comprise at least one water insoluble filler. In some such embodiments, the water insoluble filler is a starch, microcrystalline cellulose (e.g., Avicel®), or calcium phosphate. In some such embodiments, the disclosed pharmaceutical compositions comprise a water insoluble filler and a surfactant, such as sodium lauryl sulfate (SLS).

In certain embodiments, a filler is present in the pharmaceutical composition in an amount from about 5% to about 70% by weight (w/w) of the pharmaceutical composition. In certain embodiments, the filler is present in the pharmaceutical composition in an amount from about 10% to about 60% by weight (w/w) of the pharmaceutical composition. In certain embodiments, the filler is present in the pharmaceutical composition in an amount from about 20% to about 50% by weight (w/w) of the pharmaceutical composition. In certain embodiments, the filler is present in the pharmaceutical composition in an amount from about 30% to about 45% by weight (w/w) of the pharmaceutical composition.

In certain embodiments, the pharmaceutical composition includes a first filler in an amount from about 20% to about 50% by weight and a second filler in an amount from about 1% to about 20% by weight of the pharmaceutical composition. In certain embodiments, the pharmaceutical composition includes a first filler in an amount from about 25% to about 40% by weight and a second filler in an amount from about 5% to about 15% by weight of the pharmaceutical composition. In certain embodiments, the pharmaceutical composition includes a first filler in an amount from about 30% to about 35% by weight and a second filler in an amount from about 8% to about 12% by weight of the pharmaceutical composition. In certain embodiments, the pharmaceutical composition includes a first filler in an amount of about 33% by weight and a second filler in an amount of about 10% by weight of the pharmaceutical composition. In certain embodiments, the first filler is mannitol and the second filler is pregelitanized starch.

(6b) Binders In certain embodiments, the disclosed pharmaceutical compositions comprise at least one excipient that functions as a binder. Binders may include polyvinylpyrrolidone (e.g., povidone), a copolymer of vinylpyrrolidone and vinyl acetate (e.g., copovidone); cellulose, such as hydroxymethylpropylcellulose (HPMC), hydroxypropylethylcellulose, or microcrystalline cellulose; sucrose, starches, and combinations thereof. In certain embodiments, the binder is a hydrophilic polymer. The hydrophilic polymer may be selected from copolymer of N-vinyl lactam, cellulose ester, cellulose ether, polyalkylene glycol, polyacrylate, polymethacrylate, polyacrylamide, polyvinyl alcohol, vinyl acetate polymer, oligosaccharide, polysaccharide, or combinations thereof. In some such embodiments, the binder is polyvinylpyrrolidone.

In certain embodiments, a binder is present in the pharmaceutical composition in an amount from about 0.1% to about 20% by weight (w/w) of the pharmaceutical composition. In certain embodiments, a binder is present in the pharmaceutical composition in an amount from about 1% to about 10% by weight (w/w) of the pharmaceutical composition. In certain embodiments, a binder is present in the pharmaceutical composition in an amount from about 2% to about 5% by weight (w/w) of the pharmaceutical composition. In certain embodiments, the pharmaceutical composition includes about 3% by weight of a binder. In certain embodiments, the binder is polyvinylpyrrolidone.

(6c) Glidants In certain embodiments, the disclosed pharmaceutical compositions comprise at least one excipient that functions as a glidant. Glidants may include, for example, colloidal silicon dioxide, including highly dispersed silica (Aerosil®) or any other suitable glidant such as animal or vegetable fats or waxes.

In certain embodiments, a glidant is present in the pharmaceutical composition in an amount from about 0.1% to about 5% by weight (w/w) of the pharmaceutical composition. In certain embodiments, a glidant is present in the pharmaceutical composition in an amount from about 0.3% to about 2% by weight (w/w) of the pharmaceutical composition. In certain embodiments, a glidant is present in the pharmaceutical composition in an amount from about 0.3% to about 1.2% by weight (w/w) of the pharmaceutical composition. In certain embodiments, the pharmaceutical composition includes about 0.5% by weight of a glidant. In certain embodiments, the glidant is colloidal silicon dioxide.

In certain embodiments, a glidant is included in an intragranular portion of the pharmaceutical composition. In certain embodiments, the intragranular portion of the pharmaceutical composition comprises a glidant in an amount from about 0.1% to about 5% by weight (w/w), on the basis of the weight of the total pharmaceutical composition. In certain embodiments, the intragranular portion of the pharmaceutical composition comprises a glidant in an amount from about 0.5% to about 3% by weight (w/w), on the basis of the weight of the total pharmaceutical composition.

In certain embodiments, a glidant is included in an extragranular portion of the pharmaceutical composition. In certain embodiments, the extragranular portion of the pharmaceutical composition comprises a glidant in an amount from about 0.1% to about 5% by weight (w/w), on the basis of the weight of the total pharmaceutical composition. In certain embodiments, the extragranular portion of the pharmaceutical composition comprises a glidant in an amount from about 0.5% to about 3% by weight (w/w), on the basis of the weight of the total pharmaceutical composition.

In certain embodiments, a glidant is included in both an intragranular portion and an extragranular portion of the pharmaceutical composition. In certain embodiments, the intragranular portion of the pharmaceutical composition comprises a glidant in an amount from about 0.1% to about 5% by weight (w/w), on the basis of the weight of the total pharmaceutical composition and the extragranular portion of the pharmaceutical composition comprises a glidant in an amount from about 0.1% to about 5% by weight (w/w), on the basis of the weight of the total pharmaceutical composition. In certain embodiments, the intragranular portion of the pharmaceutical composition comprises a glidant in an amount from about 0.5% to about 3% by weight (w/w), on the basis of the weight of the total pharmaceutical composition and the extragranular portion of the pharmaceutical composition comprises a glidant in an amount from about 0.5% to about 3% by weight (w/w), on the basis of the weight of the total pharmaceutical composition.

(6c) Lubricants In certain embodiments, the disclosed pharmaceutical compositions comprise at least one excipient that functions as a lubricant. Lubricants may include, for example, magnesium and calcium stearates, sodium stearyl fumarate, talc, or any other suitable lubricant.

In certain embodiments, a lubricant is present in the pharmaceutical composition in an amount from about 0.1% to about 10% by weight (w/w) of the pharmaceutical composition. In certain embodiments, a lubricant is present in the pharmaceutical composition in an amount from about 0.5% to about 5% by weight (w/w) of the pharmaceutical composition. In certain embodiments, a lubricant is present in the pharmaceutical composition in an amount from about 1% to about 3% by weight (w/w) of the pharmaceutical composition. In certain embodiments, the pharmaceutical composition includes about 1.9% by weight of a lubricant. In certain embodiments, the lubricant is magnesium stearate.

In certain embodiments, a lubricant is included in an intragranular portion of the pharmaceutical composition. In certain embodiments, the intragranular portion of the pharmaceutical composition comprises a lubricant in an amount from about 0.5% to about 5% by weight (w/w), on the basis of the weight of the total pharmaceutical composition. In certain embodiments, the intragranular portion of the pharmaceutical composition comprises a lubricant in an amount from about 1% to about 3% by weight (w/w), on the basis of the weight of the total pharmaceutical composition.

In certain embodiments, a lubricant is included in an extragranular portion of the pharmaceutical composition. In certain embodiments, the extragranular portion of the pharmaceutical composition comprises a lubricant in an amount from about 0.5% to about 5% by weight (w/w), on the basis of the weight of the total pharmaceutical composition. In certain embodiments, the extragranular portion of the pharmaceutical composition comprises a lubricant in an amount from about 1% to about 3% by weight (w/w), on the basis of the weight of the total pharmaceutical composition. In certain embodiments, magnesium stearate is used as a lubricant and the magnesium stearate is in the extragranular portion.

In certain embodiments, a lubricant is included in both an intragranular portion and an extragranular portion of the pharmaceutical composition. In certain embodiments, the intragranular portion of the pharmaceutical composition comprises a lubricant in an amount from about 0.5% to about 5% by weight (w/w), on the basis of the weight of the total pharmaceutical composition and the extragranular portion of the pharmaceutical composition comprises a lubricant in an amount from about 0.5% to about 5% by weight (w/w), on the basis of the weight of the total pharmaceutical composition. In certain embodiments, the intragranular portion of the pharmaceutical composition comprises a lubricant in an amount from about 1% to about 3% by weight (w/w), on the basis of the weight of the total pharmaceutical composition and the extragranular portion of the pharmaceutical composition comprises a lubricant in an amount from about 1% to about 3% by weight (w/w), on the basis of the weight of the total pharmaceutical composition. In certain embodiments, the intragranular portion of the pharmaceutical composition comprises a lubricant in an amount of about 0.9% by weight (w/w), on the basis of the weight of the total pharmaceutical composition and the extragranular portion of the pharmaceutical composition comprises a lubricant in an amount of about 1% by weight (w/w), on the basis of the weight of the total pharmaceutical composition. In certain embodiments, magnesium stearate is used as a lubricant at a level of about 1.9% weight/weight of the formulation with about 0.9% added intragranular and about 1% added extragranular.

(6d) Disintegrants In certain embodiments, the disclosed pharmaceutical compositions comprise at least one excipient that functions as a disintegrant. Disintegrants may include, for example, sodium starch glycolate (e.g., Explotab), cross-linked polymers such as cross-linked modified starches, cross-linked polyvinylpyrrolidone, also known as crospovidone, and cross-linked carboxymethyl cellulose, also known as croscarmellose. In certain embodiments, a disintegrant is present in the pharmaceutical composition in an amount from about 0.1% to about 20% by weight (w/w) of the pharmaceutical composition.

(7) Film Coating In certain embodiments, the pharmaceutical composition is a tablet, which may be coated with any suitable coating such as a film coat. A film coat may be used to, for example, contribute to the ease with which the tablet can be swallowed. A film coat may also be employed to improve taste and provide an elegant appearance. The film coat may comprise a polyvinyl alcohol-polyethylene glycol graft copolymer, such as Opadry® II and Kollicoat® IR. The film coat may also comprise talc as an anti-adhesive. The film coat may account for less than about 5% by weight of the weight of the tablet.

In at least one aspect, this disclosure is directed to providing Compound A or a pharmaceutically acceptable salt thereof in a single, stable solid oral dosage form that is pharmacologically efficacious and physically acceptable. The solid oral dosage forms disclosed herein are intended for pharmaceutical use in human subjects. Accordingly, they should be of an appropriate size and weight for oral human administration (e.g., they should have a total weight of less than about 1.5 g), in addition to being therapeutically efficacious. In order to facilitate the intake of such a dosage form by a mammal, the dosage form may be shaped into an appropriate shape such as a round or elongated shape.

(8) Exemplary Formulations (Tables) For example, as set forth in Table 1, the disclosed pharmaceutical compositions may include one or more fillers, disintegrants, glidants and/or lubricants in combination with the active agent and anti-gelling agent.

Compound A referenced in Table 1 below is Compound A sodium salt and the corresponding weight percent is provided based on that salt form.

TABLE 1

| Ingredient | Function | Quantity (mg/Tablet) | %[a] (w/w) | Quantity (mg/Tablet) | %[a] (w/w) |
|---|---|---|---|---|---|
| Tablet Core | | | | | |
| *Intragranular* | | | | | |
| Compound A, sodium salt | Drug Substance | 155.2 | 33 | 207.0 | 33 |
| Mannitol, USP | Filler | 150.3 | 32 | 200.3 | 32 |
| Pregelatinized Starch, NF | Filler/Binder | 44.3 | 9 | 59.1 | 9 |
| Povidone K 29/32, USP | Binder | 13.8 | 3 | 18.4 | 3 |
| Sodium carbonate monohydrate, NF | Anti-gelling Agent | 78.0 | 17 | 104.0 | 17 |
| Magnesium stearate, NF | Lubricant | 3.9 | 1 | 5.2 | 1 |
| Weight subtotal of intragranular components | | 445.5 | | 594.0 | |
| *Extragranular* | | | | | |
| Magnesium stearate, NF | Lubricant | 4.5 | 1 | 6.0 | 1 |
| Uncoated tablet weight | | 450.0 | | 600.0 | |
| *Film Coating* | | | | | |
| Film-Coating Powder (Opadry® II) | Film Coat | 18.0 | 4 | 24.0 | 4 |
| Coated tablet weight | | 468.0 | 100 | 624.0 | 100 |

[a] Percents given based on the coated tablet weight. Total percentage may not be 100% due to rounding.

The amount (mg) of Compound A or pharmaceutically acceptable salt thereof referenced in the following tables refers to the amount (mg) of Compound A free form (i.e., in the case of a pharmaceutically acceptable salt, the free form equivalent weight).

In certain embodiments, the pharmaceutical composition comprises:

| Ingredient | Amount (mg) |
|---|---|
| Compound A or pharmaceutically acceptable salt thereof | 125-175 |
| Mannitol | 125-175 |
| Pregelitanized starch | 35-55 |
| Povidone | 13-15 |
| Sodium Carbonate | 66-90 |
| Magnesium Stearate | 7-10 |
| Optional film-coating | 16-20 |

In certain embodiments, the pharmaceutical composition comprises:

| Ingredient | Amount (mg) |
|---|---|
| Compound A or pharmaceutically acceptable salt thereof | 170-230 |
| Mannitol | 170-230 |
| Pregelitanized starch | 47-71 |
| Povidone | 17-20 |
| Sodium Carbonate | 88-120 |
| Magnesium Stearate | 9-13 |
| Optional film-coating | 21-27 |

In certain embodiments, the pharmaceutical composition comprises:

| Ingredient | Amount (mg) |
|---|---|
| Compound A or pharmaceutically acceptable salt thereof | 255-345 |
| Mannitol | 255-345 |
| Pregelitanized starch | 70-107 |
| Povidone | 25-30 |
| Sodium Carbonate | 132-180 |
| Magnesium Stearate | 14-20 |
| Optional film-coating | 24-30 |

In certain embodiments, the pharmaceutical composition comprises:

| Ingredient | Amount (mg) |
|---|---|
| Compound A or pharmaceutically acceptable salt thereof | 150 |
| Mannitol | 150 |
| Pregelitanized starch | 44.3 |
| Povidone | 13.8 |
| Sodium Carbonate | 78 |
| Magnesium Stearate | 8.4 |
| Optional film-coating | 18 |

In certain embodiments, the pharmaceutical composition comprises:

| Ingredient | Amount (mg) |
|---|---|
| Compound A or pharmaceutically acceptable salt thereof | 200 |
| Mannitol | 200 |
| Pregelitanized starch | 59.1 |
| Povidone | 18.4 |
| Sodium Carbonate | 104 |
| Magnesium Stearate | 11.2 |
| Optional film-coating | 24 |

In certain embodiments, the pharmaceutical composition comprises

| Ingredient | Amount (mg) |
| --- | --- |
| Compound A or pharmaceutically acceptable salt thereof | 300 |
| Mannitol | 300 |
| Pregelitanized starch | 88.7 |
| Povidone | 27.7 |
| Sodium Carbonate | 156 |
| Magnesium Stearate | 16.8 |
| Optional film-coating | 27 |

D. METHODS OF MANUFACTURE

The disclosed pharmaceutical compositions may be prepared by any suitable method. Methods such as direct compression, fluid bed granulation, roller compaction or dry granulation, and wet granulation may be used to blend Compound A or a pharmaceutically acceptable salt thereof with an anti-gelling agent and any other excipients of the pharmaceutical composition, including a water soluble filler or a water insoluble filler and a surfactant.

In certain embodiments, the disclosed pharmaceutical compositions are prepared using a wet granulation process and by compressing the final blend into tablets.

In certain embodiments, the disclosed pharmaceutical compositions are prepared using a roller compaction process. The roller compaction process may include any suitable steps. For example, as illustrated in FIG. 1, roller compaction may include steps such as blending the active agent with one or more intragranular excipients sized for blending; feeding the blend into a roller compactor to densify loose powder into ribbons; milling the resultant ribbons into granules; optionally blending the granules with extragranular excipients such as lubricants; compressing the granules into tablets; and optionally coating the tablets with a film-coating.

Each and every method, composition, or use described herein optionally includes the limitation "wherein the pharmaceutical composition is not an immediate release tablet comprising 155.2 mg of the sodium salt of Compound A (equivalent to 150 mg of Compound A) in combination with mannitol, sodium carbonate monohydrate, pregelatinized starch, povidone, magnesium stearate, polyvinyl alcohol, titanium dioxide, polyethylene glycol, talc, and carmine high tint."

Each and every method, composition, or use described herein also optionally includes the limitation "the pharmaceutical composition is not an immediate release tablet comprising 207.0 mg of the sodium salt of Compound A (equivalent to 200 mg of Compound A) in combination with mannitol, sodium carbonate monohydrate, pregelatinized starch, povidone, magnesium stearate, polyvinyl alcohol, titanium dioxide, polyethylene glycol, talc, and iron oxide red."

In some embodiments, the one or more pharmaceutically acceptable carriers is chosen from binders, fillers, diluents, disintegrants, wetting agents, lubricants, glidants, coloring agents, dye-migration inhibitors, sweetening agents, and flavoring agents.

Suitable binders or granulators include, but are not limited to, starches, such as corn starch, potato starch, and pre-gelatinized starch (e.g., STARCH 1500); gelatin; sugars, such as sucrose, glucose, dextrose, molasses, and lactose; natural and synthetic gums, such as acacia, alginic acid, alginates, extract of Irish moss, Panwar gum, ghatti gum, mucilage of isabgol husks, carboxymethylcellulose, methylcellulose, polyvinylpyrrolidone (PVP), Veegum, larch arabogalactan, powdered tragacanth, and guar gum; celluloses, such as ethyl cellulose, cellulose acetate, carboxymethyl cellulose calcium, sodium carboxymethyl cellulose, methyl cellulose, hydroxyethylcellulose (HEC), hydroxypropylcellulose (HPC), hydroxypropyl methyl cellulose (HPMC); microcrystalline celluloses, such as AVICEL-PH-101, AVICEL-PH-103, AVICEL RC-581, AVICEL-PH-105 (FMC Corp., Marcus Hook, PA); and mixtures thereof. Suitable fillers include, but are not limited to, talc, calcium carbonate, microcrystalline cellulose, powdered cellulose, dextrates, kaolin, mannitol, silicic acid, sorbitol, starch, pregelatinized starch, and mixtures thereof. The binder or filler may be present from about 50 to about 99% by weight in the pharmaceutical compositions provided herein.

Suitable diluents include, but are not limited to, dicalcium phosphate, calcium sulfate, lactose, sorbitol, sucrose, inositol, cellulose, kaolin, mannitol, sodium chloride, dry starch, and powdered sugar.

Suitable disintegrants include, but are not limited to, agar; bentonite; celluloses, such as methylcellulose and carboxymethylcellulose; wood products; natural sponge; cation-exchange resins; alginic acid; gums, such as guar gum and Vee gum HV; citrus pulp; cross-linked celluloses, such as croscarmellose; cross-linked polymers, such as crospovidone; cross-linked starches; calcium carbonate; microcrystalline cellulose, such as sodium starch glycolate; polacrilin potassium; starches, such as corn starch, potato starch, tapioca starch, and pre-gelatinized starch; clays; aligns; and mixtures thereof. The amount of disintegrant in the pharmaceutical compositions provided herein varies upon the type of formulation, and is readily discernible to those of ordinary skill in the art. The pharmaceutical compositions provided herein may contain from about 0.5 to about 15% or from about 1 to about 5% by weight of a disintegrant.

Suitable lubricants include, but are not limited to, calcium stearate; magnesium stearate; mineral oil; light mineral oil; glycerin; sorbitol; mannitol; glycols, such as glycerol behenate and polyethylene glycol (PEG); stearic acid; sodium lauryl sulfate; talc; hydrogenated vegetable oil, including peanut oil, cottonseed oil, sunflower oil, sesame oil, olive oil, corn oil, and soybean oil; zinc stearate; ethyl oleate; ethyl laureate; agar; starch; lycopodium; silica or silica gels, such as AEROSIL®200 (W. R. Grace Co., Baltimore, MD) and CAB-0-SIL® (Cabot Co. of Boston, MA); and mixtures thereof. The pharmaceutical compositions provided herein may contain about 0.1 to about 5% by weight of a lubricant. Suitable glidants include colloidal silicon dioxide, CAB-0-SIL® (Cabot Co. of Boston, MA), and asbestos-free talc. Coloring agents include any of the approved, certified, water soluble FD&C dyes, and water insoluble FD&C dyes suspended on alumina hydrate, and color lakes and mixtures thereof. A color lake is the combination by adsorption of a water-soluble dye to a hydrous oxide of a heavy metal, resulting in an insoluble form of the dye. Flavoring agents include natural flavors extracted from plants, such as fruits, and synthetic blends of compounds which produce a pleasant taste sensation, such as peppermint and methyl salicylate. Sweetening agents include sucrose, lactose, mannitol, syrups, glycerin, and artificial sweeteners, such as saccharin and aspartame. Suitable emulsifying agents include gelatin, acacia, tragacanth, bentonite, and surfactants, such as polyoxyethylene sorbitan monooleate (TWEEN® 20), polyoxyethylene sorbitan monooleate 80 (TWEEN® 80), and tri-ethanolamine oleate. Suspending and dispersing agents include sodium carboxymethylcellulose, pectin, tragacanth, Veegum, acacia, sodium carbomethylcellulose, hydroxypropyl methylcellulose, and polyvinylpyrolidone. Preservatives include glycerin, methyl and propylparaben, benzoic add, sodium benzoate and alcohol. Wetting agents include propylene glycol monostearate, sorbitan monooleate, diethylene glycol monolaurate, and polyoxyethylene lauryl ether. Solvents include glycerin, sorbitol, ethyl alcohol, and syrup. Examples of non-aqueous liquids utilized in emulsions include mineral oil and cottonseed oil. Organic acids include citric and tartaric acid. Sources of carbon dioxide include sodium bicarbonate and sodium carbonate.

The pharmaceutical compositions may be prepared from the active ingredient in powdered, crystalline, or granular forms, alone or in combination with one or more carriers or excipients described herein, including binders, disintegrants, controlled-release polymers, lubricants, diluents, and/or colorants.

E. METHODS OF USE

In at least one aspect, the present invention includes a method of treating endometriosis comprising administering to a patient a pharmaceutical composition comprising Compound A or a pharmaceutically acceptable salt thereof. In certain embodiments, the method of treating endometriosis comprises administration of a pharmaceutical composition comprising Compound A or a pharmaceutically acceptable salt thereof at a dose of about 150 mg. In some such embodiments, the composition is administered once per day ("QD"). In certain embodiments, the method of treating endometriosis comprises administration of a pharmaceutical composition comprising Compound A or a pharmaceutically acceptable salt thereof at a dose of about 200 mg. In some such embodiments, the composition is administered twice per day ("BID"). In certain embodiments, the method of treating endometriosis comprises administration of a pharmaceutical composition comprising Compound A or a pharmaceutically acceptable salt thereof at a dose of about 300 mg. In some such embodiments, the composition is administered twice per day ("BID"). In certain embodiments, the method of treating endometriosis comprises administration of a pharmaceutical composition comprising Compound A or a pharmaceutically acceptable salt thereof at a dose of about 600 mg. In some such embodiments, the composition is administered once per day ("QD").

In at least one aspect, the present invention includes a method of treating uterine fibroids comprising administering to a patient a pharmaceutical composition comprising Compound A or a pharmaceutically acceptable salt thereof. In certain embodiments, the method of treating uterine fibroids comprises administration of a pharmaceutical composition comprising Compound A or a pharmaceutically acceptable salt thereof at a dose of about 150 mg. In some such embodiments, the composition is administered QD. In certain embodiments, the method of treating uterine fibroids comprises administration of a pharmaceutical composition comprising Compound A or a pharmaceutically acceptable salt thereof at a dose of about 200 mg. In some such embodiments, the composition is administered BID. In certain embodiments, the method of treating uterine fibroids comprises administration of a pharmaceutical composition comprising Compound A or a pharmaceutically acceptable salt thereof at a dose of about 300 mg. In some such embodiments, the composition is administered BID. In certain embodiments, the method of treating uterine fibroids comprises administration of a pharmaceutical composition comprising Compound A or a pharmaceutically acceptable salt thereof at a dose of about 600 mg. In some such embodiments, the composition is administered QD.

In at least one aspect, the present invention includes a method of treating adenomyosis comprising administering to a patient a pharmaceutical composition comprising Compound A or a pharmaceutically acceptable salt thereof. In certain embodiments, the method of treating adenomyosis comprises administration of a pharmaceutical composition comprising Compound A or a pharmaceutically acceptable salt thereof at a dose of about 150 mg. In some such embodiments, the composition is administered once per day ("QD"). In certain embodiments, the method of treating adenomyosis comprises administration of a pharmaceutical composition comprising Compound A or a pharmaceutically acceptable salt thereof at a dose of about 200 mg. In some such embodiments, the composition is administered twice per day ("BID"). In certain embodiments, the method of treating adenomyosis comprises administration of a pharmaceutical composition comprising Compound A or a pharmaceutically acceptable salt thereof at a dose of about 300 mg. In some such embodiments, the composition is administered twice per day ("BID"). In certain embodiments, the method of treating adenomyosis comprises administration of a pharmaceutical composition comprising Compound A or a pharmaceutically acceptable salt thereof at a dose of about 600 mg. In some such embodiments, the composition is administered once per day ("QD").

In certain embodiments, any of the above methods further comprise administering to the subject a hormone to reduce or alleviate potential side effects of Compound A or a pharmaceutically acceptable salt thereof. For example, the method may comprise administration of an estrogen, a progestin, or a combination thereof. Such treatments are commonly referred to as "add-back" therapy. The estrogen is selected from the group consisting of estradiol, ethinyl estradiol, and conjugated estrogens. The progestogen is selected from the group consisting of progesterone, norethindrone acetate, norgestimate, drospirenone, and medroxyprogesterone.

In one embodiment, the estrogen is estradiol and the progestogen is norethindrone acetate.

In some such embodiments, the add-back therapy comprises a progestogen, such as a progestin. In some such embodiments, the add-back therapy comprises an estrogen. In some such embodiments, the add-back therapy comprises a progestin and an estrogen.

The estrogen and/or progestogen can be administered orally, transdermally or intravaginally. Suitable progestogens for use in the add-back therapy include, for example, progesterone, norethindrone, norethindrone acetate, norgestimate, drospirenone, and medroxyprogestogen. Suitable estrogens for use in the add-back therapy include, for example, estradiol, ethinyl estradiol, and conjugated estrogens. Combined oral formulations containing an estrogen and a progestogen are known in the art and include, for example, Activella®, Angeliq®, FemHRT®, Jenteli™, Mimvey™, Prefest™, Premphase®, and Prempro®.

In certain embodiments, the estrogen is estradiol, ethinyl estradiol, or a conjugated estrogen. In some such embodiments, the estrogen is estradiol. In some such embodiments, the estradiol is administered once a day. In some such embodiments, the dose of estradiol is 0.5 mg. In some such embodiments, the dose of estradiol is 1.0 mg. In some such embodiments, the estrogen is ethinyl estradiol. In some such embodiments, the ethinyl estradiol is administered once a day. In some such embodiments, the dose of ethinyl estradiol is 2.5 mcg. In other such embodiments, the dose of ethinyl estradiol is 5.0 mcg. In some such embodiments, the estrogen is a conjugated estrogen. In some such embodiments, the conjugated estrogen is administered once a day. In some such embodiments, the dose of conjugated estrogen is 0.3 mg. In other such embodiments, the dose of conjugated estrogen is 0.45 mg or 0.625 mg.

In certain embodiments, the progestogen is progesterone, norethindrone, norethindrone acetate, norgestimate, medroxyprogesterone, or drospirenone. In some such embodiments, the progestogen is oral progesterone. In some such embodiments, the oral progesterone is used cyclically (for the last 12 days of the 28-30 day cycle). In some such embodiments, the dose of the oral progesterone is 100 or 200 mg. In some such embodiments, the progestogen is norethindrone or norethindrone acetate. In some such embodiments, the norethindrone or norethindrone acetate is administered once a day. In some such embodiments, the dose of norethindrone or norethindrone acetate is 0.1 mg. In some such embodiments, the dose of norethindrone or norethindrone acetate is 0.5 mg. In some such embodiments, the dose of norethindrone or norethindrone acetate is 1.0 mg. In some such embodiments, the progestogen is norgestimate. In some such embodiments, the norgestimate is administered once a day. In some such embodiments, the dose of norgestimate is 0.09 mg. In some such embodiments, the progestogen is medroxyprogesterone. In some such embodiments, the medroxyprogesterone is administered once a day. In some such embodiments, the dose of medroxyprogesterone is 1.5 mg. In some such embodiments, the dose of medroxyprogesterone is 2.5 mg or 5 mg. In some such embodiments, the progestogen is drospirenone. In some such embodiments, the drospirenone is administered once a day. In some such embodiments, the dose of drospirenone is 0.25 mg. In some such embodiments, the dose of drospirenone is 0.5 mg.

In certain embodiments, the add-back therapy comprises a norethisterone prodrug, such as norethindrone acetate. In some such embodiments, the add-back therapy further comprises estradiol. Thus, in some such embodiments, the add-back therapy comprises estradiol and norethindrone acetate. In some such embodiments, estradiol and norethindrone acetate are administered orally once per day. In some such embodiments, estradiol is administered in an amount of about 0.5 mg and norethindrone acetate is administered in an amount of about 0.1 mg per day. In other such embodiments, estradiol is administered in an amount of about 1.0 mg and norethindrone acetate is administered in an amount of about 0.5 mg per day. Alternatively, in certain embodiments, estradiol is administered continuously and norethindrone acetate is administered once per day during the last 12-14 days of a menstrual cycle.

In certain embodiments, the dose of Compound A or a pharmaceutically acceptable salt thereof is administered twice a day. In some such embodiments, add-back therapy is administered once a day. The administration of Compound A or a pharmaceutically acceptable salt thereof may be prior to, immediately prior to, during, immediately subsequent to or subsequent to the administration of the add-back therapy.

In certain embodiments, a dose of Compound A or pharmaceutically acceptable salt thereof (e.g., 300 mg) is administered in the morning with add-back therapy, such as a combination of an estrogen and a progestogen (e.g., estradiol and norethindrone acetate) and a dose of Compound A or pharmaceutically acceptable salt thereof (e.g., 300 mg) is administered in the evening without add-back therapy.

In certain embodiments, Compound A or a pharmaceutically acceptable salt thereof is co-packaged with the add-back therapy. For example, a blister pack may contain a dose of Compound A or a pharmaceutically acceptable salt thereof and a dose of the add-back therapy.

The pharmaceutical compositions, methods, and uses described herein will be better understood by reference to the following exemplary embodiments and examples, which are included as an illustration of and not a limitation upon the scope of the invention.

F. EXAMPLES

The following Examples demonstrate certain challenges encountered during formulation development and describe formulations that overcome those challenges.

Example 1: Gel Formation by Compound A Monosodium Salt

To estimate the solubility of Compound A in water, various amounts of Compound A sodium salt were added to a fixed volume of 1.5 mL and equilibrated at 37° C.; solutions were assayed for Compound A concentration.

Figure 2:
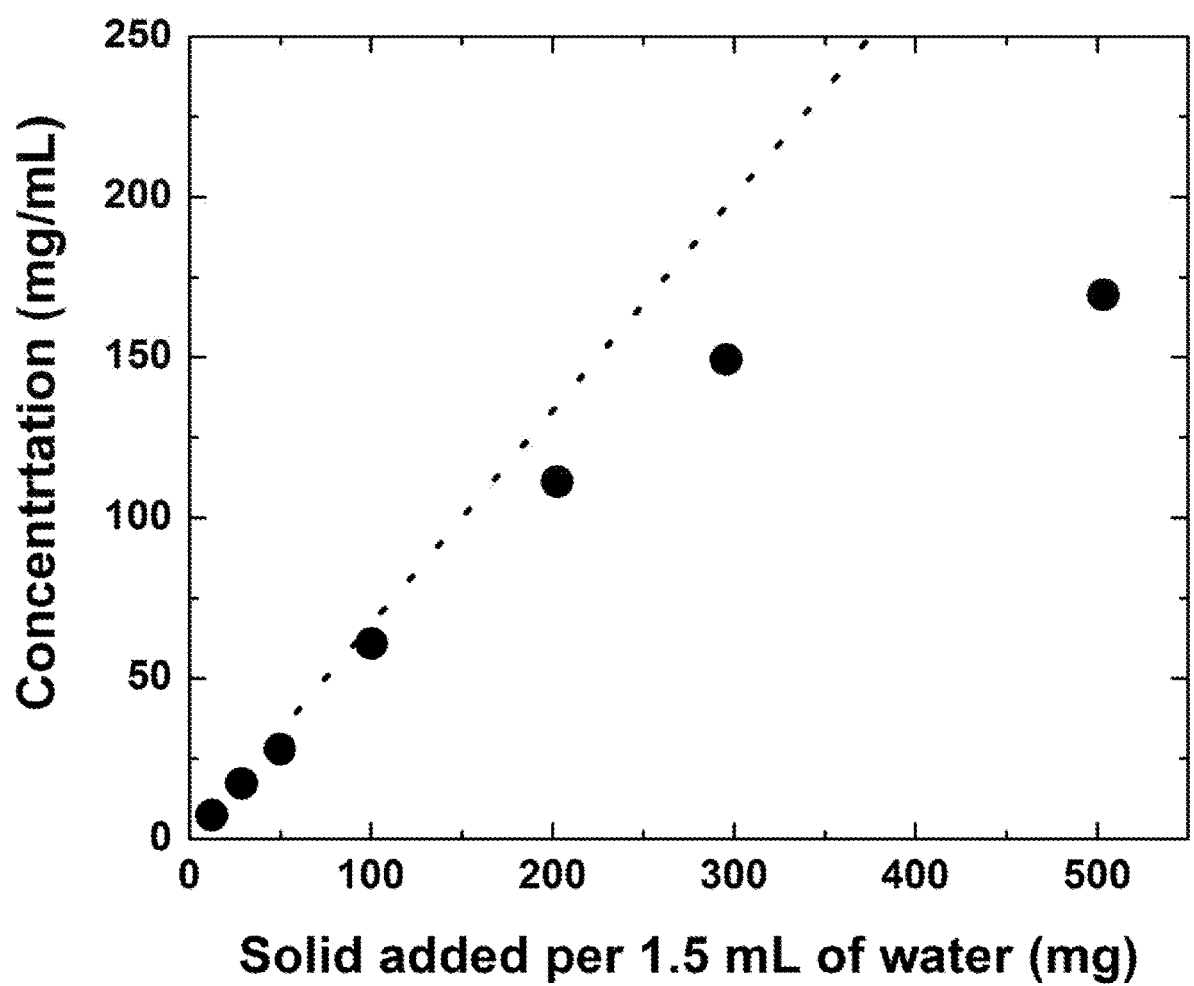
FIG. 2 is a plot showing apparent solubility of Compound A in water.

Table 2 lists the raw data and observations of the experiment, and FIG. 2 shows the concentration as a function of the amount of Compound A solid added. The dotted line in FIG. 2 is the theoretical concentration based on the weights of the solids added and the volume of water. As shown in FIG. 2, the concentration of Compound A agrees with the simple calculation up to 100 mg solid/1.5 mL. Deviation of the concentrations from the theoretical line is due to the volume expansion upon dissolution of large amount of solutes. Beyond that, the concentrations deviate from the theoretical line, but the solution is still clear and no visible gelling was observed. When more than 500 mg of Compound A solid was added, visible gelling was observed, therefore, concentrations were not determined.

TABLE 2

Raw Data of Compound A Solubility Experiment in Water at 37° C.

| Amount (mg) added to 1.5 mL | Measured Concentration (mg/mL) | Observation | Final pH |
|---|---|---|---|
| 0 | 0 | N/A | ~6 |
| 12.2 | 7.45 | Clear solution | 9.66 |
| 28.7 | 17.3 | Clear solution | 9.96 |
| 49.8 | 28.0 | Clear solution | 10.10 |
| 100.4 | 60.8 | Clear solution | 10.16 |
| 202.5 | 111 | Clear solution | 10.18 |
| 295.6 | 149 | Clear solution | 10.20 |
| 503.2 | 170 | Clear solution | 10.17 |
| 700.9 | N/A | Gel formation | N/A |
| 990.0 | N/A | Gel formation | N/A |

Further experiments revealed that if the percent of Compound A or a salt thereof in a tablet formulation is greater than 10 percent (and in the absence of an appropriate anti-gelling agent), incomplete dissolution occurs—Compound A was present as an insoluble precipitate. Therefore, a formulation of Compound A sodium salt was evaluated, at about 10% drug loading, where minimal gelling was observed.

Example 2: In Vitro Release in the Absence of an Anti-Gelling Agent

An immediate release formulation was prepared without an anti-gelling agent. All components, except magnesium stearate, were blended in a high-shear granulator and granulated with neat, de-ionized water. The granules were tray-dried at 40° C. and passed through a #20 US Standard sieve and lubed with magnesium stearate. Compound A referenced in the table below is the Compound A sodium salt.

Composition of Formulation without Anti-Gelling Agent

| Ingredient | Quantity (mg/Tablet) |
|---|---|
| Compound A, sodium salt | 207.3 |
| Mannitol | 304.0 |
| Pregelatinized Starch | 59.1 |
| Povidone K 29/32 | 18.4 |
| Magnesium stearate | 11.2 |

The dissolution profile for the uncoated tablets in pH 1.2 medium is shown in Table 3.

TABLE 3

(RC2i; 200 mg; Lot# 170123A-01 (GLIMS# 39746))

| Time (min) | Mean % (Std Dev) |
|---|---|
| 15 | 15 (0.5) |
| 30 | 31 (0.5) |
| 45 | 45 (0.6) |
| 60 | 57 (0.7) |

Example 3: Formulations Having an Anti-Gelling Agent

Table 4 presents additional non-limiting examples of components of the disclosed formulations and their percentage by weight (w/w) of the final coated tablet. Compound A referenced in the table below is the Compound A sodium salt and the corresponding amount (mg/tablet) and weight percent is provided based on that salt form.

TABLE 4

Composition of Exemplary Formulations.

| Ingredient | Function | F1 (150 mg) Quantity (mg/Tablet) | F1 (150 mg) %ᵃ (w/w) | F2 (50 mg) Quantity (mg/Tablet) | F2 (50 mg) %ᵃ (w/w) | F3 (150 mg) Quantity (mg/Tablet) | F3 (150 mg) %ᵃ (w/w) |
|---|---|---|---|---|---|---|---|
| Compound A, sodium salt | Drug Substance | 155.5 | 25.2 | 51.8 | 33.5 | 155.5 | 33.5 |
| Mannitol, USP | Filler | 271.0 | 43.9 | 50.2 | 32.5 | 150.5 | 32.5 |
| Corn Starch, NF | Filler | 68.2 | 11.0 | 16.0 | 10.4 | 48.0 | 10.4 |
| Pregelatinized Starch | Filler/Binder | — | — | — | — | — | — |
| Povidone K 29/32, USP | Binder | 21.3 | 3.4 | 5.0 | 3.2 | 15.0 | 3.2 |
| Sodium carbonate monohydrate, NF | Anti-gelling Agent/pH Modifying agent | 75.0 | 12.1 | 25.0 | 16.2 | 75.0 | 16.2 |
| Silicon Dioxide, NF | Glidant | 3.0 | 0.5 | — | — | — | — |
| Magnesium stearate, NF | Lubricant | 6.0 | 1.0 | 2.0 | 1.3 | 6.0 | 1.3 |
| Uncoated tablet weight | | 600.0 | — | 150.0 | — | 450.0 | — |
| Opadry ® | Film Coat | 18.0 | 2.9 | 4.5 | 2.9 | 13.5 | 2.9 |
| Opadry ® II | Film Coat | — | — | — | — | — | — |
| Eudragit L 30 D-55 + plasticizer + glidant | Enteric Coat | — | — | — | — | — | — |
| Coated tablet weight | | 618.0 | 100 | 154.5 | 100 | 463.5 | 100 |

| Ingredient | Function | F4 (100 mg) Quantity (mg/Tablet) | F4 (100 mg) %ᵃ (w/w) | F5 (150 mg) Quantity (mg/Tablet) | F5 (150 mg) %ᵃ (w/w) |
|---|---|---|---|---|---|
| Compound A, sodium salt | Drug Substance | 103.7 | 33.6 | 155.5 | 33.5 |
| Mannitol, USP | Filler | 100.0 | 32.4 | 150.0 | 32.4 |
| Corn Starch, NF | Filler | — | — | — | — |
| Pregelatinized Starch | Filler/Binder | 29.5 | 9.5 | 44.3 | 9.6 |
| Povidone K 29/32, USP | Binder | 9.2 | 3.0 | 13.8 | 3.0 |
| Sodium carbonate monohydrate, NF | Anti-gelling Agent/pH Modifying agent | 52.0 | 16.8 | 78.0 | 16.8 |
| Silicon Dioxide, NF | Glidant | — | — | — | — |
| Magnesium stearate, NF | Lubricant | 5.6 | 1.8 | 8.4 | 1.8 |
| Uncoated tablet weight | | 300.0 | — | 450.0 | — |
| Opadry ® | Film Coat | 9.0 | 2.9 | 13.5 | 2.9 |
| Opadry ® II | Film Coat | — | — | — | — |
| Eudragit L 30 D-55 + plasticizer + glidant | Enteric Coat | — | — | — | — |
| Coated tablet weight | | 309.0 | 100 | 463.5 | 100 |

TABLE 4-continued

Composition of Exemplary Formulations.

| Ingredient | Function | F6 (150 mg) Quantity (mg/Tablet) | %$^a$ (w/w) | F7 (200 mg) Quantity (mg/Tablet) | %$^a$ (w/w) | F7DR (200 mg) Quantity (mg/Tablet) | %$^a$ (w/w) | F8 (300 mg) Quantity (mg/Tablet) | %$^a$ (w/w) |
|---|---|---|---|---|---|---|---|---|---|
| Compound A, sodium salt | Drug Substance | 155.5 | 33.5 | 207.4 | 33.6 | 207.4 | 32.0 | 310.9 | 33.5 |
| Mannitol, USP | Filler | 150.0$^b$ | 32.4 | 199.9$^b$ | 32.3 | 199.9$^b$ | 30.8 | 299.9$^b$ | 32.4 |
| Corn Starch, NF | Filler | — | — | — | — | — | — | — | — |
| Pregelatinized Starch | Filler/Binder | 44.3 | 9.6 | 59.1 | 9.6 | 59.1 | 9.1 | 88.7 | 9.6 |
| Povidone K 29/32, USP | Binder | 13.8 | 3.0 | 18.5 | 3.0 | 18.5 | 2.9 | 27.7 | 3.0 |
| Sodium carbonate monohydrate, NF | Anti-gelling Agent/pH Modifying agent | 78.0 | 16.8 | 104.0 | 16.8 | 104.0 | 16.0 | 156.0 | 16.8 |
| Silicon Dioxide, NF | Glidant | — | — | — | — | — | — | — | — |
| Magnesium stearate, NF | Lubricant | 8.4 | 1.8 | 11.2 | 1.8 | 11.2 | 1.7 | 16.8 | 1.8 |
| Uncoated tablet weight | | 450.0 | — | 600.1 | — | 600.1 | — | 900.0 | — |
| Opadry ® | Film Coat | — | — | — | — | — | — | — | — |
| Opadry ® II | Film Coat | 13.5 | 2.9 | 18.0 | 2.9 | — | — | 27.0 | 2.9 |
| Eudragit L 30 D-55 + plasticizer + glidant | Enteric Coat | — | — | — | — | 48.0 | 7.4 | — | — |
| Coated tablet weight | | 463.5 | 100 | 618.1 | 100 | 648.1 | 100 | 927.0 | 100 |

| Ingredient | Function | F9 (150 mg) Quantity (mg/Tablet) | %$^a$ (w/w) | F10 (200 mg) Quantity (mg/Tablet) | %$^a$ (w/w) | F11 (200 mg) Quantity (mg/Tablet) | %$^a$ (w/w) |
|---|---|---|---|---|---|---|---|
| Compound A, sodium salt | Drug Substance | 155.2 | 33.2 | 207.4 | 33.2 | 207.4 | 50.3 |
| Mannitol, USP | Filler | 150.3 | 32.1 | 200.3 | 32.1 | 74.2 | 18.0 |
| Corn Starch, NF | Filler | — | — | — | — | — | — |
| Pregelatinized Starch | Filler/Binder | 44.3 | 9.5 | 59.1 | 9.5 | — | — |
| Povidone K 29/32, USP | Binder | 13.8 | 2.9 | 18.4 | 2.9 | 12.0 | 2.9 |
| Sodium carbonate monohydrate, NF | Anti-gelling Agent/pH Modifying agent | 78.0 | 16.7 | 104.0 | 16.7 | 100.0 | 24.3 |
| Silicon Dioxide, NF | Glidant | — | — | — | — | — | — |
| Magnesium stearate, NF | Lubricant | 8.4 | 1.8 | 11.2 | 1.8 | 6.4 | 1.6 |
| Uncoated tablet weight | | 450.0 | — | 600.0 | — | 400.0 | — |
| Opadry ® | Film Coat | — | — | — | — | — | — |
| Opadry ® II | Film Coat | 18.0 | 3.8 | 24.0 | 3.8 | 12.0 | 29 |
| Eudragit L 30 D-55 + plasticizer + glidant | Enteric Coat | — | — | — | — | — | — |
| Coated tablet weight | | 468.0 | 100 | 624.0 | 100 | 412.0 | 100 |

$^a$Percents given based on the coated tablet weight. Total percentage may not be 100% due to rounding.
$^b$Mannitol (12.3%) added extragranular.

3.1. Preparation.

Figure 3:
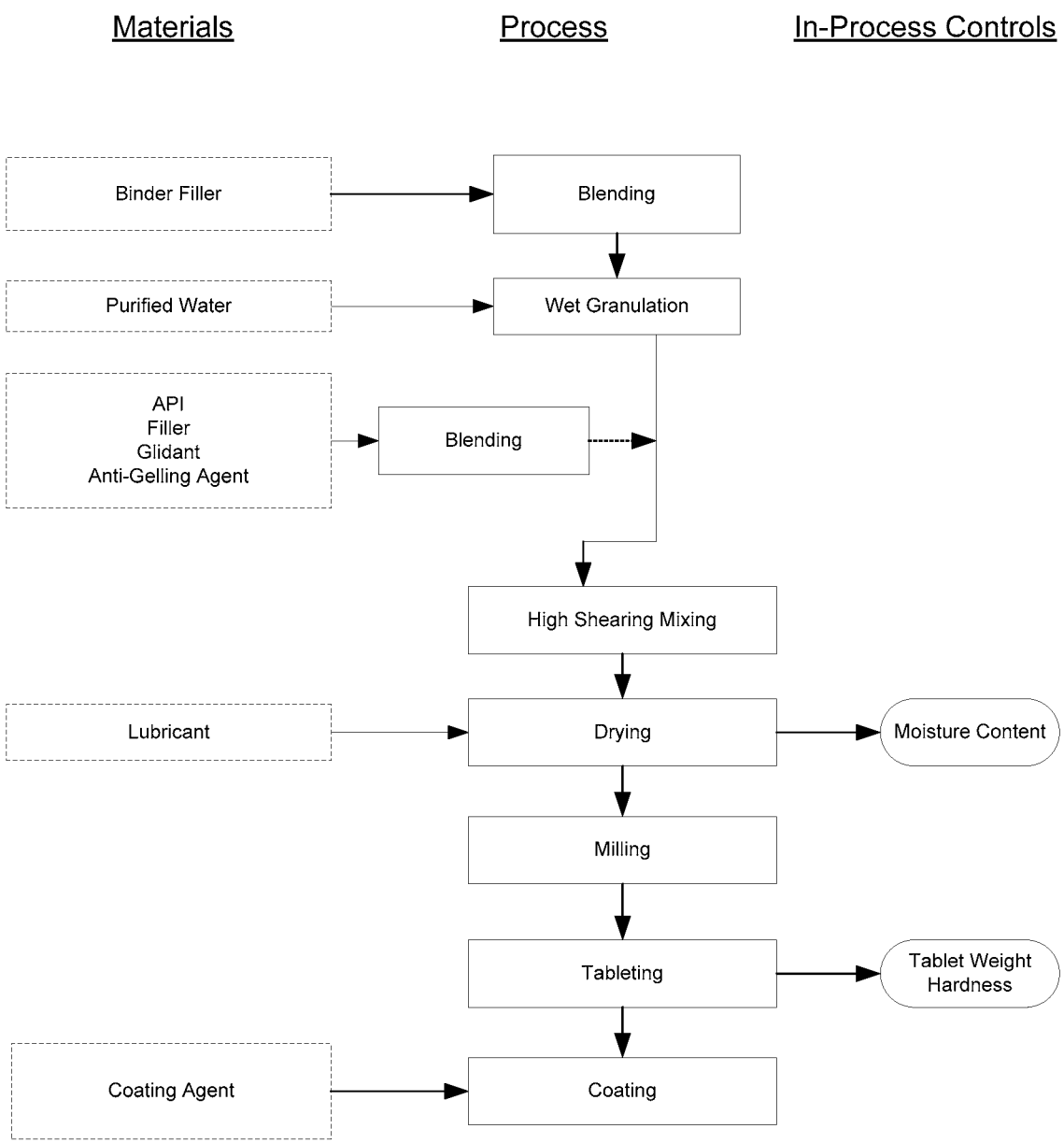
FIG. 3 is a two-step wet granulation process flow diagram.

F1 was prepared using a two-step granulation process. The manufacturing process flow diagram is presented in FIG. 3. In this process, the binder and a portion of the filler were added to the single pot processor bowl. Sodium carbonate, the remaining filler, Compound A, and colloidal silicon dioxide are blended in an IBC. In the first granulation step, the filler/binder blend in the SPP bowl was granulated with water. In the second granulation step, the Compound A blend was added to the SPP bowl and granulated by mixing for a short time. The granulation was then dried in the SPP bowl using vacuum and swing mode. The dried granulation was milled using a Comil into another IBC. The lubricant magnesium stearate was added to the granules and blended. The granules were compressed into 600 mg tablet for 150 mg dose strength.

Formulations F2 and F3 were prepared using blending, fluid bed granulation, milling, tableting, and tablet coating.

Formulations F4-F11 were prepared using blending, roller compaction and milling, tableting, and tablet coating, generally as shown in FIG. 1. Formulations F4 and F5 were developed with a target drug loading of ~35% Compound A to obtain uncoated tablet weights of 300 and 450 mg for 100 and 150 mg dose strengths, respectively.

A subset of the immediate release tablets were coated with an enteric coating to provide delayed release tablets (F7DR) (DR1). The tablets were coated with an enteric coating comprising Eudragit L 30 D-55, Plasacryl T20, and triethyl citrate. Typical coating parameters were maintained during this process.

3.2. In Vitro Dissolution Profile for Formulations F1 & F5 in pH 1.2 Buffer

Multiple batches of the formulation with 25% drug loading were manufactured. The dissolution profile for F1 tablets in pH 1.2 medium is shown in Table 5.

TABLE 5

| Time | Mean % Dissolution (SD) | |
| --- | --- | --- |
| (min) | Batch 1 | Batch 2 |
| 15 | 54 (3.4) | 46 (1.7) |
| 30 | 99 (1.1) | 87 (0.3) |
| 45 | 102 (1) | 99 (1.9) |
| 60 | 104 (0.7) | 101 (1.5) |

The dissolution profile for F5 tablets in pH 1.2 medium is shown in Table 6.

TABLE 6

| Time (min) | Mean % Dissolution |
| --- | --- |
| 15 | 20 |
| 30 | 54 |
| 45 | 80 |
| 60 | 95 |

3.3. In Vitro Dissolution Profile after Storage for Up to 24 Months

Figure 4:
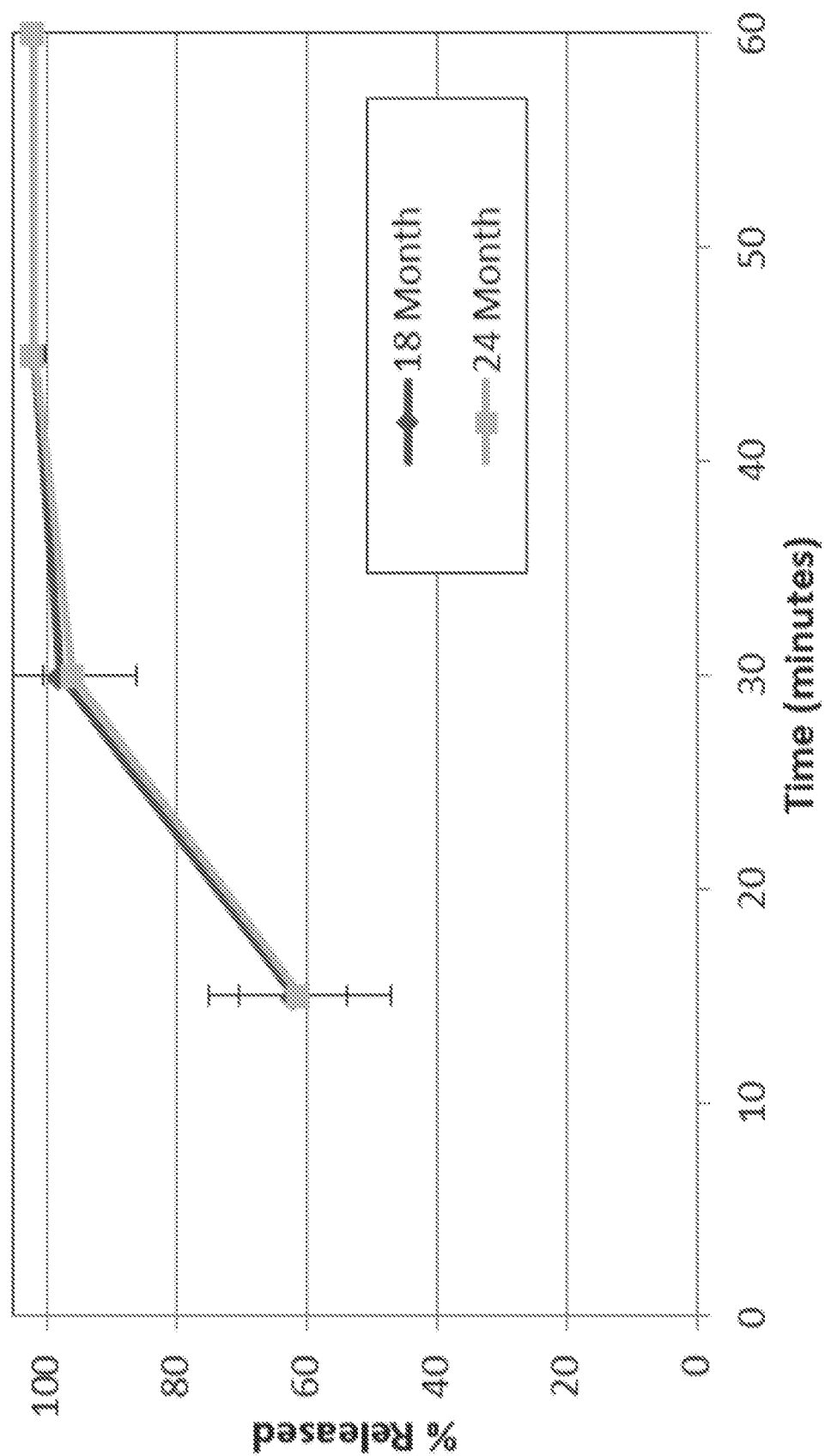
FIG. 4 is a graph showing an in vitro dissolution profile for Formulation F5 after storage for 18 or 24 months.
Figure 5:
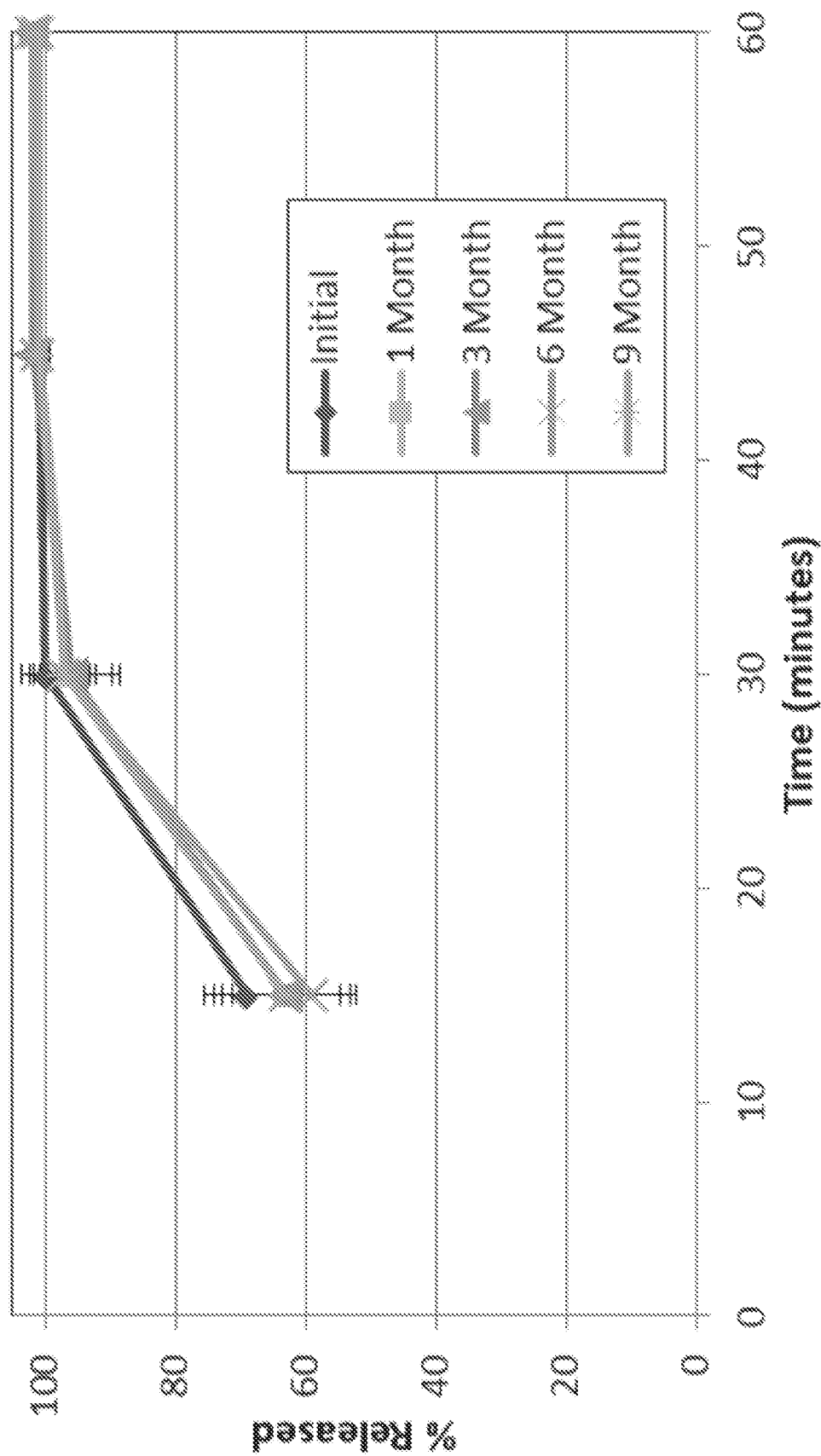
FIG. 5 is a graph showing an in vitro dissolution profile for Formulation F6 after storage for 1, 3, 6, or 9 months.
Figure 6:
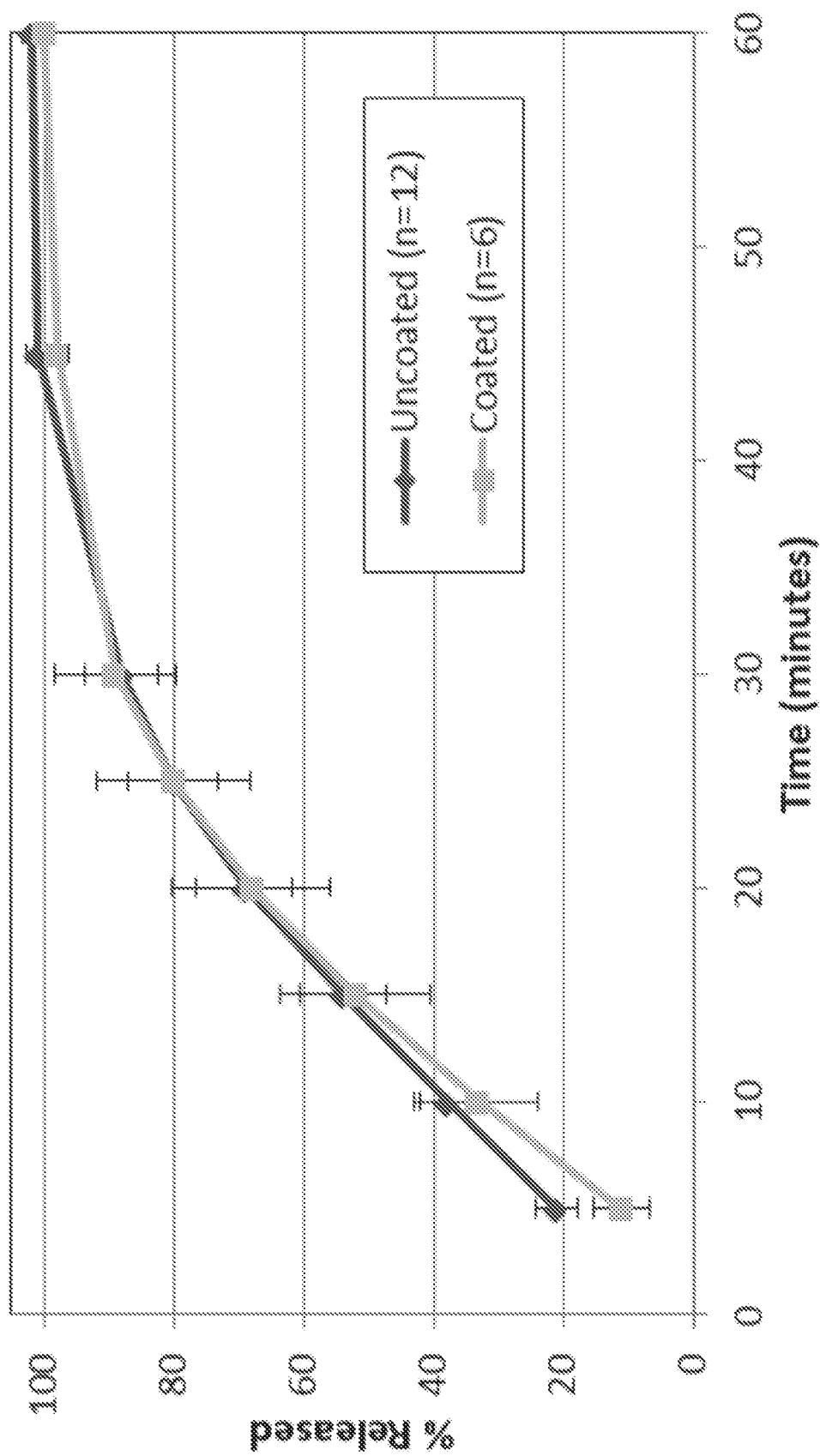
FIG. 6 is a graph showing an in vitro dissolution profile for Formulation F10 (uncoated and film-coated tablets).

Formulations F5, F6, and F10 were tested for dissolution using USP apparatus II in 900 mL of sodium phosphate, pH 6.8, at 37° C. and paddle speed of 50 rpm. Formulations F5, F6, and F10 all showed similar dissolution profiles both tested initially and upon storage for up to 24 months. The dissolution profiles of Formulation F5 tablets at 18 and 24 months are shown in FIG. 4. The stability dissolution profile of Formulation F7 tablets is shown in FIG. 5. The dissolution profile of uncoated and film coated Formulation F10 tablets is shown in FIG. 6.

3.4. Pharmacokinetic Profile for 150 mg, 200 mg, & 300 mg Dosage.

3.4.1. Pharmacokinetics of F3 and F5 (150 mg)

A study was conducted to explore the bioavailability of single doses of 2 IR tablet formulations (F3 and F5) at a 150 mg dose under fasting conditions. The pharmacokinetic parameters are shown in Table 7. Data for pharmacokinetic parameters are presented as the mean±SD.

TABLE 7

| Pharmacokinetic Parameters (units) | Formulations | |
| --- | --- | --- |
| | F3 150 mg IR tablet (N = 23) | F5 150 mg IR tablet (N = 23) |
| $C_{max}$ (ng/mL) | 523 ± 247 | 510 ± 225 |
| $T_{max}$ (hr) | 1.07 ± 0.35 | 1.12 ± 0.42 |
| $AUC_t$ (ng · hr/mL) | 1263 ± 560 | 1273 ± 520 |
| $AUC_\infty$ (ng · hr/mL) | 1271 ± 560 | 1281 ± 520 |
| $t_{1/2}$ (hr) | 2.03 ± 0.41 | 2.21 ± 0.60 |

3.4.2. Pharmacokinetics of F4 and F7 (200 mg)

A study was conducted to compare the relative bioavailability of single doses of one 200 mg IR tablet of Formulation F7 with that of two 100 mg IR tablets of Formulation F4 under fasting conditions. Pharmacokinetic assessments showed that Formulation F7 (200 mg IR tablet) was bioequivalent to Formulation F4 (2×100 mg IR), with respect to maximum concentration (Cmax) and area under the curve (AUC), with 90% CI that fell within the limits of 0.80 to 1.25. The pharmacokinetic parameters are shown in Table 8. Data for pharmacokinetic parameters are presented as the mean SD.

TABLE 8

| Pharmacokinetic Parameters (units) | Formulations | |
| --- | --- | --- |
| | F4 2 × 100 mg IR tablets (N = 23) | F7 200 mg IR tablet (N = 23) |
| $C_{max}$ (ng/mL) | 879 ± 401 | 845 ± 329 |
| $T_{max}$ (hr) | 1.1 ± 0.4 | 1.1 ± 0.3 |
| $AUC_t$ (ng · hr/mL) | 2384 ± 916 | 2211 ± 853 |
| $AUC_\infty$ (ng · hr/mL) | 2391 ± 917 | 2217 ± 854 |
| $t_{1/2}$ (hr) | 3.86 ± 0.70 | 3.91 ± 0.48 |

3.4.3. Pharmacokinetics of F4 and F10 (200 mg)

A further study was conducted to explore the bioavailability a single dose of one 200 mg IR tablet of Formulation F10 with that of two 100 mg IR tablets of Formulation F4 under fasting conditions. The pharmacokinetic parameters are shown in Table 9. Data for pharmacokinetic parameters are presented as the mean±SD.

TABLE 9

| Pharmacokinetic Parameters (units) | Formulations | |
| --- | --- | --- |
| | F4 2 × 100 mg IR tablets (N = 54) | F10 200 mg IR tablet (N = 54) |
| $C_{max}$ (ng/mL) | 744 ± 353 (47) | 738 ± 419 (57) |
| $T_{max}$ (h) | 1.0 (0.5-3.0) | 1.0 (0.5-3.0) |
| $t_{1/2}$ (h) | 5.91 ± 2.82 | 6.20 ± 2.93 |
| $AUC_t$ (ng · h/mL) | 1890 ± 852 (45) | 1910 ± 960 (50) |
| $AUC_\infty$ (ng · h/mL) | 1900 ± 853 (45) | 1920 ± 961 (50) |

3.4.4. Pharmacokinetics of F5 (300 mg)

A study was conducted to explore the bioavailability of a single dose of two 150 mg IR tablets of Formulation F5 under fasting conditions. The pharmacokinetic parameters are shown in Table 10. Data for pharmacokinetic parameters are presented as the mean SD.

TABLE 10

| Pharmacokinetic Parameters (units) | F5 2 × 150 mg IR tablet (N = 10) |
| --- | --- |
| $C_{max}$ (ng/mL) | 1378 ± 487 |
| $T_{max}$ (hr) | 1.6 ± 0.6 |
| $AUC_t$ (ng · hr/mL) | 3732 ± 1356 |
| $AUC_\infty$ (ng · hr/mL) | 3772 ± 1368 |

3.4.5. Pharmacokinetics of F7 & F7DR (200 mg)

A clinical study was conducted to compare the in vivo performance of F7 and F7DR. Additionally, the study assessed the potential effects of a high-fat meal on the pharmacokinetics of F7DR. Adult premenopausal healthy female subjects were administered a single dose of F7DR under fasting conditions, a single dose of F7DR 30 minutes after consuming a high-fat meal, or a single dose of F7 under fasting conditions.

A high-fat meal reduced the concentrations of the F7DR tablet formulation. A delay in absorption was observed for the F7DR tablet formulation, regardless of the meal conditions. Food reduced the Cmax and AUC of F7DR. The delay of absorption was longer for under fed conditions.

The pharmacokinetic parameters are shown in Table 11. Data for Cmax and AUC are presented as the mean (% CV); data for Tmax are presented as median (min–max); and data for t1/2 are presented as harmonic mean (pseudo CV).

TABLE 11

(Study M14-313)

| Pharmacokinetic Parameters (units) | Regimens | | |
|---|---|---|---|
| | F7-fasted 200 mg IR tablet (N = 24) | F7DR-fasted 200 mg eIR tablet (N = 11) | F7DR-fed 200 mg eIR tablet (N = 11) |
| $C_{max}$ (ng/mL) | 850 (34) | 977 (63) | 332 (51) |
| $T_{max}$ (hr) | 1.0 (0.75-1.5) | 3.0 (1.5-6.0) | 7.0 (4.0-12.0) |
| $AUC_t$ (ng · hr/mL) | 2106 (43) | 2253 (53) | 1241 (46) |
| $AUC_\infty$ (ng · hr/mL) | 2115 (43) | 2262 (53) | 1250 (46) |
| $t_{1/2}$ (hr) | 4.4 (33) | 3.80 (34) | 3.01 (26) | endometriosis-associated pain. Baseline characteristics, including the subjects' endometriosis-associated pain at study entry, were comparable across treatment groups.

Treatment groups were: (a) one F5 tablet once daily (i.e., 150 mg QD) and (b) two F4 tablets twice daily (i.e., 200 mg BID). Blood samples were collected during the monthly clinic visits to measure hormone concentrations. Over 800 female subjects across 151 sites in North America were randomized into the study in a 3:2:2 ratio to placebo, 150 mg QD, or 200 mg BID, respectively.

A dose-dependent suppression of estradiol was observed in the treatment groups, compared with placebo during the treatment period. For the placebo group, the median estradiol levels at their monthly visits were between 70.0 and 91.6 pg/mL, with 2% to 4% of women with estradiol concentrations <20 pg/mL. For the 150 mg QD group, the median estradiol levels at their monthly visits were between 36.8 and 45.7 pg/mL, with 15% to 24% of women with estradiol concentrations <20 pg/mL. For the 200 mg BID group, the median estradiol levels at their monthly visits were at the limit of quantification (12.4 pg/mL), with 71% to 81% of women with estradiol concentrations <20 pg/mL.

TABLE 12

Estradiol Serum Concentrations

| Treatment/Parameter | Day 1 (Predose) | Month 1 | Month 2 | Month 3 | Month 4 | Month 5 | Month 6 |
|---|---|---|---|---|---|---|---|
| Placebo | | | | | | | |
| N | 366 | 342 | 329 | 310 | 300 | 288 | 223 |
| Median | 48.6 | 70.0 | 83.4 | 88.6 | 77.7 | 82.9 | 91.6 |
| (Mean ± SD) | (66.5 ± 56.3) | (91.8 ± 74.8) | (104.4 ± 79.4) | (110.6 ± 89.7) | (107.1 ± 86.8) | (107.3 ± 82.7) | (111.7 ± 79.9) |
| % subjects <20 pg/mL | 6.3 | 3.8 | 4.0 | 1.9 | 2.7 | 3.8 | 2.7 |
| % subjects 20-50 pg/mL | 45.6 | 33.6 | 23.4 | 26.1 | 25.7 | 23.6 | 21.1 |
| % subjects >50 pg/mL | 48.1 | 62.6 | 72.6 | 71.9 | 71.7 | 72.6 | 76.2 |
| 150 mg QD | | | | | | | |
| N | 244 | 229 | 217 | 213 | 198 | 195 | 165 |
| Median | 45.7 | 36.8 | 39.2 | 41.0 | 41.2 | 41.5 | 45.7 |
| (Mean ± SD) | (70.9 ± 70.0) | (56.7 ± 58.5) | (60.7 ± 59.0) | (65.8 ± 66.9) | (66.7 ± 82.4) | (70.1 ± 72.5) | (75.4 ± 77.6) |
| % subjects <20 pg/mL | 9.4 | 23.6 | 19.4 | 21.1 | 20.7 | 15.4 | 15.2 |
| % subjects 20-50 pg/mL | 45.5 | 43.7 | 44.7 | 37.1 | 38.9 | 41.5 | 41.2 |
| % subjects >50 pg/mL | 45.1 | 32.8 | 35.9 | 41.8 | 40.4 | 43.1 | 43.6 |
| 200 mg BID | | | | | | | |
| N | 246 | 222 | 208 | 197 | 188 | 181 | 150 |
| Median | 46.5 | 12.4 | 12.4 | 12.4 | 12.4 | 12.4 | 12.4 |
| (Mean ± SD) | (77.5 ± 84.9) | (25.0 ± 38.2) | (25.5 ± 44.7) | (27.4 ± 42.9) | (22.8 ± 32.4) | (25.3 ± 35.3) | (31.1 ± 50.8) |
| % subjects <20 pg/mL | 8.1 | 80.6 | 80.8 | 76.1 | 78.2 | 75.1 | 70.7 |
| % subjects 20-50 pg/mL | 45.5 | 8.6 | 11.1 | 13.7 | 14.4 | 14.9 | 15.3 |
| % subjects >50 pg/mL | 46.3 | 10.8 | 8.2 | 10.2 | 7.4 | 9.9 | 14.0 |

Example 4: Estradiol Concentrations Following Treatment with F4 or F5

A further study was conducted in premenopausal women with moderate to severe endometriosis-associated pain. The women enrolled in this study were representative of the general population of women with moderate to severe Example 5: Estradiol Concentrations Following Treatment with F4 or F5

Another study was conducted in premenopausal women with moderate to severe endometriosis-associated pain. The women enrolled in this study were representative of the general population of women with moderate to severe endometriosis-associated pain. Baseline characteristics, including the subjects' endometriosis-associated pain at study entry, were comparable across treatment groups.

Treatment groups were: (a) one F5 tablet once daily (i.e., 150 mg QD) and (b) two F4 tablets twice daily (i.e., 200 mg BID). Blood samples were collected during the monthly clinic visits to measure hormone concentrations. Over 800 female subjects across 187 sites in North America, South America, Europe, Africa, and Australia were randomized into the study in a 3:2:2 ratio to placebo, 150 mg QD, or 200 mg BID, respectively.

A dose-dependent suppression of estradiol was observed in the treatment groups, compared with placebo during the treatment period. For the placebo group, the median estradiol levels at their monthly visits were between 70.7 and 105 pg/mL with 4% to 6% of women with estradiol concentrations <20 pg/mL. For the 150 mg QD dose, the median estradiol levels at their monthly visits were between 37.2 and 55.8 pg/mL, with 14% to 22% of women with estradiol concentrations <20 pg/mL. For the 200 mg BID dose, the median estradiol levels at their monthly visits were between 8.43 and 13.1 pg/mL, with 62% to 77% of women with estradiol concentrations <20 pg/mL.

TABLE 14

Composition of Formulation F12

| Ingredient | Quantity (mg/Tablet) | |
|---|---|---|
| | F12 | F12A |
| Compound A, sodium salt | 155.5 | 153.1 |
| Microcrystalline Cellulose | 150.5 | 148.2 |
| Corn Starch | 48.0 | 47.3 |
| Povidone K 29/32 | 15.0 | 14.8 |
| Sodium Carbonate, monohydrate | 75.0 | 73.8 |
| Magnesium stearate | 6.0 | 5.9 |
| Sodium dodecyl sulfate | — | 6.8 |

Formulation F12A was prepared by combining 6.3 g Formulation F12 and 97.3 mg sodium dodecyl sulfate (1.5% w/w) in a bottle and rolling the bottle by hand to blend.

An in vitro dissolution study was conducted. The release of Compound A was monitored using USP apparatus II in 900 mL of pH 6.8 buffer, at 37° C. and paddle speed of 50 rpm. The dissolution results are presented in Table 15:

TABLE 13

Estradiol Serum Concentrations

| Treatment/Parameter | Day 1 (Predose) | Month 1 | Month 2 | Month 3 | Month 4 | Month 5 | Month 6 |
|---|---|---|---|---|---|---|---|
| Placebo | | | | | | | |
| N | 324 | 312 | 293 | 272 | 261 | 256 | 232 |
| Median | 58.1 | 70.7 | 85.2 | 84.9 | 77.8 | 80.2 | 105 |
| (Mean ± SD) | (91.4 ± 81.5) | (99.6 ± 87.1) | (105 ± 79.1) | (106 ± 80.6) | (100 ± 89.4) | (107 ± 101) | (114 ± 79.6) |
| % subjects <20 pg/mL | 5.6 | 4.8 | 4.1 | 3.7 | 6.1 | 3.5 | 4.7 |
| % subjects 20-50 pg/mL | 37.4 | 29.2 | 25.6 | 26.8 | 24.9 | 26.6 | 19.0 |
| % subjects >50 pg/mL | 57.1 | 66.0 | 70.3 | 69.5 | 69.0 | 69.9 | 76.3 |
| 150 mg QD | | | | | | | |
| N | 205 | 201 | 185 | 190 | 167 | 175 | 158 |
| Median | 67.0 | 43.6 | 37.2 | 41.7 | 47.5 | 46.9 | 55.8 |
| (Mean ± SD) | (87.1 ± 69.6) | (74.6 ± 96.5) | (56.6 ± 53.1) | (64.9 ± 63.4) | (69.5 ± 82.6) | (61.1 ± 52.0) | (76.8 ± 64.9) |
| % subjects <20 pg/mL | 5.9 | 18.4 | 22.2 | 20.5 | 19.2 | 18.3 | 13.9 |
| % subjects 20-50 pg/mL | 28.3 | 38.8 | 41.6 | 35.3 | 32.9 | 36.0 | 32.9 |
| % subjects >50 pg/mL | 65.9 | 42.8 | 36.2 | 44.2 | 47.9 | 45.7 | 53.2 |
| 200 mg BID | | | | | | | |
| N | 211 | 192 | 185 | 184 | 180 | 177 | 153 |
| Median | 63.2 | 8.43 | 8.95 | 10.9 | 10.6 | 13.0 | 13.1 |
| (Mean ± SD) | (83.9 ± 74.5) | (22.4 ± 52.2) | (21.2 ± 32.0) | (28.6 ± 45.6) | (24.3 ± 34.9) | (35.0 ± 62.9) | (31.8 ± 46.6) |
| % subjects <20 pg/mL | 5.7 | 77.1 | 70.8 | 67.4 | 70.0 | 63.8 | 62.1 |
| % subjects 20-50 pg/mL | 35.1 | 13.5 | 17.8 | 16.3 | 15.0 | 17.0 | 18.3 |
| % subjects >50 pg/mL | 59.2 | 9.4 | 11.4 | 16.3 | 15.0 | 19.2 | 19.6 |

Example 6: Impact of Water-Insoluble Filler & Surfactant

An immediate release formulation containing sodium carbonate was prepared. All components, except magnesium stearate, were blended in a high-shear granulator and granulated with neat, de-ionized water. The granules were tray-dried at 40° C. and passed through a #20 US Standard sieve and lubed with magnesium stearate. Compound A referenced in Table 14 below is the Compound A sodium salt.

TABLE 15

Percent Compound A released in pH 6.8 buffer

| | Mean % | |
|---|---|---|
| Minutes | F12 | F12A |
| 15 | 14.3 | 27.4 |
| 30 | 39.2 | 62.1 |
| 45 | 59.6 | 86.4 |

Example 7: Impact of Sodium Carbonate on Dissolution

Figure 7:
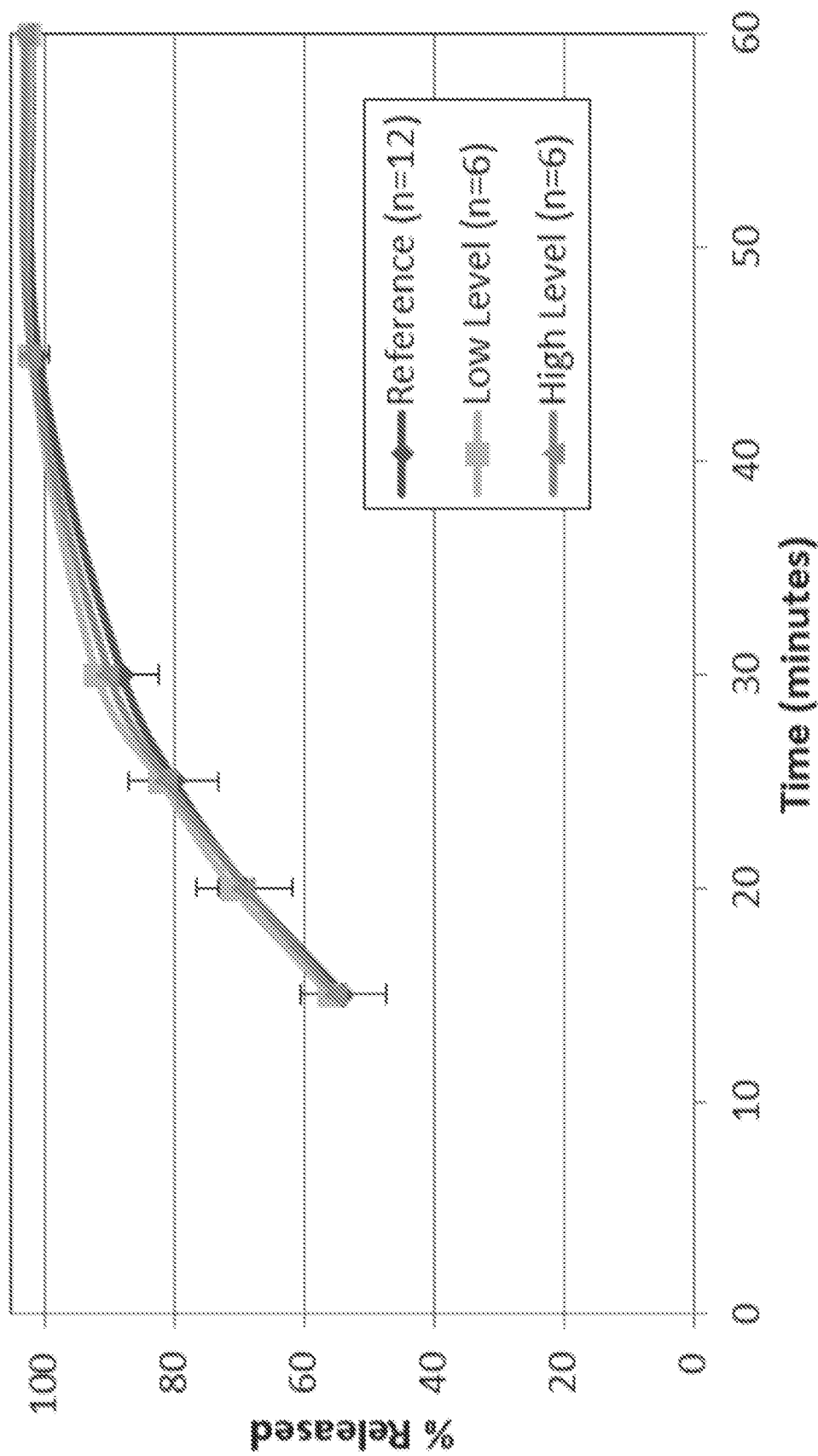
FIG. 7 is a graph showing an in vitro dissolution profile for compositions containing varying amounts of sodium carbonate monohydrate.

The impact of sodium carbonate monohydrate level on dissolution was examined. The amount of sodium carbonate monohydrate was varied by +20% of the nominal level to study the impact on dissolution. Mannitol level was adjusted in the formulation to maintain the overall tablet weight. A slugging process was used to manufacture tablets to a target solid fraction of 0.88 hardness of 125 N. Dissolution profiles for tablets from the batches are presented in FIG. 7. All results passed the proposed dissolution specification at t=30 minutes. The results indicate the +20% change in the level of sodium carbonate monohydrate does not impact dissolution.

Example 8: Impact of Sodium Carbonate on Degradation Products, Including Compound B One degradation product of Compound A is Compound B, which has a lactam moiety. The lactam moiety may be determined using numerous techniques. In one embodiment, the lactam moiety is determined using reversed phase high performance liquid chromatography (HPLC) with ultraviolet (UV) detection at 275 nm. The HPLC system consists of a C8 column with a flow rate at 1.1 mL/min. The column temperature is kept at 50° C. throughout the analysis. Both mobile phase A and B are applied, where mobile phase A is triethylamine/acetic acid buffer solution with an ratio of water:triethylamines:acetic acid in 100:0.1:0.06 (v/v) at pH 5.3 and mobile phase B is Acetonitrile. The diluent is triethylamine/acetic acid buffer solution and acetonitrile in a 50:50 (v/v) ratio. The detection limit standard is prepared in diluent with an accurately known concentration of about 0.06 pg elagolix free form/mL. The typical relative retention times (RRT) for the lactam moiety is approximately at 1.48 and the normalization factor is (NF) is 1.08.

Figure 8:
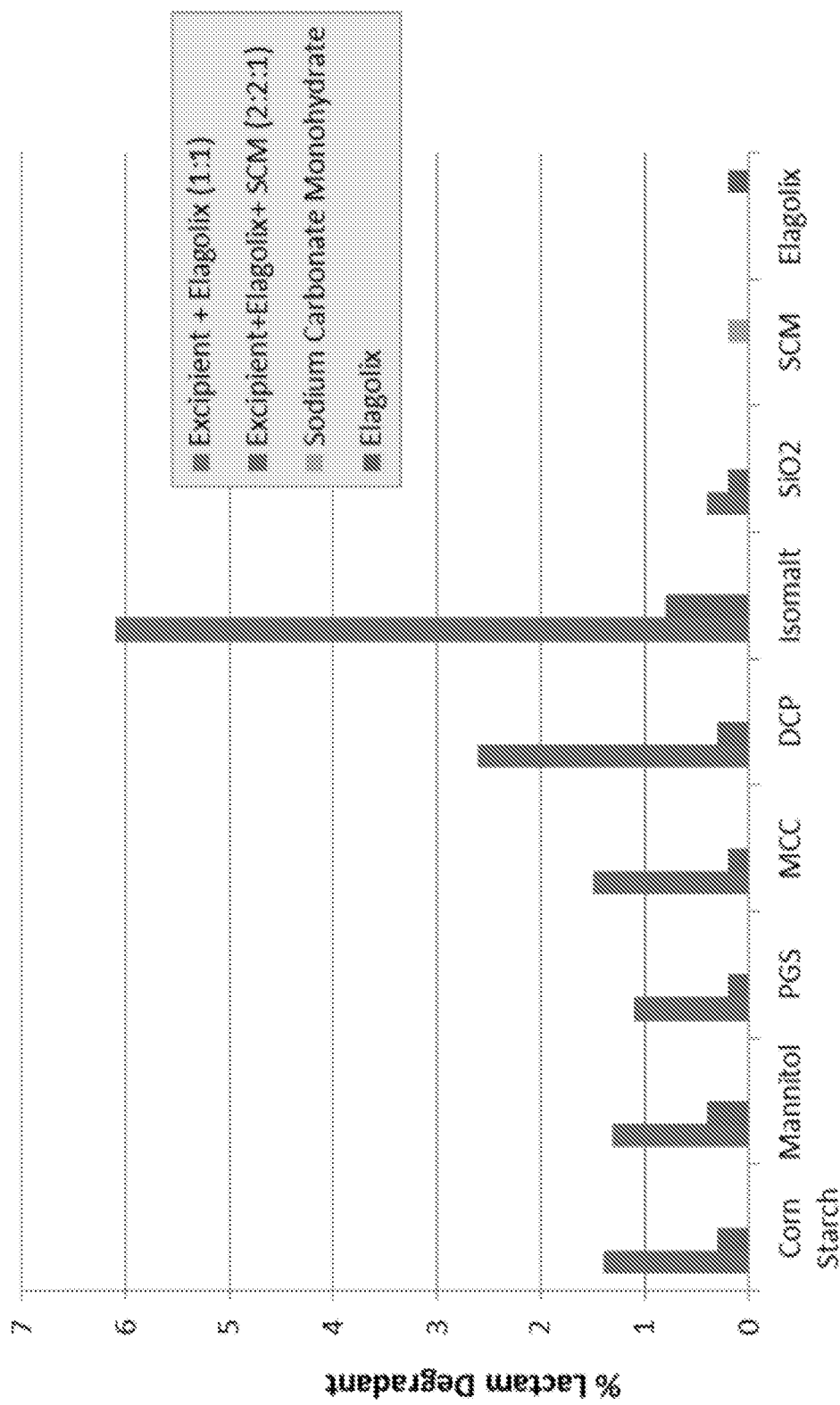
FIG. 8 is a bar graph showing percentage of a degradation product (Compound B) after storage for one week.

Excipient compatibility studies were conducted using mixtures of excipients and Compound A with and without sodium carbonate. The results are shown in FIG. 8. All excipients showed much higher formation of lactam in absence of sodium carbonate. In the presence of sodium carbonate, the excipients showed much lower content of lactam, very close to the detectable limit of about 0.03%.

Figure 9:
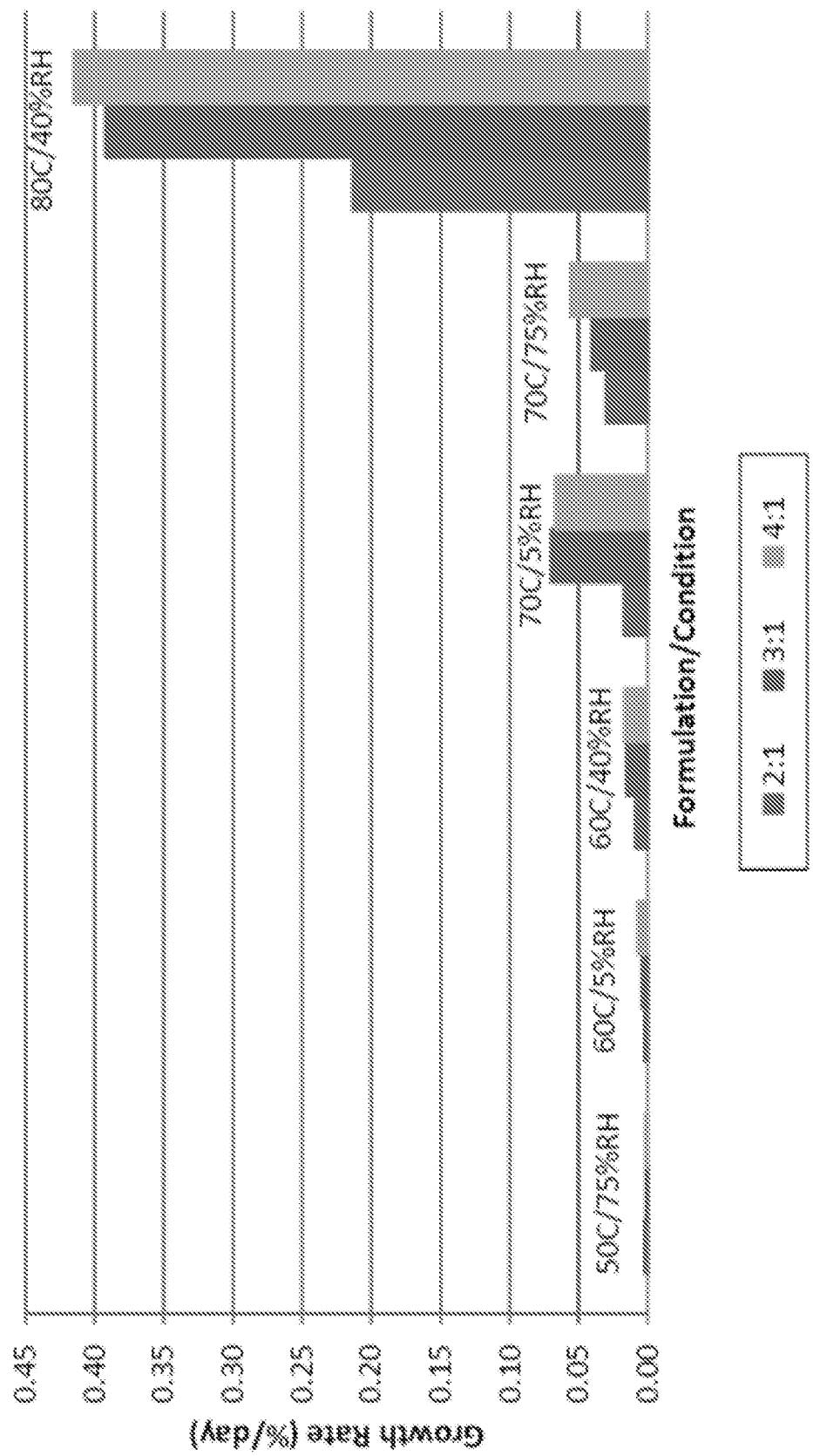
FIG. 9 is a bar graph showing formation rate of a degradation product (Compound B) under various storage conditions.

Formulations using 2:1, 3:1, and 4:1 w/w ratio of Compound A to sodium carbonate monohydrate were prepared. These formulations contained ~35% Compound A, sodium carbonate monohydrate, mannitol, pregelatinized starch, povidone, and magnesium stearate. The tablets were film coated and tested under accelerated stability protocol conditions of 50° C./75% RH, 60° C./5% RH, 60° C./40% RH, 70° C./5% RH, 70° C./75% RH, 80° C./40% RH over a period ranging from 2 to 25 days. The results are shown in FIG. 9. Formulations prepared with 3:1 and 4:1 w/w ratio of Compound A to sodium carbonate showed higher presence of the lactam degradant, whereas formulations with 2:1 w/w ratio showed relatively less formation of the lactam degradant.

Additional stability testing was performed on Formulations F5 and F7. The tablets were prepared, placed in clear blister pack with aluminum foil, and stored under the following conditions: 25° C./60% RH or 40° C./75% RH. Tablets were assessed for the presence of degradation products, including Compound B, at 0 (initial), 1, 3, 6, 9, 12, 18, and 24 months for the 25° C./60% RH condition and at 0 (initial), 1, 3, and 6 months for the 40° C./75% RH condition. The results are presented in Table 16.

TABLE 16

| Stability of F5 and F7 up to 24 months | | | | | | | | | | |
|---|---|---|---|---|---|---|---|---|---|---|
| Storage | | Degradation | Months | | | | | | | |
| Condition | Formulation | Product [%] | 0 | 1 | 3 | 6 | 9 | 12 | 18 | 24 |
| 25° C. 60% RH | F5 | Compound B | ND | ND | ND | ND | ND | ND | ND | ND |
|  |  | Total | 0 | 0 | 0.10 | 0.10 | 0 | 0.11 | 0.10 | 0.11 |
|  | F7 | Compound B | ND | ND | ND | ND | ND | ND | ND | ND |
|  |  | Total | 0 | 0 | 0 | 0 | 0 | 0 | 0.11 | 0.22 |
| 40° C. 75% RH | F5 | Compound B | ND | ND | <0.10 | <0.10 | NT | NT | NT | NT |
|  |  | Total | 0 | 0 | 0.23 | 0.35 | NT | NT | NT | NT |
|  | F7 | Compound B | ND | ND | <0.10 | <0.10 | NT | NT | NT | NT |
|  |  | Total | 0 | 0 | 0.10 | 0.33 | NT | NT | NT | NT |

ND = not detected;
NT = not tested

Example-9: Preparation of Elagolix Sodium 200 mg Tablets Containing Different pH Modifying Agent for Stability and Dissolution Testing Formulation Elagolix sodium 200 mg tablet formulation containing different types and amounts of pH modifying agent, such as a buffer agent were prepared. The pH modifying agent used in the study are presented in Table C1. The formulation compositions are presented in Table C2.

TABLE C1

| List of pH Modifying Agent | |
|---|---|
| pH Modifying Agent | Vendor |
| Sodium Carbonate | Jost Chemical |
| N-Methyl-D-glucamine | Sigma |
| Calcium hydroxide | Sigma-Aldrich |
| Trisodium phosphate anhydrous | Combi-Blocks |
| L-Arginine | Sigma-Aldrich |
| Eudragit EPO | EVONIK |
| Piperazine | Combi-Block |

TABLE C2

Formulation Compositions

| | Formulation ID | | | | |
|---|---|---|---|---|---|
| | 1 | 2 | 3 | 4 | 5 |
| Weight by Weight Ratio of pH Modifying Agent to Elagolix Sodium (pH modifying Agent:Elagolix Sodium) | 0:1 | 1:4 | 1:6 | 1:10 | 1:20 |
| Elagolix Sodium (% w/w) | 41.67 | 37.74 | 38.96 | 40.00 | 40.82 |
| Mannitol (% w/w) | 40.34 | 36.53 | 37.72 | 38.72 | 39.51 |
| Starch 1500 (% w/w) | 11.96 | 10.83 | 11.18 | 11.48 | 11.71 |
| Povidone K28/30 (% w/w) | 3.74 | 3.39 | 3.50 | 3.59 | 3.67 |
| Magnesium Stearate (% w/w) | 2.29 | 2.08 | 2.15 | 2.20 | 2.25 |
| pH Modifying Agent | 0.00 | 9.43 | 6.49 | 4.00 | 2.04 |
| Total (% w/w) | 100.0 | 100.0 | 100.0 | 100.00 | 100.0 |
| pH Modifying Agent Name | None | Sodium Carbonate | Sodium Carbonate | Sodium Carbonate | Sodium Carbonate |

| | Formulation ID | | | | | |
|---|---|---|---|---|---|---|
| | 6 | 7 | 8 | 9 | 10 | 11 |
| Weight by Weight Ratio of pH Modifying Agent to Elagolix Sodium (pH modifying Agent:Elagolix Sodium) | 1:2 | 1:2 | 1:2 | 1:2 | 1:2 | 1:2 |
| Elagolix Sodium (% w/w) | 34.50 | 34.50 | 34.50 | 34.50 | 34.50 | 34.50 |
| Mannitol (% w/w) | 33.38 | 33.38 | 33.38 | 33.38 | 33.38 | 33.38 |
| Starch 1500 (% w/w) | 9.85 | 9.85 | 9.85 | 9.85 | 9.85 | 9.85 |
| Povidone K28/30 (% w/w) | 3.07 | 3.07 | 3.07 | 3.07 | 3.07 | 3.07 |
| Magnesium Stearate (% w/w) | 1.87 | 1.87 | 1.87 | 1.87 | 1.87 | 1.87 |
| pH Modifying Agent | 17.33 | 17.33 | 17.33 | 17.33 | 17.33 | 17.33 |
| Total (% w/w) | 100.0 | 100.0 | 100.0 | 100.0 | 100.0 | 100.0 |
| pH Modifying Agent Name | N-Methyl-D-glucamine | Calcium hydroxide | L-Argnine | Trisodium phosphate anhydrous | Eudragit EPO | Piperazine |

Preparation of Stability Tablets

The 200 mg round tablets for stability study were prepared using direct blending and compression process with target tablet weight shown in Tablet C3. The target tablet solid fraction is consistent for all the formulations.

Preparation of Dissolution Tablets

The 200 mg oval tablets for dissolution study were prepared using blending→slugging→milling→compression process. The formulation blends were slugged and then milled through 1.0 mm screen. The target tablet solid fraction is consistent for all the formulations.

TABLE C3

Target Tablet Weight

| Formulation ID | Target Tablet Weight (mg) |
|---|---|
| 1 | 496.8 |
| 2 | 548.6 |
| 3 | 531.3 |
| 4 | 517.5 |
| 5 | 507.2 |
| 6 | 600.0 |
| 7 | 600.0 |
| 8 | 600.0 |
| 9 | 600.0 |
| 10 | 600.0 |
| 11 | 600.0 |

TABLE C4

Lactam Moiety (Compound B) in the Accelerated Stability Study

| Formulation no. | Lactam Moiety % (w/w) at 60° C./40% RH for 13 days |
|---|---|
| 1 | 0.77 |
| 2 | 0.23 |
| 3 | 0.32 |
| 4 | 0.32 |
| 5 | 0.35 |
| 6 | 0.10 |
| 7 | 0.10 |
| 8 | 0.09 |
| 9 | 0.09 |
| 10 | 0.27 |
| 11 | 0.16 |

TABLE C5

Elagolix Sodium % Release on Selected Formulations at pH 1.2

| | Mean of % Release (STDEV) (N = 6) | |
|---|---|---|
| Formulation No. | 30 min | 45 min |
| 1 | 43 (1.7) | 61 (2.1) |
| 2 | 65 (1.7) | 91 (1.3) |
| 8 | 67 (5.1) | 86 (3.2) |
| 10 | 46 (0.8) | 65 (0.4) |
| 11 | 77 (6.7) | 95 (5.4) |

Figure 10:
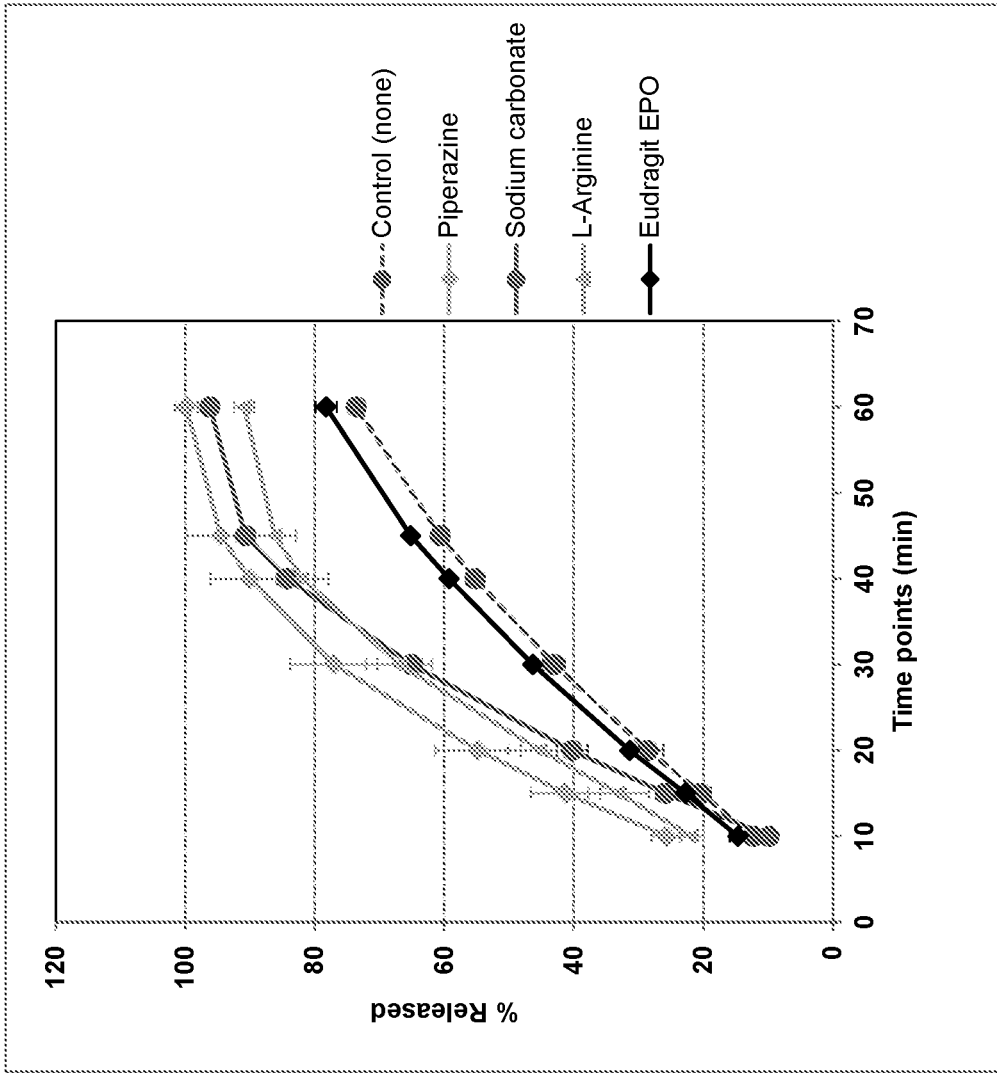
FIG. 10: Depicts dissolution profiles of elagolix sodium formulations 1, 2, 8, 10, 11 at pH 1.2 (USP apparatus I at 100 RPM and 37° C.).

FIG. 10 provides the dissolution profiles of elagolix sodium formulations 1, 2, 8, 10, 11 at pH 1.2 (USP apparatus I at 100 RPM and 37° C.).

Example A-1: Efficacy and Safety of Elagolix in a Subgroup of Women with Uterine Fibroids and Non-Dominant Adenomyosis Adenomyosis is an estrogen-dependent disease of benign endometrial tissue growth within the uterine muscular tissue, and is associated with heavy menstrual bleeding (HMB) and dysmenorrhea. Adenomyosis occurs when endometrial tissue, which normally lines the uterus, exists within and grows into the muscular wall of the uterus. The displaced endometrial tissue continues to act as it normally would— thickening, breaking down and bleeding—during each menstrual cycle. An enlarged uterus and painful, heavy periods can result. Symptoms most often start late in the childbearing years after having children. The cause of adenomyosis remains unknown, but the disease typically disappears after menopause. For women who experience severe discomfort from adenomyosis, certain treatments can help, but hysterectomy is the only cure. Sometimes, adenomyosis is silent— causing no signs or symptoms—or only mildly uncomfortable. In other cases, adenomyosis may cause: Heavy or prolonged menstrual bleeding, severe cramping or sharp, knifelike pelvic pain during menstruation (dysmenorrhea), menstrual cramps that last throughout your period and worsen as you get older, pain during intercourse and blood clots that pass during your period.

An analysis of the efficacy and safety of elagolix in a subgroup of women with UF and adenomyosis was conducted.

Patients and Methods: A 6-month, randomized, double-blind, placebo-controlled, 2-cohort, phase 2b clinical trial evaluating the safety and efficacy of elagolix (Cohort 1, 300 mg twice daily [BID] and Cohort 2, 600 mg once daily [QD]), elagolix with 0.5 mg estradiol (E2)/0.1 mg norethindrone acetate (NETA), and elagolix with 1.0 mg E2/0.5 mg NETA in premenopausal women with HMB (≥80 mL/month) and UF was conducted. Elagolix studied in this clinical trial comprised the sodium salt of Compound A.

All subjects were evaluated with ultrasound and a subset volunteered to also be evaluated by MRI. Women were excluded from the study if they had evidence of diffuse or segmental adenomyosis as a dominant condition (>50% of the myometrium via ultrasound/MRI). Efficacy and safety were evaluated post hoc in a subgroup of women who had confirmed non-dominant adenomyosis (ultrasound/MRI) at baseline. Menstrual blood loss (MBL) was quantified from sanitary products (alkaline hematin). The composite primary endpoint was the proportion of women who had a ≥50% reduction from baseline in HIB and <80 mL MBL in the last 28 days of treatment. Adverse events (AEs) were recorded.

Results: Of the 567 women treated in the study, 86 women (15%; Cohort 1, n=32; Cohort 2, n=54) had confirmed adenomyosis (ultrasound and/or MRI). The majority (72%) of women with confirmed adenomyosis were Black and 87% had a ≥25 BMI at baseline. The proportion of women in Cohort 1 who had a ≥50% reduction from baseline in HMB and <80 mL menstrual blood loss (MBL) in the last 28 days of treatment were 40% for placebo (n=10), 80% for elagolix 300 mg BID (n=5), 83% for elagolix 300 mg BID with 0.5 mg E2/0.1 mg NETA (n=12), and 100% for elagolix 300 mg BID with 1.0 mg E2/0.5 mg NETA (n=5); and in Cohort 2, 13% for placebo (n=16), 92% for elagolix 600 mg QD (n=13), 93% for elagolix 600 mg QD with 0.5 mg E2/0.1 mg NETA (n=14), and 89% for elagolix 600 mg QD with 1.0 mg E2/0.5 mg NETA (n=9). At least 1 AE, related or unrelated to study drug, was reporting in 90% of the placebo group (n=10) and 77% of elagolix-treated groups (n=22) in Cohort 1 and 88% of the placebo group (n=16) and 67% of the elagolix-treated groups (n=38) in Cohort 2.

Example A-2: Safety and Efficacy of Elagolix in Women with Symptomatic Adenomyosis The safety, efficacy, and tolerability of elagolix 300 mg BID in combination with E2/NETA (estradiol 1 mg/norethindrone acetate 0.5 mg QD), versus Placebo in premenopausal women 18-51 years of age with symptomatic adenomyosis will be assessed in a clinical trial.

Elagolix 300 mg BID equivalent with add-back treatment is expected to reduce heavy menstrual bleeding (HMB) and pelvic pain in women with symptomatic adenomyosis. Other doses of add back and elagolix as previously described may also be used for the treatment of symptomatic adenomyosis.

Various aspects of the evaluation where elagolix may be found to be efficacious and safe may include the following:
(a) Reduction in heavy menstrual bleeding to <80 ml/mo with a >50% reduction from baseline in menstrual blood loss (MBL) at Month 6;
(b) A clinically meaningful decrease (defined as >30% reduction from baseline) in pelvic pain at Month 3. This assessment will take other co-medications, such as analgesic into consideration as well;
(c) Reduction in heavy menstrual bleeding to <80 ml/mo with a >50% reduction from baseline in MBL at Month 3;
(d) Reduction in heavy menstrual bleeding to <80 ml/mo with a >50% reduction from baseline in MBL at Month 12;
(e) A clinically meaningful decrease (defined as >30% reduction) from baseline in pelvic pain at Month 6. This assessment will take other co-medications, such as analgesic into consideration as well;
(f) MBL volume mean change from baseline vs placebo;
(g) Suppression of bleeding as defined by amenorrhea+/− spotting;
(h) Suppression of menstrual cramps that last throughout the menstrual period;
(i) Reduction of pain during intercourse; or
(j) Reduction of blood clots that pass during menstrual period.

Safety evaluations may include physical examination, vital signs, endometrial assessments (endometrial thickness and biopsy), pelvic ultrasound [TAU (Transabdominal Ultrasound)/TVU (Transvaginal Ultrasound)], clinical laboratory tests and adverse events monitoring.

Example A-3: Safety and Efficacy of Elagolix in Endometriosis Related Conditions (I) Elagolix is an orally administered, short-acting, selective, non-peptide small molecule GnRH receptor antagonist that blocks endogenous GnRH signaling by binding competitively to GnRH receptors in the pituitary gland. Administration of elagolix results in dose-dependent suppression of luteinizing hormone (LH) and follicle-stimulating hormone (FSH) levels, leading to decreased blood levels of the ovarian sex hormones, estradiol and progesterone. LH and FSH suppression begins within hours of administration and is readily reversible upon discontinuation of elagolix.

(a) Pharmacodynamics: Effect on Ovulation and Estradiol

During the course of a 3-menstrual cycle study in healthy women, elagolix 150 mg QD and 200 mg BID resulted in an ovulation rate of approximately 50 and 32%, respectively. In the Phase 3 studies in women with endometriosis, partial suppression of estradiol to approximately 50 pg/mL was observed for ELAGOLIX 150 mg QD, whereas nearly full suppression of estradiol to approximately 12 pg/mL was observed following treatment with elagolix 200 mg BID.

(b) Effect of Elagolix on QT Interval

Elagolix does not prolong the QTc interval. The effect of elagolix (up to 1200 mg) on QTc interval was evaluated in an active-controlled (moxifloxacin 400 mg) thorough QT study. At 17- to 23-fold (relative to 200 mg BTD and 150 mg QD regimens, respectively) of elagolix therapeutic concentrations elagolix did not prolong the QTc interval.

(II) The pharmacokinetic properties of elagolix in healthy subjects are provided in Table A-1. The steady state pharmacokinetic parameters are presented in Table A-2.

TABLE A-1

Pharmacokinetic Properties of Elagolix in Healthy Subjects

| Absorption | |
|---|---|
| $T_{max}$ (h) | 1.0 |
| Effect of high-fat meal (relative to fasting) | ↓24% |
| Distribution | |
| % Bound to human plasma proteins | 80 |
| Blood-to-plasma ratio | 0.6 |
| Metabolism | |
| Metabolism | CYP3A (major) Minor pathways include: CYP2D6, CYP2C8, and uridine glucuronosyltransferases (UGTs) |
| Elimination | |
| Major route of elimination | Hepatic metabolism |
| Terminal phase elimination half-life ($t_{1/2}$) (h) | 4-6 |
| % of dose excreted in urine | <3 |
| % of dose excreted in feces | 90 |

TABLE A-2

Mean (% CV) Steady State Pharmacokinetic Parameters of Elagolix

| Pharmacokinetic Parameter (Units) | 150 mg QD | 200 mg BID |
|---|---|---|
| $C_{max}$ (ng/mL) | 574 (29) | 774 (68) |
| $AUC_\tau$ (ng · hr/mL) | 1292 (31) | 1725 (57) |

CV: Coefficient of variation
$C_{max}$: peak concentration
$AUC_\tau$: area under the plasma concentration-time curve during the dosing interval (τ) i.e., 12 hours for BID, 24 hours for QD.

(III) Pharmacokinetics in Specific Populations (a) Renal Impairment

Elagolix exposures (Cmax and AUC) are not altered by renal impairment. The mean exposures are similar for women with moderate to severe or end stage renal disease (including women on dialysis) compared to women with normal renal function.

(b) Hepatic Impairment

Elagolix exposures (Cmax and AUC) are similar between women with normal hepatic function and women with mild hepatic impairment. Elagolix exposures in women with moderate and severe hepatic impairment are approximately 3-fold and 7-fold, respectively, of exposures from women with normal hepatic function.

(IV) Drug Interaction Studies

Drug interaction studies were performed with elagolix and other drugs that are likely to be co-administered and with drugs commonly used as probes for pharmacokinetic interactions. Tables A-3 and A-4 summarize the pharmacokinetic effects when elagolix was co-administered with other drugs which showed potentially clinically relevant changes.

TABLE A-3

Drug Interactions: Change in Pharmacokinetic Parameters of Elagolix in the Presence of Co-administered Drug

| Co-administered Drug | Regimen of Co-administered Drug | Regimen of Flagolix | N | Ratio (90% CI)* $C_{max}$ | AUC |
|---|---|---|---|---|---|
| Ketoconazole | 400 mg once daily | 150 mg single dose | 11 | 1.77 (1.48-2.12) | 2.20 (1.48-2.44) |
| Rifampin | 600 mg single dose | 150 mg single dose | 12 | 4.37 (3.62-5.28) | 5.58 (4.88-6.37) |
|  | 600 mg once daily |  |  | 2.00 (1.66-2.41) | 1.65 (1.45-1.89) |

CI: Confidence interval
*ratios for $C_{max}$ and AUC compare co-administration of the medication with elagolix vs. administration of elagolix alone.

TABLE A-4

Drug Interactions: Change in Pharmacokinetic Parameters of Co-administered Drug in the Presence of Elagolix

| Co-administered Drug | Regimen of Co-administered Drug | Regimen of Elagolix | N | Ratio (90% CI)* $C_{max}$ | AUC |
|---|---|---|---|---|---|
| Digoxin | 0.5 mg single dose | 200 mg twice daily × 10 days | 11 | 1.71 (1.53-1.91) | 1.26 (1.17-1.35) |
| Rosuvastatin | 20 mg once daily | 300 mg twice daily × 7 days | 10 | 0.99 (0.73-1.35) | 0.60 (0.50-0.71) |
| Midazolam | 2 mg single dose | 300 mg twice daily × 11 days | 20 | 0.56 (0.51-0.62) | 0.46 (0.41-0.50) |
|  |  | 150 mg once daily × 13 days | 11 | 0.81 (0.74-0.89) | 0.65 (0.58-0.72) |
| Norethindrone | 0.35 mg once daily × 112 days | 150 mg once daily × 56 days | 32 | 0.95 (0.86-1.05) | 0.88 (0.79-0.99) |
| Ethinyl Estradiol | Ethinyl estradiol 35 mcg and triphasic norgestimate 0.18/0.215/0.25 mg once daily | 150 mg once daily | 21 | 1.15 (1.07-1.25) | 1.30 (1.19-1.42) |
| Norelgestromin[a] |  |  |  | 0.87 (0.78-0.97) | 0.85 (0.78-0.92) |
| Norgestrel[a] |  |  |  | 0.89 (0.78-1.00) | 0.92 (0.84-1.01) |

CI: Confidence interval
*ratios for $C_{max}$ and AUC compare co-administration of the medication with elagolix vs. administration of the medication alone.
[a]metabolite of norgestimate (V) Drug Interactions
  (a) Potential for Elagolix to Affect Other Drugs
  Elagolix is a weak to moderate inducer of cytochrome P450 (CYP) 3A enzyme. Co-administration with elagolix may decrease plasma concentration of drugs that are substrates of CYP3A.
  Elagolix is an inhibitor of efflux transporter P-glycoprotein (P-gp) at 200 mg BID or higher, such as 300 mg BID or 400 mg QD or 600 mg QD. Co-administration with ELAGOLIX 200 mg BID may increase plasma concentration of drugs that are substrates of P-gp.
  (b) Potential for Other Drugs to Affect Elagolix
  Elagolix is a substrate of CYP3A, P-gp, and organic anion transporting polypeptide (OATP)1B1. Clinically meaningful interactions are not expected when elagolix is co-administered with drugs that inhibit CYP3A or P-gp.
  Co-administration of elagolix with drugs that induce CYP3A may decrease elagolix plasma concentrations.
  Co-administration of elagolix with drugs that inhibit OATP1B1 may increase elagolix plasma concentrations. Use of potent OATP1B1 inhibitors are not recommended with elagolix 200 mg BID regimen.
  (c) Established and Other Potential Drug Interactions
  Table A-5 provides the effect of co-administration of elagolix on concentrations of concomitant drugs and the effect of concomitant drugs on elagolix.

TABLE A-5

Established Drug Interactions Based on Drug Interaction Trials

| | | |
|---|---|---|
| Antiarrhythmics digoxin | ↑ digoxin | Clinical monitoring is recommended for digoxin when co-administered with ORILISSA. |
| Antimycobacterial rifampin | ↑ elaolix | Concomitant use of ORILISSA 200 mg twice daily and rifampin is not recommended. Limit concomitant use of ORILISSA 150 mg once daily and rifampin to 6 months. |
| Benzodiazepines oral midazolam | ↓ midazolam | Consider increasing the dose of midazolam and individualize therapy based on the patient's response. |
| Statins rosuvastatin | ↓ rosuvastatin | Consider increasing the dose of rosuvastatin. |

See Clinical Pharmacology, Tables A-3 and A-4.
The direction of the arrow indicates the direction of the change in AUC (↑ = increase, ↓ = decrease).

(d) Drugs with No Observed Clinically Significant Interactions with Elagolix
  No dose adjustment is required when elagolix is co-administered with the following medications: ketoconazole, fluconazole, sertraline, and norethindrone or other progestin-only contraceptives.
(VI) Nonclinical Toxicology
  (a) Carcinogenesis
  The 2-year carcinogenicity studies (conducted in mice and rats) revealed no increase in tumors in mouse at any dose, but an increase in thyroid (male and female) and liver (males only) tumors occurred in rat at the high dose (13-fold margin of safety with respect to 200 mg BID in women). The rat tumors were identified as being species-specific and of negligible relevance to humans. This conclusion is based on a follow-on thyroid and hepatic effects-related investigative study performed to document the possibility that thyroid and liver tumors may be specific to rat and occurred via induction of hepatic drug metabolizing enzymes at the high dose.

(b) Mutagenesis
  Mutagenicity studies have been performed with elagolix using in vitro and in vivo test systems. These studies provided no evidence of a mutagenic or clastogenic potential.
  (c) Impairment of Fertility
  Effects on fertility and reproductive organs were evaluated in studies with rats and monkeys that achieved plasma concentrations less than the AUC at MRHD for rats and approximately 0.28-fold to 9.9-fold in monkeys, when adjusted for species difference in GnRH receptor binding affinity. In rats there was no effect in a fertility study (doses 50, 150, 300 mg/kg/day) but involution and a decrease in *corpora lutea* in ovaries were observed in a repeat-dose study (doses 600, 800 mg/kg/day). In a monkeys repeat-dose study (75, 150, 300 and 600 mg/kg/day), a reversible atrophy of reproductive organs (cervix, uterus and vagina) was observed at all doses. Based on pharmacologic actions of elagolix in humans a reversible effect on fertility may be expected in women.
(VII) Clinical Studies
  The efficacy of elagolix 150 mg QD and 200 mg BID in the management of endometriosis with associated pain was demonstrated in two international double-blind, placebo-controlled studies in 1686 premenopausal women (Study EM-I and EM-II), and two uncontrolled, blinded extension studies (Study EM-III and EM-IV). Each placebo-controlled study assessed the reduction in endometriosis-associated pain over 6 months of treatment. More than 75 percent of women who completed Study EM-I and EM-II enrolled in the extension studies for an additional 6 months treatment period. Subjects were followed for up to 12 months post-treatment. See FIGS. 11-14
  (a) Reduction in Pain
  The co-primary efficacy endpoints were the proportion of responders for dysmenorrhea and pelvic pain not related to menses (also known as non-menstrual pelvic pain [NMPP]) at Month 3 compared to placebo. The primary analysis independently evaluated these endpoints using a daily diary that asked patients to assess their pain and its impact on their daily activities, over the previous 24 hours. The Daily Endometriosis Pain Impact Scale, consisted of patient reported pain levels of None, Mild, Moderate or Severe (correlating with score of 0 to 3, respectively) and included a functional component for each score.
  Women were defined as responders if they experienced clinically meaningful reduction in dysmenorrhea and/or NMPP with no increased analgesic use for endometriosis associated pain.
  A higher proportion of women treated with elagolix 150 mg QD or 200 mg BID were responders for dysmenorrhea and NMPP versus placebo in a dose-dependent manner at Month 3. The persistence of efficacy was observed through Month 6 [see Table A-6].
  Dyspareunia was evaluated as a secondary endpoint using the Daily Endometriosis Pain Impact Scale.
  A higher proportion of women treated with elagolix 200 mg BID reported clinically meaningful reduction in dyspareunia versus placebo at Month 3 through Month 6.

TABLE A-6

Proportion and Number of Responders† for Dysmenorrhea, Non-Menstrual Pelvic Pain and Dyspareunia at Month 3 and Month 6 in Studies EM-I and EM-II, using the Daily Endometriosis Pain Impact Scale

| | Study EM-I | | | Study EM-II | | |
|---|---|---|---|---|---|---|
| | Elagolix | | | Elagolix | | |
| | 150 mg QD %/(n/N) | 200 mg BID %/(n/N) | Placebo %/(n/N) | 150 mg QD %/(n/N) | 200 mg BID % (n/N) | Placebo % (n/N) |
| Dysmenorrhea (Month 3) | 45.4*** (115/248) | 75.8*** (185/244) | 19.6 (73/373) | 43.4%*** (96/221) | 72.4*** (163/225) | 22.7 (80/353) |
| Dysmenorrhea (Month 6)α | 42.1*** (104/247) | 75.3*** (183/243) | 23.1 (86/372) | 46.2%*** (102/221) | 76.9*** (173/225) | 25.4 (90/355) |
| Non-Menstrual Pelvic Pain (Month 3) | 50.4*** (125/248) | 54.5*** (133/244) | 36.5 (136/373) | 49.8** (110/221) | 57.8*** (130/225) | 36.5 (129/353) |
| Non-Menstrual Pelvic Pain (Month 6)α | 45.7** (113/247) | 62.1*** (151/243) | 34.9 (130/372) | 51.6%** (114/221) | 62.2*** (140/225) | 40.6 (144/355) |
| Dyspareuniaα (Month 3) | 39.6 (74/187) | 47.1*** (81/172) | 31.9 (90/282) | 44.0 (70/159) | 53.7** (87/162) | 39.5 (101/256) |
| Dyspareuniaα (Month 6) | 39.6 (74/187) | 50.3*** (81/161) | 33.3 (90/270) | 39.9 (65/163) | 55.8*** (92/165) | 39.4 (100/254) |

†A responder had a reduction in pain from baseline to the analysis month greater than or equal to a calculated, clinically important threshold of improvement, and also had stable or decreased rescue analgesic use.
αA secondary endpoint
*, , *$P \leq 0.001, 0.01$, and $0.05$, respectively, for test of difference from placebo Both elagolix treatment groups showed mean decreases from Baseline in dysmenorrhea scores that were statistically significantly greater than placebo beginning at Month 1 and persisted through Month 6.

Women in these studies also provided a daily self-assessment of their endometriosis pain using the Numeric Rating Scale (NRS), on a scale ranging from 0 (no pain) to 10 (worst pain ever). Women taking elagolix 150 mg QD and 200 mg BID reported a highly statistically ($p<0.001$) significant reduction in NRS scores compared to placebo at Month 3 and Month 6.

Figure 11:
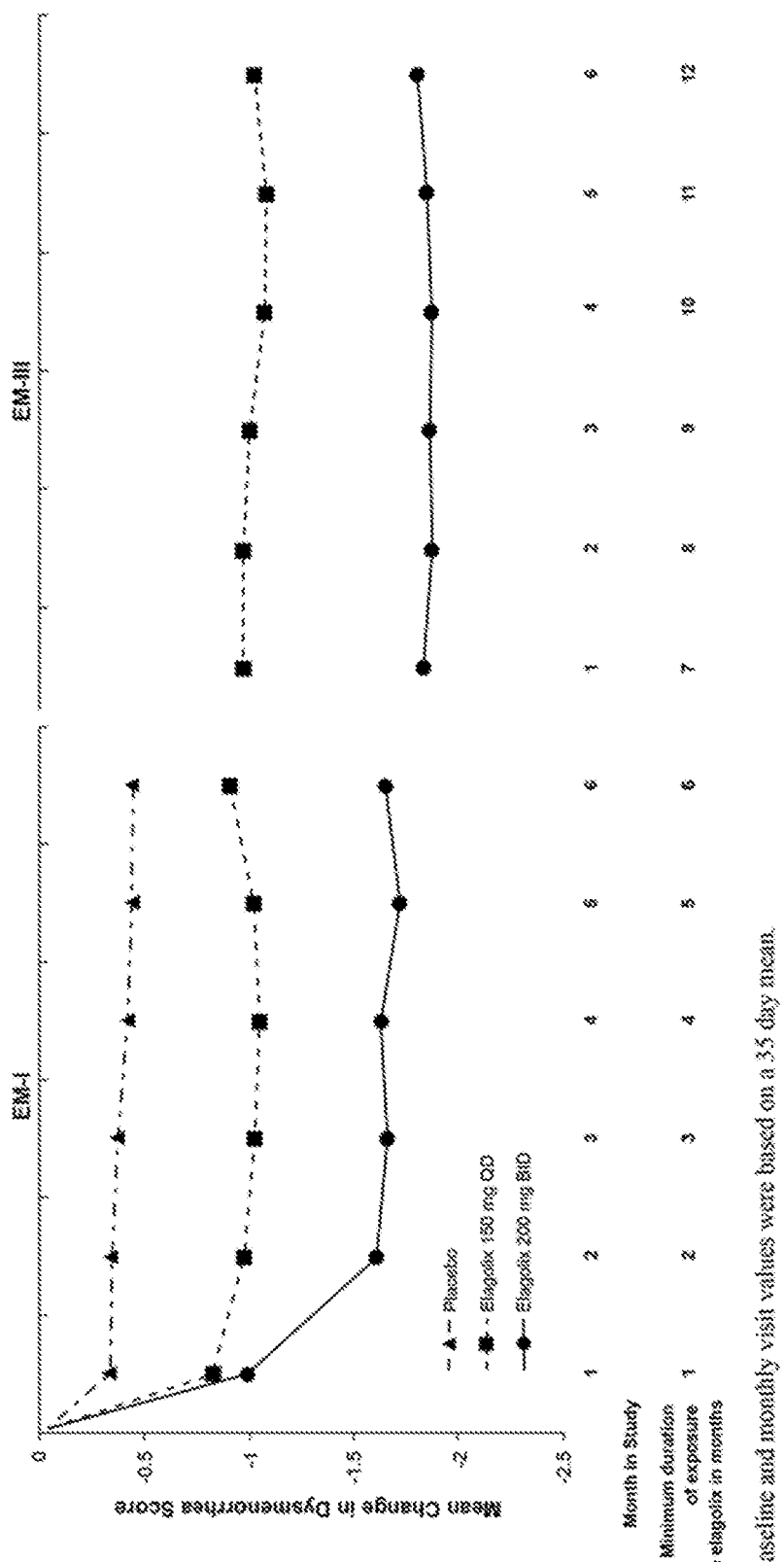
FIG. 11: Depicts mean change from baseline in mean dysmenorrhea pain scores in Study EM-I and maintenance of response in its extension study EM-III over 12 Months.
Figure 12:
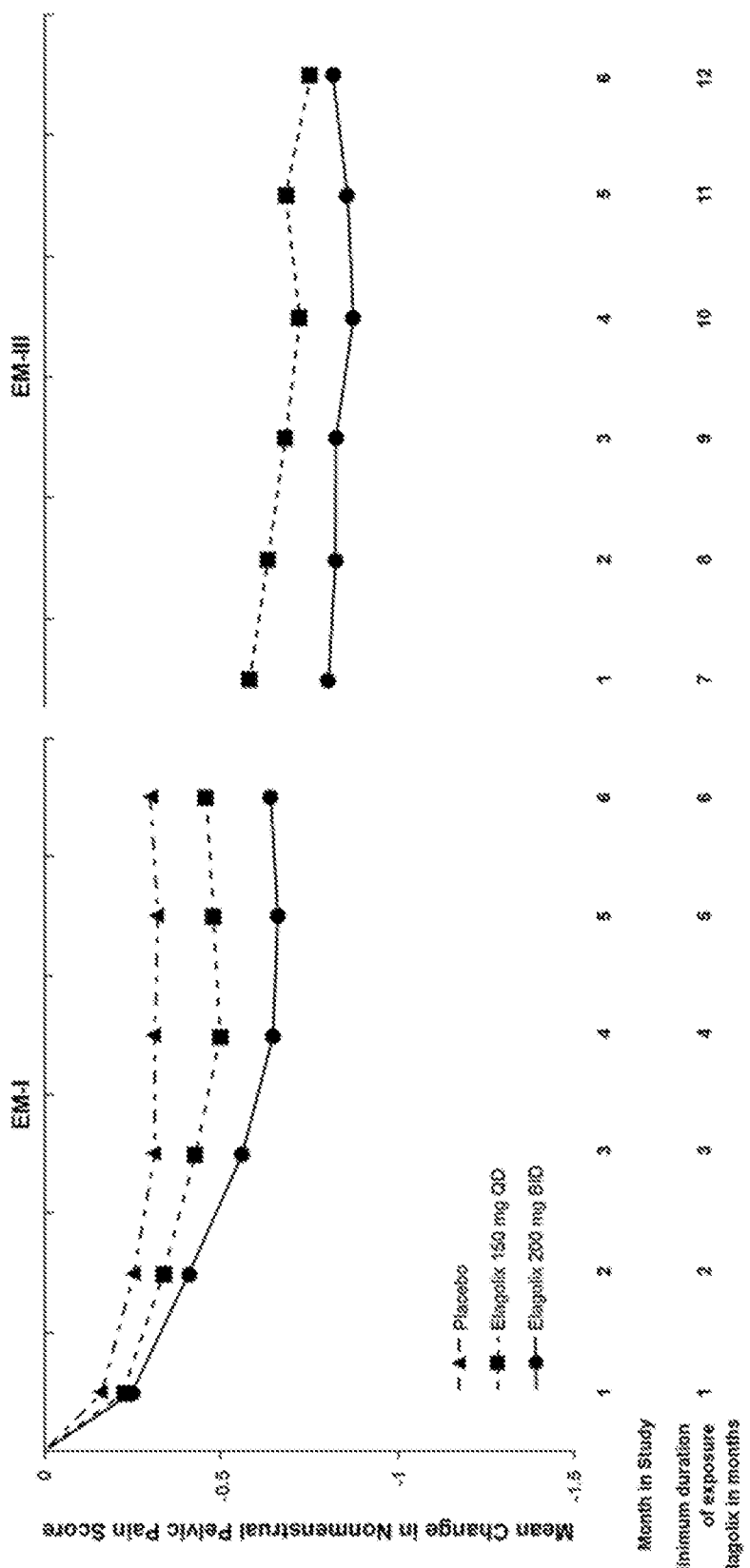
FIG. 12: Depicts mean change from baseline in mean NMPP Scores in study EM-I and maintenance of response in its extension Study EM-III over 12 months.
Figure 13:
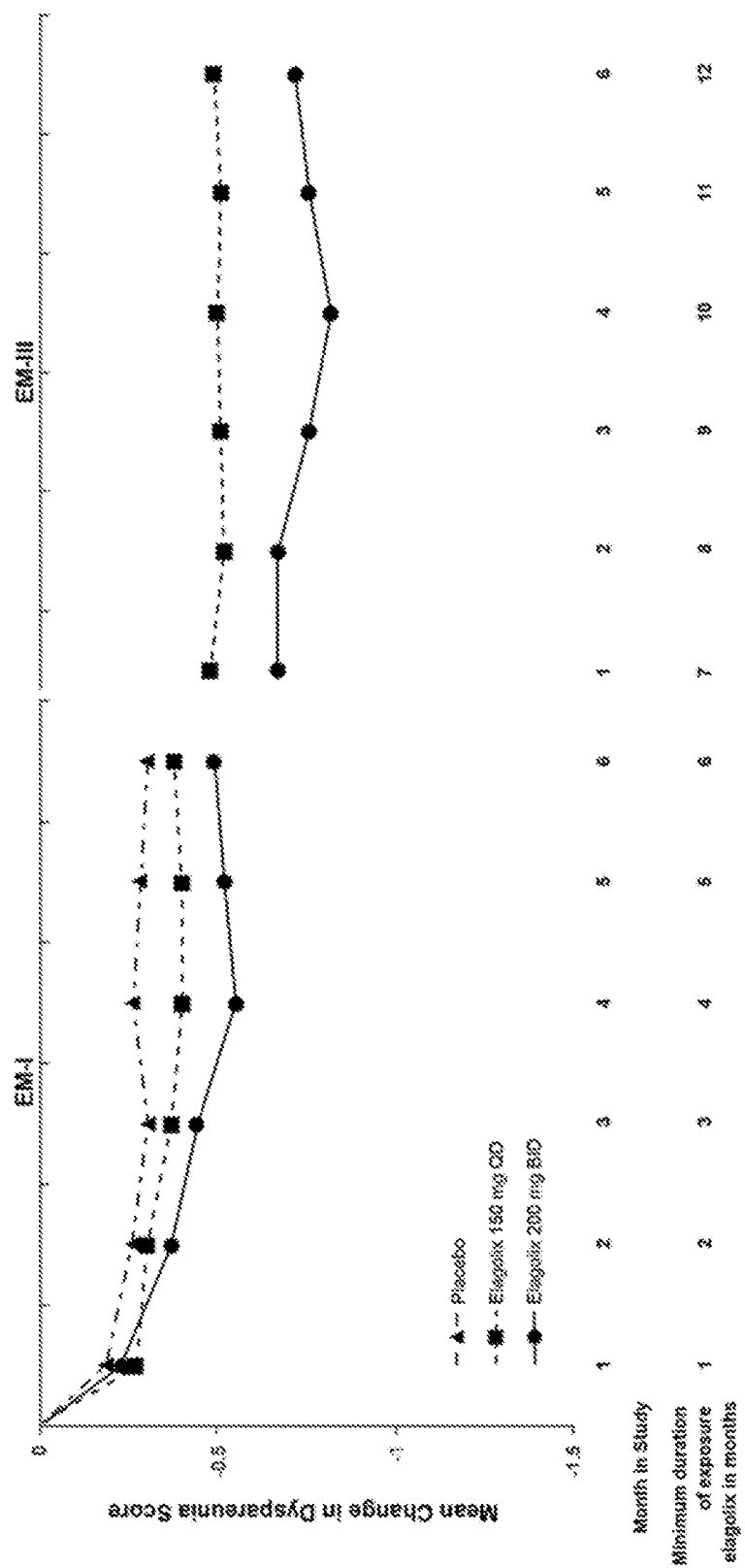
FIG. 13: Depicts mean change from baseline in mean dyspareunia pain scores in Study EM-I and maintenance of response in its extension Study EM-III over 12 Months
Figure 14:
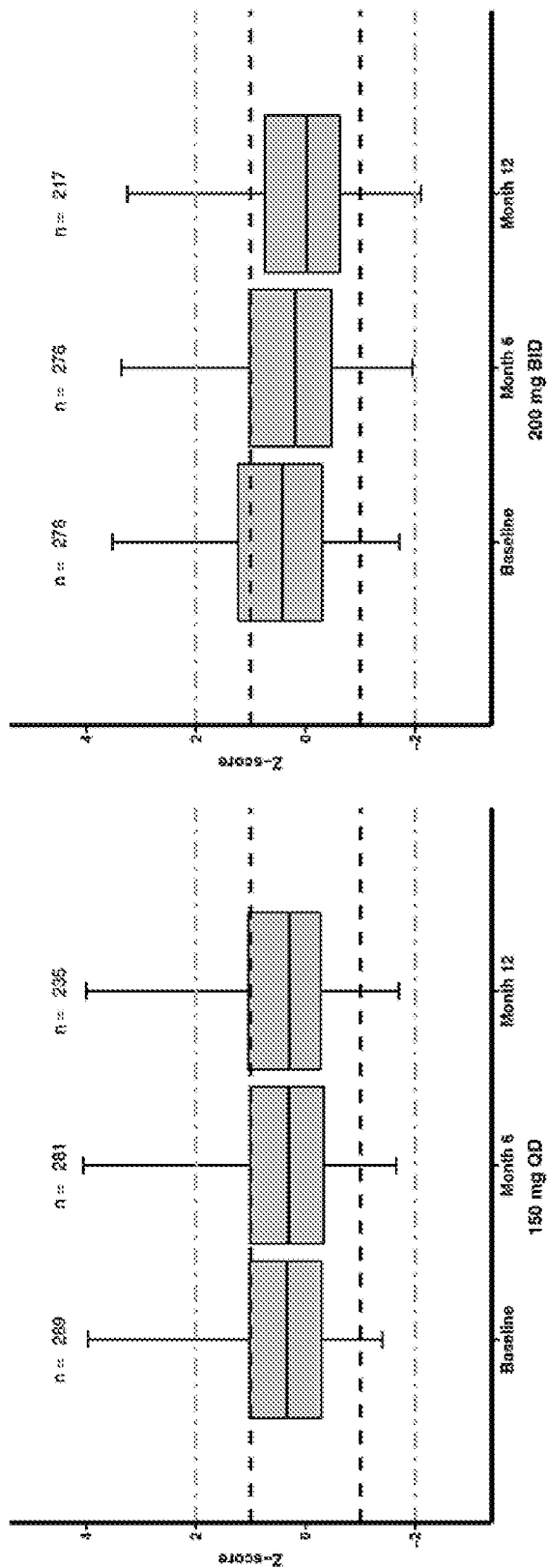
FIG. 14: Depicts lumbar spine BMD Z-score box plots at baseline, Month 6 and Month 12 for elagolix 150 mg QD and 200 mg BID.

In the two blinded extension studies EM-III and EM-IV, where the patients who were originally on elagolix in the controlled studies EM-I and EM-II were maintained on their dose, the durability of improvement in dysmenorrhea, NMPP and dyspareunia was demonstrated for a total of 12 months, see FIG. 11. In study EM-IV, efficacy was maintained when elagolix was taken with and without food.

Results on efficacy endpoints from Study EM-II were consistent with those observed in Study EM-I.

(b) Reduction in Pain Medication Use

Figure 15:
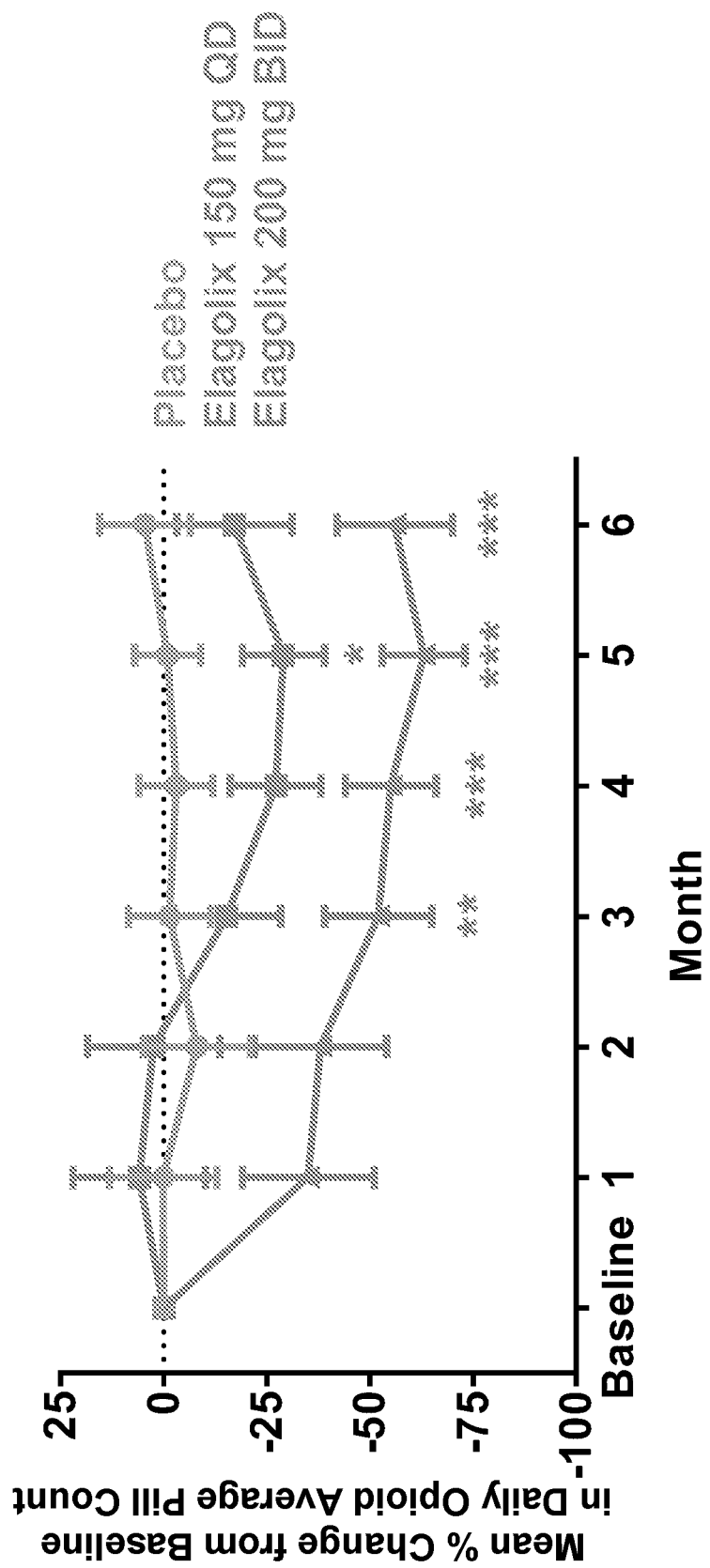
FIG. 15: Depicts rescue opioid pill counts results as mean percentage change from baseline. Significance vs. placebo is indicated for $P<0.05$ (*) and $P<0.001$ (***) from an ANCOVA model. Month=35-day interval.

In these studies, women taking elagolix 200 mg BID reduced the amount of opioid (hydrocodone with acetaminophen) or naproxen rescue medication used to treat their endometriosis-associated pain compared to the amount required at baseline. In addition, there was a significant reduction in the percentage of days per month of the opioid or naproxen rescue medication use for women taking elagolix 200 mg BID compared to women taking placebo. These effects were less consistently observed for women taking elagolix 150 mg QD. See FIG. 15. Compared with placebo, the 200 mg BID elagolix group had a significant decrease from baseline in the percent change of averaged daily opioid pills at Months 3 through 6. Reduction in pain may be reflected by reduction in pain medication, such as prescription opioids or non-steroidal anti-inflammatory agents (NSAIDs) that may be prescribed or found over the counter, for example, naproxen or acetaminophen. 150 mg once a day or twice a day is also expected to reduce intake of pain medication and show reduction in pain, similarly 300 mg doses whether taken once a day or twice a day, is also expected to reduce intake of pain medication and show reduction in pain. In this pooled analysis of rescue analgesic use in two phase 3 trials, compared with placebo: (1) both doses of elagolix 150 QD and 200 BID, showed a significant reduction in the percentage of days in which rescue opioid medication was taken; (2) 200 mg BID elagolix dose showed a significant reduction in the mean percent daily pill counts; (3) fewer women in each elagolix group had increases in the opioid dose and more women had a decreased or stable opioid dose.

In EM-1 and EM-2, 59% and 60% of patients used an opioid rescue analgesic for pain at baseline. The opioid rescue analgesics used at baseline were predominantly hydrocodone/acetaminophen (HC/APAP) and codeine/APAP at strengths of 5/300-325 mg and 30/300-500 mg. In EM-1, of all patients on an opioid at baseline, 98% and 2% were on HC/APAP and codeine/APAP, respectively. In EM-2, of all patients on an opioid at baseline, 50% were on HC/APAP, 16% were on codeine/APAP, 3% were on codeine, and 32% were on tramadol/APAP.

(c) Effects on Bleeding Patterns

Effects on Menstrual Bleeding Patterns

The effects of elagolix on menstrual bleeding were evaluated for up to 12 months using an electronic daily diary where subjects classified their flow of menstrual bleeding (if present in the last 24 hours) as spotting, light, medium, or heavy. elagolix led to a dose-dependent reduction in mean number of bleeding and spotting days and bleeding intensity in those subjects who reported menstrual bleeding.

TABLE B-3

Mean Bleeding/Spotting Days and Mean Intensity Scores at Month 3

|  | Elagolix 150 mg Once Daily | | Elagolix 200 mg Twice Daily | | Placebo | |
| --- | --- | --- | --- | --- | --- | --- |
|  | Baseline | Month 3 | Baseline | Month 3 | Baseline | Month 3 |
| Mean bleeding/spotting days in prior 28 days | 5.3 | 2.8 | 5.7 | 0.8 | 5.4 | 4.6 |
| Mean Intensity score[a] | 2.6 | 2.2 | 2.5 | 2.0 | 2.6 | 2.4 |

[a]Intensity for subjects who reported at least 1 day of bleeding or spotting during 28 day interval. Scale ranges 1 to 4, 1 = spotting, 2 = light, 3 = medium, 4 = heavy Elagolix also demonstrated a dose-dependent increase in the percentage of women with amenorrhea (defined as no bleeding or spotting in a 56-day interval) over the treatment period. The incidence of amenorrhea during the first six months of treatment ranged from 6-17% for elagolix 150 mg once daily, 13-52% for elagolix 200 mg twice daily and less than 1% for placebo. During the second 6 months of treatment, the incidence of amenorrhea ranged from 11-15% for elagolix 150 mg once daily and 46-57% for elagolix 200 mg twice daily.

After 6 months of therapy with elagolix 150 mg once daily, resumption of menses after stopping was reported by 59%, 87%, and 95% of women within 1, 2, and 6 months respectively. After 6 months of therapy with elagolix 200 mg twice daily, resumption of menses after stopping treatment was reported by 60%, 88%, and 97% of women within 1, 2, and 6 months, respectively.

After 12 months of therapy with elagolix 150 mg once daily resumption of menses after stopping treatment was reported by 77%, 95% and 98% of women within 1, 2, and 6 months respectively. After 12 months of therapy with elagolix 200 mg twice daily resumption of menses after stopping treatment was reported by 55%, 91% and 96% of women within 1, 2, and 6 months respectively.

(VII) Lactation

Risk Summary: No human studies have been conducted to assess the impact of elagolix on milk production, its presence in breast milk, or its effects on the breastfed child. It is not known whether elagolix and its metabolites are present in human breast milk, affect human milk production or have effects on the breastfed infant.

(a) In rats elagolix is secreted minimally via milk.

The developmental and health benefits of breastfeeding should be considered along with the mother's clinical need for elagolix and any potential adverse effects on the breastfed child from elagolix.

(b) Data: Animal Data

Pregnant rats were given diet containing elagolix throughout the gestation and lactation periods to achieve a daily elagolix dose of 400 mg/kg. During nursing the dams and litters were divided into restricted feeding and non-restricted groups to determine whether elagolix was secreted in the mother's milk. At post natal day 10 and 20 elagolix plasma concentrations in pups of the restricted feeding litters were not measurable. In pups of the non-restricted feeding group, elagolix plasma concentrations were measurable and approximately 1% of the mother's plasma concentrations. Using plasma concentrations in pups as a surrogate of exposure via lactation elagolix is considered to be minimally secreted in milk.

(IX) Adverse Reactions (a) Clinical Trials Experience

Because clinical trials are conducted under widely varying conditions, adverse reaction rates observed in the clinical trials of a drug cannot be directly compared to rates in the clinical trials of another drug and may not reflect the rates observed in clinical practice.

The safety of elagolix was evaluated in two six-month placebo-controlled clinical studies (Study EM-I and Study EM-II) in which a total of 952 women were treated with 150 mg QD or with 200 mg BID. The population age range was 18-49 years old. Women who completed six months of treatment and met eligibility criteria continued treatment in two blinded six-month extension studies, for a total treatment duration of up to 12 months.

(b) Adverse Reactions (>1%) Leading to Study Discontinuation

In the two controlled studies (EM-I and EM-II), 5.5% of patients treated with elagolix 150 mg QD and 9.6% of patients treated with elagolix 200 mg BID discontinued therapy due to adverse reactions. Discontinuations for both dosage forms were most commonly due to hot flush (0.8% and 2.5%) and nausea (0.8% and 1.5%). The majority of discontinuation due to hot flushes and nausea occurred within the first 2 months of therapy. No woman discontinued elagolix 150 mg QD for hot flushes during the extension study after receiving it for 6 months in the controlled study.

(c) Common Adverse Reactions:

Adverse reactions reported in ≥5% of women in the two placebo-controlled studies in either elagolix dose group and at a greater frequency than placebo are noted in the following table A-7.

TABLE A-7

Percentage of Patients in Studies EM-I and EM-II with Treatment-Emergent Adverse Reactions Occurring in at Least 5% of Patients (either ELAGOLIX Dose Group) and Greater than Placebo

|  | Elagolix 150 mg QD N = 475 % | Elagolix 200 mg BID N = 477 % | Placebo N = 734 % |
| --- | --- | --- | --- |
| Gastrointestinal Disorders | | | |
| Nausea | 11 | 16 | 13 |
| Infections and Infestations | | | |
| Nasopharyngitis | 6 | 6 | 4 |
| Sinusitis | 5 | 6 | 4 |
| Upper Respiratory Tract Infection | 6 | 4 | 5 |
| Musculoskeletal and Connective Tissue Disorder | | | |
| Arthralgia | 3 | 5 | 3 |
| Nervous System Disorders | | | |
| Headache | 17 | 20 | 12 |
| Psychiatric Disorders | | | |
| Anxiety | 3 | 5 | 3 |
| Insomnia | 6 | 9 | 3 |
| Reproductive System and Breast Disorders | | | |
| Amenorrhoea* | 4 | 7 | <1 |
| Vascular Disorders | | | |
| Hot Flush | 23 | 45 | 9 |

*[See Clinical Studies-Effects on Bleeding Patterns (VII)]

In the extension studies, the adverse reaction profile was similar to that noted in Placebo-controlled studies, as noted in Table A-7.

(d) Less Common Adverse Reactions:

In EM-I and EM-II, adverse reactions reported in ≥300 and <500 in either elagolix dose group and greater than placebo included:
a) Investigations: weight increased;
b) Psychiatric Disorders: depression, irritability, libido decreased, mood swings;
c) Gastrointestinal Disorders: diarrhoea, abdominal pain, constipation;
d) Nervous System Disorders: dizziness; or
e) Skin and Subcutaneous Tissue Disorders: night sweats.

Events of hot flushes were dose-dependent and the majority were assessed as mild to moderate. All other adverse events were comparable between both doses of elagolix. The addition of low dose hormone add-back therapy may reduce the occurrence of symptoms associated with estrogen reductions such as hot flush.

(e) Changes in Bone Mineral Density

In the placebo-controlled and extension clinical studies, BMD was measured by DXA. The BMD data of the lumbar spine from these studies are presented in Table A-8. Changes observed in BMD at other anatomical sites (femoral neck, total hip) were generally smaller than lumbar spine.

TABLE A-8

Mean Percentage Change From Baseline in Bone Mineral Density and Percent of Subjects with Z-score ≤ −1.5 of Lumbar Spine

| | Elagolix 150 mg QD | | | Elagolix 200 mg BID | |
|---|---|---|---|---|---|
| | N | Mean Percent Change (95% CI) | % Subjects Z-score ≤ −1.5 On Treatment | N | Mean Percent Change (95% CI) | % Subjects Z-score ≤ −1.5 |
| Month 6 | 360 | −0.52 (−0.79, −0.26) | 0.8% | 365 | −2.54 (−2.81, −2.28) | 4.1% |
| Month 12 | 235 | −0.87 (−1.29, −0.45) | 1.3% | 217 | −3.76 (−4.19, −3.32) | 5.1% |

Following 12 months of elagolix treatment, no patient on the 150 mg daily dose and less than 1% of patients on the 200 mg BID dose had a Z-score below the normal lower bound of −2.0. In both elagolix treatment groups, there was progressive recovery of BMD at three DXA sites: lumbar spine, total hip and femoral neck at post-treatment months 6 and 12.

Additional analysis from exposure-response modeling shows that for elagolix 150 mg QD, the predicted mean (95% CI) Z-score is 0.23 (0.01-0.45) and 0.18 (—0.04-0.40) at Months 12 and 24, respectively. The model predicts that in subjects who initiate treatment on elagolix 150 mg QD for 3 months then increase the dose to 200 mg BID, the predicted mean (95% CI) Z-score is 0.23 (−0.01-0.47) and 0.11 (−0.13-0.36) at Months 6 and 12, respectively.

(f) Changes in Laboratory Values During Treatment
(i) Lipids

While dose-dependent increases in total cholesterol, low-density lipoprotein cholesterol (LDL-C), high density lipoprotein cholesterol (HDL-C), and triglycerides were noted during elagolix treatment, these values remained generally within the normal range.

Lipid increases typically occurred within 1 to 2 months after the start of elagolix therapy and remained stable thereafter over 12 months. Elevated levels of lipids returned to baseline one month after stopping treatment.

The mean increase from pretreatment baseline in LDL-C was 5.25 mg/dL for 150 mg QD and 13.10 mg/dL for 200 mg BID. The mean increase from pretreatment baseline in HDL-C was 2.24 mg/dL for 150 mg QD and 4.16 mg/dL for 200 mg BID. The mean increase from pretreatment baseline in triglycerides was 0.42 mg/dL for 150 mg QD and 11.08 mg/dL for 200 mg BID following 6-month treatment of elagolix Changes in lipid ratios were minimal due to increases in both LDL-C and HDL-C.

Lipid profiles should be assessed and managed according to current clinical practice guidelines.

(ii) Endometrial Safety

Endometrial biopsies were performed in subjects in Study EM-I and its extension at Month 6 and Month 12. The results indicate a dose-dependent decrease in proliferative and secretory biopsy patterns and an increase in quiescent/minimally stimulated biopsy patterns. There were no abnormal biopsy findings post-baseline, such as endometrial hyperplasia or cancer.

Based on transvaginal ultrasound, during the course of a 3-menstrual cycle study in healthy women, elagolix 150 mg QD and 200 mg BID resulted in a dose dependent decrease in the mean endometrial thickness compared to the pretreatment values.

(X) Decrease in Bone Mineral Density

Elagolix reduces serum estradiol levels in a dose-dependent manner that may also be associated with a dose-dependent decrease in bone mineral density (BMD). There is progressive recovery of BMD at 6 and 12 months after stopping treatment [see Adverse Reactions (6.1)].

Assess BMD by dual-energy x-ray absorptiometry (DXA) after 12 months of continuous use. Discontinue elagolix if BMD Z-score is lower than −2.0 until BMD is in the age-appropriate range.

If use of elagolix continues for longer than 12 months, it is recommended that BMD be assessed as clinically indicated. The loss of BMD in premenopausal women should be considered in the benefit/risk assessment for women receiving elagolix for continuous long-term use.

Consider assessment of BMD sooner than annually in patients at greater risk of low BMD. Risk factors include: taking elagolix 200 mg twice daily, a Z-score of less than −2.0 after a previous course of treatment with elagolix, prior use of GnRH agonists, metabolic bone disease, chronic alcohol and/or tobacco use, anorexia nervosa, strong family history of osteoporosis, or chronic use of drugs that can reduce bone mass such as anticonvulsants or corticosteroids.

Although there are no studies addressing whether calcium and vitamin D may lessen BMD loss in women using elagolix, all patients should have adequate calcium and vitamin D intake.

Clinical studies with GnRH analogs or elagolix (in other populations) suggest the use of low dose hormonal add-back therapy (estrogens/progestins or norethindrone acetate) may be effective in reducing the bone mineral loss which occurs with these agents alone.

(XI) Dosage and Administration (a) Dosing Information

Elagolix will be available as either 150 mg tablets (once daily, QD) or 200 mg tablets (twice daily, BID), 150 mg BID, 300 mg BID or 400 mg QD or 600 mg QD to be taken orally with or without food.

(b) Dosing Recommendation

Based on the severity of symptoms and treatment objectives, use the lowest effective dose [see Clinical Studies (VII)]. Treatment with elagolix may be initiated at any time during a patient's menstrual cycle.

TABLE B-1

In one embodiment, the Recommended Dosage and Duration of Use

| Dosing Regimen | Maximum Treatment Duration | Coexisting Condition |
| --- | --- | --- |
| Initiate treatment with ORILISSA 150 mg once daily | 24 months | None |
| Consider initiating treatment with ORILISSA 200 mg twice daily | 6 months | Dyspareunia |
| Initiate treatment with ORILISSA 150 mg once daily. Use of 200 mg twice daily is not recommended. | 6 months | Moderate hepatic impairment (Child-Pugh Class B) |

No dosage adjustment of elagolix is required in women with mild hepatic impairment (Child-Pugh A).

Compared to women with normal liver function, those with moderate hepatic impairment had approximately 3-fold higher elagolix exposures and those with severe hepatic impairment had approximately 7-fold higher elagolix exposures. Because of these increased exposures and risk for bone loss: Elagolix 150 mg once daily is recommended for women with moderate hepatic impairment (Child-Pugh B) with the duration of treatment limited to 6 months. Use of elagolix 200 mg twice daily is not recommended for women with moderate hepatic impairment. Elagolix is contraindicated in women with severe hepatic impairment (Child-Pugh C).

Each tablet contains 155.2 mg of elagolix sodium equivalent to 150 mg of elagolix. Each tablet contains 207.0 mg of elagolix sodium equivalent to 200 mg of elagolix.

(c) Renal Impairment

No dose adjustment of elagolix is required in women with any degree of renal impairment or end-stage renal disease (including women on dialysis) [see Use in Specific Populations and Clinical Pharmacology].

(d) Hepatic Impairment

No dosage adjustment of elagolix is required in women with mild hepatic impairment (Child-Pugh A). elagolix 150 mg QD regimen is recommended in women with moderate hepatic impairment (Child-Pugh B); the 200 mg BID regimen is not recommended.

Elagolix is contraindicated in women with severe hepatic impairment (Child-Pugh C).

Hepatic Transaminase Elevations

In clinical trials, dose-dependent elevations of serum alanine aminotransferase (ALT) at least 3-times the upper limit of the reference range occurred with elagolix. Use the lowest effective dose of elagolix and is recommended.

Further, patients are instructed to promptly seek medical attention in case of symptoms or signs that may reflect liver injury, such as jaundice. Patients are promptly evaluated for elevations in liver tests to determine whether the benefits of continued therapy outweigh the risks.

In the placebo-controlled clinical trials (Studies EM-1 and EM-2), dose-dependent asymptomatic elevations of serum ALT to at least 3-times the upper limit of the reference range occurred during treatment with ORILISSA (150 mg once daily—1/450, 0.2%; 200 mg twice daily—5/443, 1.1%; placebo—1/696, 0.1%). Similar increases were seen in the extension trials (Studies EM-3 and EM-4).

(e) Suicidal Ideation, Suicidal Behavior, and Exacerbation of Mood Disorders

Subjects using elagolix had a higher incidence of depression and mood changes compared to placebo, and elagolix users subjects with a history of suicidality or depression had a higher incidence of depression compared to users subjects without such a history. Patients with depressive symptoms should be evaluated to determine whether the risks of continued therapy outweigh the benefits. Patients with new or worsening depression, anxiety or other mood changes should be referred to a mental health professional, as appropriate. Patients with suicidal ideation and behavior should seek immediate medical attention. Benefits and risks of continuing elagolix should be revaluated if such events occur and optionally, elagolix should be stopped with worsening or serious depression, anxiety, mood changes or suicidal ideation.

In the placebo-controlled trials (Studies EM-1 and EM-2), elagolix was associated with adverse mood changes, particularly in those with a history of depression.

TABLE B-2

Suicidal Ideation, Suicidal Behavior and Mood Disorders in Studies EM-1 and EM-2

| | Elagolix | | |
| --- | --- | --- | --- |
| Adverse Reactions | 150 mg Once Daily (N = 475) N(%) | 200 mg Twice Daily (N = 477) N(%) | Placebo (N = 734) N (%) |
| Completed Suicide | 1 (0.2) | 0 | 0 |
| Suicidal ideation | 1 (0.2) | 1 (0.2) | 0 |
| Depressed Mood, depression, depressive symptoms and or tearfulness | 13 (2.7) | 29 (6.1) | 17 (2.3) |
| Mood altered, mood swings | 25 (5.7) | 25 (5.2) | 25 (3.4) |

NOTE:
The same subject may be included in more than one row if she reported more than one adverse reaction (e.g., suicidal ideation and depression).

Example A-4. Elagolix Reduces Fatigue in Patients with Moderate to Severe Endometriosis Pain A Phase III study was conducted to assess the effects of elagolix for clinically meaningful reductions in pain and other symptoms. Data provided examined the impact of elagolix on fatigue in women with moderate to severe endometriosis-related pain. In the study of three cohorts, first cohort comprised women who received placebo, second cohort comprised women who received 150 mg of elagolix once daily and third cohort comprised women who received 200 mg of elagolix twice daily. It is expected that 300 mg once daily or twice daily and 600 mg once daily, or similar doses will similarly show reduction in fatigue. Fatigue was assessed using the Patient Reported Outcome Measurement Information System (PROMIS®), Fatigue Short Form (SF) 6a. Six items assessed a range of self-reported symptoms from mild, subjective feelings of tiredness to overwhelming, sustained sense of exhaustion that likely decreases one's ability to execute daily activities and function normally. The domain was divided into the experience of fatigue (frequency, duration and intensity) and impact of fatigue on physical, mental and social activities. All items assessed fatigue over the previous seven days. Responses to each question was filed on a 5-item Likert scale: 1—"Not at all"; 2—"A little bit"; 3—"Somewhat"; 4—"Quite a bit"; and 5—"Very much." The questionnaire was administered at baseline and months 1, 3, and 6. Lower scores indicated less fatigue. Post-hoc, Fatigue SF-6a raw scores were converted to T-scores. The T-score rescales 5 the raw score into a standardized score such that the general population has a mean of 50 and a standard deviation (SD) of 10.

Analysis: Changes from baseline in PROMIS Fatigue SF-6a T-scores were compared between each active treatment (elagolix 150 mg QD and 200 mg BID) and placebo. 1-way Analysis of Covariance (ANCOVA) was utilized. ANCOVA controlled for treatment as main effect. Baseline Fatigue SF-6a T-score included as a covariate.

Figure 16:
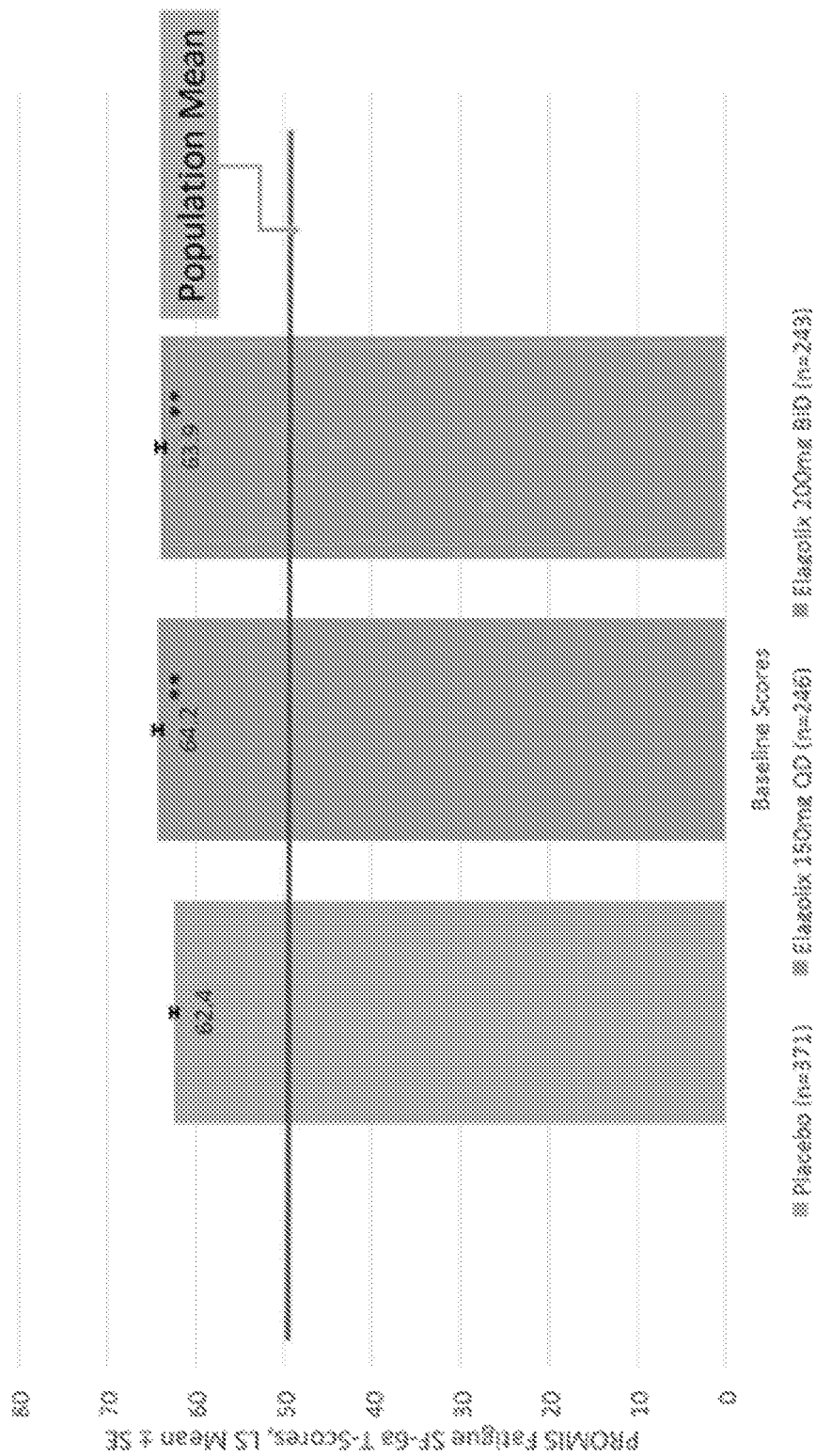
FIG. 16: Depicts that the baseline Promis Fatigue SF-6a T-Scores, on average, were more than 1 SD above the population norm [mean=50; SD=10].  denotes $P<0.01$;  shows statistical significance for elagolix arms versus placebo from ANOVA model for fatigue, including treatment as the main factor. The Maximum SF-6a T-Score=76.8.
Figure 17:
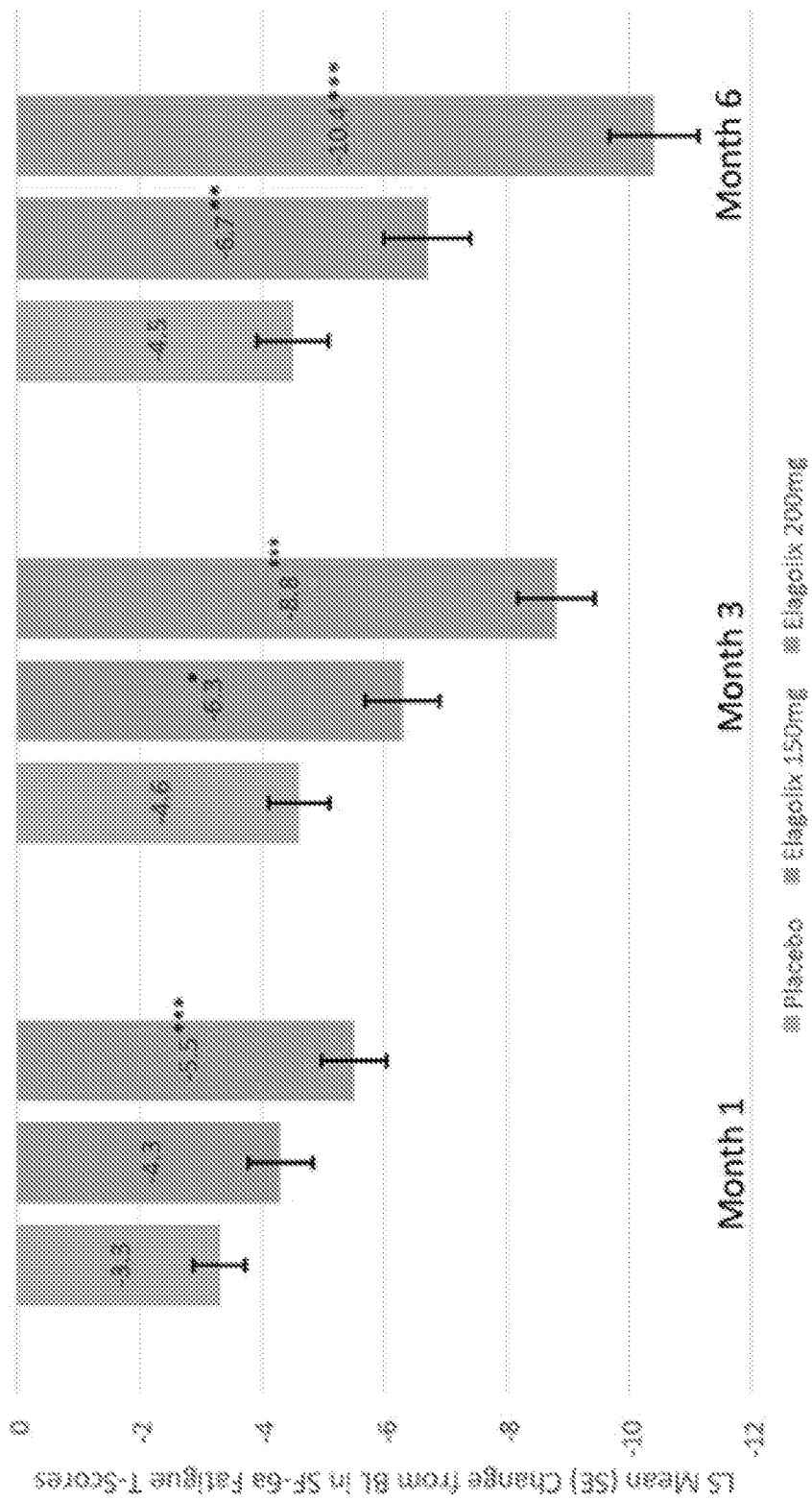
FIG. 17: Depicts that elagolix reduced Fatigue Score from baseline among Endometriosis Patients. Statistical significance versus placebo, $P<0.05$, $<0.01$, $<0.001$ (*,,*), from ANCOVA model for fatigue is shown, including treatment as the main factor and baseline fatigue as a covariate, which compared each treatment group to placebo.

Fatigue among women with endometriosis-related pain remains an unmet medical need. At baseline, women in this study had levels of fatigue that were 1SD worse on average than women in the general population. Compared to placebo, elagolix improved fatigue in a dose dependent manner in women with moderate to sever pain associated with endometriosis. See FIG. 16. Statistically significant reductions relative to placebo in the PROMIS Fatigue SF-6a T-Score observed with both doses of elagolix at Months 3 and 6. A statistically significant reduction in fatigue with elagolix 200 mg was also observed as early as Month 1. See FIG. 17. It is expected that all therapeutic doses of elagolix described above would reduced fatigue in women suffering from moderate to severe endometriosis.

Methods of Practicing the Present Invention

In one aspect of the invention, the methods are practiced by administering pharmaceutical compositions containing elagolix sodium (commonly referred to as elagolix) or 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)-butyric acid. For the purposes of administration, 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)-butyric acid may be formulated as pharmaceutical compositions. Pharmaceutical compositions comprise 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)-butyric acid, or a pharmaceutically acceptable salt thereof, or a solvate thereof, and a pharmaceutically acceptable carrier and/or diluent. 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)-butyric acid is present in the composition in an amount which is effective to treat a particular disorder—that is, in an amount sufficient to achieve GnRH receptor antagonist activity, and preferably with acceptable toxicity to the patient.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the chemical structures, substituents, derivatives, intermediates, syntheses, formulations, or methods, or any combination of such changes and modifications of use of the invention, may be made without departing from the spirit and scope thereof.

All references (patent and non-patent) cited above are incorporated by reference into this patent application. The discussion of those references is intended merely to summarize the assertions made by their authors. No admission is made that any reference (or a portion of any reference) is relevant prior art (or prior art at all). Applicant reserves the right to challenge the accuracy and pertinence of the cited references.

What is claimed is:

1. A pharmaceutical composition comprising:
   from about 20 to about 60% by weight of sodium 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)butanoate ("elagolix sodium");
   from about 10 to about 30% by weight of sodium carbonate; and
   a first filler in an amount from about 20% to about 50% by weight and a second filler in an amount from about 1% to about 20% by weight,
   wherein the first filler is mannitol and the second filler is pregelatinized starch,
   wherein each weight percentage is on the basis of the total weight of the pharmaceutical composition, and
   wherein said composition is in the form of a stable immediate release tablet.

2. The pharmaceutical composition of claim 1, wherein the first filler is present in the pharmaceutical composition in an amount of from about 25% to about 40% by weight.

3. The pharmaceutical composition of claim 1, wherein the first filler is present in the pharmaceutical composition in an amount of about 32% by weight.

4. The pharmaceutical composition of claim 1, wherein the second filler is present in the pharmaceutical composition in an amount of from about 5% to about 15% by weight.

5. The pharmaceutical composition of claim 1, wherein the second filler is present in the pharmaceutical composition in an amount of about 9% by weight.

6. The pharmaceutical composition of claim 1, wherein the sodium carbonate is present in the pharmaceutical composition as sodium carbonate monohydrate.

7. The pharmaceutical composition of claim 1, wherein the elagolix sodium is present in the pharmaceutical composition in an amount equivalent to about 150 mg of Compound A.

8. The pharmaceutical composition of claim 1, wherein the elagolix sodium is present in the pharmaceutical composition in an amount equivalent to about 200 mg of Compound A.

9. The pharmaceutical composition of claim 1, wherein the elagolix sodium is present in the pharmaceutical composition in an amount equivalent to about 300 mg of Compound A.

10. The pharmaceutical composition of claim 1, wherein the pharmaceutical composition further comprises a binder, wherein the binder is present in the pharmaceutical composition in an amount of from about 2 to about 5% by weight.

11. The pharmaceutical composition of claim 10, wherein the binder comprises polyvinylpyrrolidone.

12. The pharmaceutical composition of claim 1, wherein the pharmaceutical composition further comprises a lubricant, wherein the lubricant is present in the pharmaceutical composition in an amount of from about 1 to about 5% by weight.

13. A pharmaceutical composition comprising:
from about 20 to about 60% by weight of sodium 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-l-yl]-1-phenyl-ethylamino)butanoate ("elagolix sodium");
from about 10 to about 30% by weight of sodium carbonate;
a first filler in an amount from about 20% to about 50% by weight and a second filler in an amount from about 1% to about 20% by weight,
wherein the first filler is mannitol and the second filler is pregelatinized starch;
a binder in an amount of from about 2 to about 5% by weight; and
a lubricant in an amount from about 1 to about 5% by weight;
wherein each weight percentage is on the basis of the total weight of the pharmaceutical composition, and
wherein said composition is in the form of a stable immediate release tablet.

14. The pharmaceutical composition of claim 13, wherein the elagolix sodium is present in the pharmaceutical composition in an amount equivalent to about 150 mg of Compound A.

15. The pharmaceutical composition of claim 13, wherein the elagolix sodium is present in the pharmaceutical composition in an amount equivalent to about 200 mg of Compound A.

16. The pharmaceutical composition of claim 13, wherein the elagolix sodium is present in the pharmaceutical composition in an amount equivalent to about 300 mg of Compound A.

* * * * *